United States Patent
Kmiec et al.

(10) Patent No.: US 7,229,767 B2
(45) Date of Patent: Jun. 12, 2007

(54) GENOMICS APPLICATIONS FOR MODIFIED OLIGO NUCLEOTIDES

(75) Inventors: Eric B. Kmiec, Landenberg, PA (US); Howard B. Gamper, Philadelphia, PA (US); Michael C. Rice, Newtown, PA (US); Michael G. Usher, Ann Arbor, MI (US)

(73) Assignee: University of Delaware, Newark, DE (US)

( * ) Notice: Subject to any disclaimer, the term of this patent is extended or adjusted under 35 U.S.C. 154(b) by 433 days.

(21) Appl. No.: 10/672,735

(22) Filed: Sep. 26, 2003

(65) Prior Publication Data

US 2005/0100921 A1   May 12, 2005

Related U.S. Application Data

(63) Continuation of application No. PCT/US02/09691, filed on Mar. 27, 2001.

(60) Provisional application No. 60/325,828, filed on Sep. 28, 2001, provisional application No. 60/279,146, filed on Mar. 27, 2001.

(51) Int. Cl.
 *C07H 21/04* (2006.01)
 *C12P 19/34* (2006.01)
 *C12Q 1/68* (2006.01)

(52) U.S. Cl. ............... 435/6; 435/91.1; 536/23.1; 536/24.3

(58) Field of Classification Search .............. None
See application file for complete search history.

(56) References Cited

U.S. PATENT DOCUMENTS

| | | | |
|---|---|---|---|
| 4,888,274 A | 12/1989 | Radding et al. | |
| 5,223,414 A | 6/1993 | Zarling et al. | |
| 5,273,881 A | 12/1993 | Sena et al. | |
| 5,432,272 A | 7/1995 | Benner | |
| 5,468,629 A | 11/1995 | Calhoun | |
| 5,506,098 A | 4/1996 | Zarling et al. | |
| 5,565,350 A | 10/1996 | Kmiec | |
| 5,670,316 A * | 9/1997 | Sena et al. ................ | 435/6 |
| 5,670,325 A | 9/1997 | Lapidus et al. | |
| 5,674,698 A | 10/1997 | Zarling et al. | |
| 5,698,397 A | 12/1997 | Zarling et al. | |
| 5,719,023 A | 2/1998 | Zarling et al. | |

(Continued)

FOREIGN PATENT DOCUMENTS

EP   0 322 311   12/1988

(Continued)

OTHER PUBLICATIONS

Bryant et al. "On the Mechanism of Renaturation of Complementary DNA strands by RecA Protein of *Escherichia coli*", PNAS, 1985, vol. 82, pp. 297-301.*

(Continued)

*Primary Examiner*—Carla J. Myers
*Assistant Examiner*—Sarae Bausch
(74) *Attorney, Agent, or Firm*—McCarter & English

(57) ABSTRACT

Methods for the production and use of stable complexes of duplex nucleic acid molecules and oligonucleotides are presented. These complexes can be used for the detection and purification of a known nucleic acid target as well as the manipulation of a defined nucleic acid target sequence.

29 Claims, 17 Drawing Sheets

U.S. PATENT DOCUMENTS

| | | | |
|---|---|---|---|
| 5,736,410 | A | 4/1998 | Zarling et al. |
| 5,756,325 | A | 5/1998 | Kmiec |
| 5,760,012 | A | 6/1998 | Kmiec et al. |
| 5,763,240 | A | 6/1998 | Zarling et al. |
| 5,776,744 | A | 7/1998 | Glazer et al. |
| 5,871,984 | A | 2/1999 | Kmiec |
| 5,888,983 | A | 3/1999 | Kmiec et al. |
| 5,891,656 | A | 4/1999 | Zarling et al. |
| 5,912,340 | A | 6/1999 | Kutyavin et al. |
| 5,928,870 | A | 7/1999 | Lapidus et al. |
| 5,929,043 | A | 7/1999 | Dayn |
| 5,948,653 | A | 9/1999 | Pati et al. |
| 5,958,681 | A | 9/1999 | Wetmur et al. |
| 5,965,361 | A | 10/1999 | Kigawa et al. |
| 5,965,427 | A | 10/1999 | Dolgano et al. |
| 5,985,557 | A | 11/1999 | Prudent et al. |
| 6,010,907 | A | 1/2000 | Kmiec et al. |
| 6,043,060 | A | 3/2000 | Imanishi |
| 6,074,853 | A | 6/2000 | Pati et al. |
| 6,107,545 | A | 8/2000 | Mahajan |
| 6,136,601 | A | 10/2000 | Meyer, Jr. et al. |
| 6,150,516 | A | 11/2000 | Brenner et al. |
| 6,159,686 | A | 12/2000 | Kardos et al. |
| 6,174,683 | B1 | 1/2001 | Hahn et al. |
| 6,200,812 | B1 | 3/2001 | Pati et al. |
| 6,245,565 | B1 | 6/2001 | Dayn |
| 6,255,113 | B1 | 7/2001 | Zarling et al. |
| 6,268,490 | B1 | 7/2001 | Imanishi et al. |
| 6,300,543 | B1 | 10/2001 | Cass et al. |
| 6,303,304 | B1 | 10/2001 | Shuber et al. |
| 6,303,376 | B1 | 10/2001 | Glazer |
| 6,312,914 | B1 | 11/2001 | Kardos et al. |
| 6,335,164 | B1 | 1/2002 | Kigawa et al. |
| 6,428,964 | B1 | 8/2002 | Shuber |
| 2001/0044107 | A1 | 11/2001 | Zarling et al. |
| 2002/0032530 | A1 | 3/2002 | Pati et al. |
| 2002/0061530 | A1 | 5/2002 | Belotserkovskii et al. |
| 2002/0090361 | A1 | 7/2002 | Zarling et al. |

FOREIGN PATENT DOCUMENTS

| | | |
|---|---|---|
| EP | 0450370 | 9/1991 |
| EP | 0 687 738 | 2/1995 |
| EP | 0 799 897 | 10/1997 |
| JP | 63-109781 | 5/1988 |
| WO | WO 87/01730 | 3/1987 |
| WO | WO 91/17267 | 11/1991 |
| WO | WO 92/08791 | 5/1992 |
| WO | WO 93/05177 | 3/1993 |
| WO | WO 93/05178 | 3/1993 |
| WO | WO 93/22443 | 11/1993 |
| WO | WO 94/03639 | 2/1994 |
| WO | WO95/18236 | 6/1995 |
| WO | WO 98/08975 | 3/1998 |
| WO | WO 98/39352 | 9/1998 |
| WO | WO 99/14226 | 3/1999 |
| WO | WO 00/50748 | 8/2000 |
| WO | WO 00/56748 | 9/2000 |
| WO | WO 00/66604 | 11/2000 |
| WO | WO 01/73002 | 10/2001 |
| WO | WO 01/92512 | 12/2001 |
| WO | WO 02/10364 | 2/2002 |
| WO | WO 02/10457 | 2/2002 |
| WO | WO 02/077286 | 10/2002 |
| WO | WO 02/079495 | 10/2002 |

OTHER PUBLICATIONS

European Search Report for EP 02 77 6053, (Dec. 29, 2004).
Angov, et al., "The RecA Gene From the Thermophile Thermus Aquaticus YT-1: Cloning, Expression and Characterization", *Journal of Bacteriology*, pp. 1405-1412, Mar. 1994.
Anonymous, "Gene Characterization Kits," *Stratagene Catalog*: p. 39 (1988).
Ascenzioni et al., "Mammalian Artificial Chromosomes—Vectors for Somatic Gene Therapy," *Cancer Letters* vol. 118 No. 2: pp. 135-142 (1997).
Baer et al., "Coping with Kinetic and Thermodynamic Barriers: RMCE, and Efficient Strategy for the Targeted Integration of Transgenes," *Current Opinion in Biotechnology* vol. 12: pp. 473-480 (2001).
Belotserkovskii et al., "DNA Hybrids Stabilized by Heterologies," *Biochemistry* vol. 38: pp. 10785-10792 (1999).
Belovsterkovskii et al., "Peptide Nucleic Acid (PNA) Facilitates Multistranded Hybrid Formation between Linear Double-Stranded DNA Targets and RecA Protein-Coated Complementary Single-Stranded DNA Probes," *Biochemistry* vol. 41: pp. 3686-3692 (2002).
Bianco et al., "RecA Protein," *Encyclopedia of Life Sciences*, MacMillan Reference Ltd: pp. 1-11 (Nov. 20, 1998).
Blake et al., "DNA Sequence of Recombinase-Binding Sites Can Determine Xer Site-Specific Recombination Outcome," *Molecular Microbiology* vol. 23 No. 2: pp. 387-398 (1997).
Brenner et al., "In vitro Cloning of Complex Mixtures of DNA on Microbeads: Physical Separation of Differentially Expressed cDNAs," *Proc. Natl. Acad. Sci. USA* vol. 97 No. 4: pp. 16650-16670 (2000).
Brune et al., "Reviews: Forward with BACs; New Tools for Herpesvirus Genomics," *Trends in Genetics* vol. 16 No. 6: pp. 254-259 (2001).
Bryant, et al., "On the mechanism of renaturation of complementary DNA strands by the recA protein of *Escherichia coli*", *Proc. Natl. Acad. Sci. USA*, 82:297 (1985).
Cassuto, et al., "Partial purification of an activity from human cells that promotes homologous pairing and the formation of heteroduplex DNA in the presence of ATP", *Mol. Ge. Genet.*, 208:10 (1987).
Cheng, et al., "RecA-Directed Hybridication of Psoralen-Monoadducted DNA oligonucleotides to Duplex Targets," in *Photochemical Probes in Biochemistry* (P.E. Nielsen, ed.), pp. 169-177 (1989).
Cheng, et al., "Use of Psoralen-modified oligonucleotides to Trap Three-stranded RecA-DNA Complexes and Repair of These Cross-linked Complexes by ABC Excinuclease." *J. Biol. Chem.* 263:15110 (1988).
Choi et al., "Construction of a Bacterial Artificial Chromosome Library," *Methods in Molecular Biology* vol. 175: pp. 57-68 (2001).
Chow, et al., "Ionic Inhibition of Formation of RecA Nucleoprotein Networks Blocks Homologous Pairing", *PNAC*, vol. 82, pp. 5646-5650, Sep. 1985.
Cox et al., "recA Protein of *Escherichia Coli* Promotes Branch Migration, a Kinetically Distinct Phase of DNA Strand Exchange," *Proc. Natl. Acad. Sci. USA* vol. 78: p. 3433 (1981).
Cox, et al., "Enzymes of General Recombination" *Ann. Rev. Biochem.* 56:229-262 (1987).
D'Amours et al., "The MRE11 Complex: At the Crossroads of DNA Repair and Checkpoint Signalling," *Nature Reviews* vol. 3: pp. 317-327 (May 2002).
Demidov et al., "Kinetics and Mechanism of the DNA Double Helix Invasion by Pseudocomplementary Peptide Nucleic Acids," *Proc. Natl. Acad. Sci. USA* vol. 99 No. 9: pp. 5953-5958 (Apr. 30, 2002).
Dervan, Peter B., "Design of Sequence-Specific DNA-Binding Molecules." *Science*, vol. 232 (Apr. 25, 1986), pp. 464-471.
Di Capua, et al., "Characterization of complexes between recA Protein and Duplex DNA by Electron Microscopy," *J. Mol. Biol.* 157:87-103 (1982).
Dreyer, et al., "Sequence=specific cleavage of single-stranded DNA: Oligodeoxynucleotide-EDTA-Fe(II)", *Proc. Natl. Acad. Sci. USA*, 82:968 (1985).
Dubertret et al., "Single-Mismatch Detection Using Gold-Quenched Fluorescent Oligonucleotides," *Nature Biotchnology* vol. 19: pp. 365-370 (2001).
Eisen, et al., "A recombinase from *Drosophila melanogaster* embryos", *Proc. Natl. Acad. Sci. USA*, 85:7481 (1988).

Eriksson et al., "PNA-Nucleic Acid Complexes. Structure, Stability and Dynamics," *Quarterly Reviews of Biophysics* vol. 29 No. 4: pp. 369-394 (1996).

Fabb et al., "Yeast Artificial Chromosome Vectors," *Molecular and Cell Biology of Human Gene Disorders Therapeutics* vol. 5: pp. 104-124 (1995).

Fan et al., "Parallel Genotyping of Human SNPs Using Generic High-Density Oligonucleotide Tag Arrays," *Genome Research* vol. 10: pp. 853-860 (2000).

Faruqi et al., "Peptide nucleic acid-targeted mutagenesis of a chromosomal gene in mouse cells", *Proc. Natl. Acad. Sci. USA*, 96: 1398-1403 (1998).

Feng et al., "Site-Specific Chromosomal Integration in Mammalian Cells: Highly Efficient CRE Recombinase-Mediated Cassette Exchange," Journal of Molecular Biology vol. 292: pp. 779-785 (1999).

Ferrin et al., "Selective Cleavage of Human DNA: RecA-Assisted Restriction Endonuclease (RARE) Cleavage," *Science* vol. 254: pp. 1494-1497 (1991).

Ferrin et al., "Sequence-Specific Ligation of DNA Using RecA Protein," *Proc. Natl. Acad. Sci. USA* vol. 95: pp. 2152-2157 (Mar. 1998).

Ferrin, et al., "Long-range mapping of gaps and telomeres with RecA-assisted restriction endonuclease (RARE) cleavage", *Nature Genetics*, vol. 6, pp. 379-383, Apr. 1994.

Francois, et al., "Inhibition of Restriction Endo-nuclease Cleavage via Triple helix Formation by Homopyrimidine Oligonucleotides." *Biochem*, 28:9617-9619 (1989).

Francois, et al., "Sequence-specific recognition and cleavage of duplex DNA via triple-helix formation by oligo-nucleotides covalently linked to a phenanthroline-copper chelate." *Proc. Natl. Acad. Sci. USA* 86:9702-9706 (1989).

Freitag, et al., "Affinity Chromatography of RecA Protein and RecA Nucleoprotein Complexes on RecA Protein-Agarose Columns," *J. Biol. Chem.* 263(36):19525-19534(1988).

Fujisawa, et al., "Sequence of the T4 recombination gene, *uvsX*, and its comparison with that of the *recA* gene of *Escherichia coli*", *Nucleic Acids Res.*, 13:7473 (1985).

Fujiyama, et al., "Cloning and structural analyses of hepatitis B virus DNAs, subtype *adr*", *Nucleic Acids Research*, 11:4601 (1983).

Galibert, et al., "Nucleotide sequence of the hepatitis B virus genome (subtype ayw) cloned in *E. coli*", *Nature*, 281:646 (1979).

Gamper et al., "Evidence for a Four-Strand Exchange Catalyzed by the RecA Protein," *Biochemistry* vol. 39: pp. 15272-15281 (2000).

Ganea, et al., "Characterization of an ATP-Dependent DNA Strand Transferase from Human Cells", *Mol. Cell Biol.*, 7:3124 (1987).

Golub, et al., "Inhibition of RNA polymerase II transcription by oligonucleotide-RecA protein filaments targeted to promoter sequences", *Proc. Natl. Acad. Sci.*, USA, vol. 90, pp. 7186-7190, Aug. 1993.

Golub, et al., "Joints Formed by RecA Protein From Oligonucleotides and Duplex DNA Block Initiation and Elongation of Transcription", *Nucleic Acids Research*, vol. 20, No. 12, pp. 3121-3125, 1992.

Gonda, et al., "By Searching Processively RecA Protein Pairs DNA Molecules That Share a Limited Stretch of Homology", *Cell*, 34:647-654 (1983).

Gonda, et al., "The Mechanism of the Search for Homology Promoted by RecA Protein", *The Journal Of Biological Chemistry*, vol. 261, No. 28, pp. 13087-13096, Oct. 1986.

Good et al., "Review: Progress in Developing PNA as a Gene-Targeted Drug," *Antisense Nucleic Acid Drug Development* vol. 7 No. 4: pp. 431-437 (1997).

Gorman et al., "Site-Specific Gene Targeting for Gene Expression in Eukaryotes," *Current Opinion in Biotechnology* vol. 11: pp. 455-460 (2000).

Griffith, et al., "Intercalating Drugs Markedly Affect the ability to the *E. coli* RecA Protein to Insert Small Primers into Homologous Duplex DNA," *J. Call Biochem.* 13E:287(Suppl.)(1989).

Griffith, et al., "RecA Protein Rapidly Crystallizes in the Presence of Spermidine: A Variable Step in its Purification and Physical Characterization", *Biochemistry*, 24:158 (1985).

Halbrook, et al., "Purification and Characterization of a DNA-pairing and Strand Transfer Activity from Mitotic *Saccharomyces cerevisiae*", *Journal of Biological Chemistry*, 264:21403 (1989).

Hanvey, et al., "Site-specific inhibition of EcoRI restriction/modification enzymes by a DNA triple helix." *Nucleic Acids Res.* 18(1):157 (1989).

Henegariu et al., "Custom Fluorescent-Nucleotide Synthesis as an Alternative Method for Nucleic Acid Labeling," *Nature Biotechnology* vol. 18: pp. 345-348 (2000).

Honigberg et al., "The Pairing Activity of Stable Nucleoprotein Filaments Made from recA Protein, Single-Stranded DNA, and Adenosine 5'-(γ-Thio)triphosphate," *Journal of Biological Chemistry* vol. 260 No. 21: pp. 11845-11851 (Sep. 25, 1985).

Honigberg, et al., "Ability of RecA Protein to Promote a Search for Rare Sequences in Duplex DNA", *PNAC*, vol. 83, pp. 9586-9590, Dec. 1986.

Hsieh, et al., "Formation of Joint DNA Molecules by Two Eukaryotic Strand Exchange Proteins Does Not Require Melting of a DNA Duplex", *J. Biol. Chem.*, 264:5089 (1989).

Hsieh, et al., "Pairing of homologous DNA sequences by proteins: evidence for three-stranded DNA," *Genes & Development*, 4:1951 (1990).

Hsieh, et al., "Partial Purification and Characterization of a Recombinase from Human Cells", *Cell*, 44:885 (1986).

Hsieh, et al., "The synapsis event in the homologous pairing of DNAs: RecA recognizes and pairs less than one helical repeat of DNA", *Proc. Natl. Acad. Sci. USA*, 89:6492-6496 (1992).

Huxley, "Review: Mammalian Artificial Chromosomes: A New Tool for Gene Therapy," *Gene Therapy* vol. 1 No. 1: pp. 7-12 (1994).

Hyrup et al., "Review Article: Peptide Nucleic Acids (PNA): Synthesis, Properties and Potential Applications," *Bioorganic and Medicinal Chemistry* vol. 4 No. 1: pp. 5-23 (1996).

Izvolsky et al., "Sequence-Specific Protection of Duplex DNA Against Restriction and Methylation Enzymes by Pseudocomplementary PNAs," *Biochemistry* vol. 39: pp. 10908-10913 (2000).

Jayasena, et al., "Compliment Stabilized D-loop RecA-catalyzed Stable Pairing of Linear DNA Molecules at Internal Sites", *J. Mol. Biol.*, pp. 1015-1024 (1993).

Kato, et al., "RecA Protein From an Extremely Thermophilic Bacterium, Thermus Thermophilus HB8", *J. Biochem*, vol. 114, pp. 926-929, 1993.

Kawashima, et al., "Functional Domains of *Escherichia coli* RecA Protein Deduced From the Mutational Sites in the Gene", *Mol. Gen. Genet.*, vol. 193, pp. 288-292, 1984.

Kenne, et al., "A DNA-recombinogenic activity in human cells", *Nucleic Acids Research*, 12:3057 (1984).

Kido, et al., "*Escherichia coli* RecA Protein Modified with a Nuclear Location Signal Binds to Chromosomes in Living Mammalian Cells," *Experimental Cell Res.* 198:107-114 (1992).

Kirk et al., "Single Nucleotide Polymorphism Seeking Long Term Association with Complex Disease," *Nucleic Acids Research* vol. 30 No. 15: pp. 3295-3311 (2002).

Kirkpatrick, et al., "RecA Protein Promotes Rapid RNA-DNA Hybridization in Heterogeneous RNA Mixtures", *Nucleic Acids Research* pp. 4347-4353.

Kirkpatrick, et al., "RNA-DNA Hybridization Promoted by *E.coli* RecA Protein", *Nucleic Acid Research*, vol. 20, No. 16, pp. 4339-4346, (1992).

Kmiec, et al., "Homologous Pairing of DNA Molecules by Ustilago Rec1 Is Promoted by Sequences of Z-DNA", *Cell*, 29:367-374 (1986).

Kmiec, et al., "Homologous Pairing of DNA Molecules Promoted by a Protein from Ustilago", *Cell*, vol. 29 pp. 367-374 (1982).

Kmiec, et al., "Homologous Pairing Promoted by Ustilago Protein", *Cold Spring Harbor Symposia on Quantitative Biology*, vol. XLIX, 675-679, (1984).

Kmiec, et al., "Synapsis Promoted by Ustilago Rec1 Protein", *Cell*, vol. 36, pp. 593-598, Mar. 1984.

Knight et al., "Tyrosine 264 in the recA Protein from *Escherichia coli* Is the Site of Modification by Photoaffinity Label 8-Azidoadensine", *J. Biol. Chem.* 260 (18):10185-91, Aug. 25, 1985.

Kokoris et al., "High-Throughput SNP Genotyping with the Masscode System," *Molecular Diagnosis* vol. 5 No. 4: pp. 329-340 (2000).

Kolodner, et al., "Purification and characterization of an activity from *Saccharomyces cerevisiae* that catalyzes homologous pairing and strand exchange", *Proc. Natl. Acad. Sci. USA*, 84:5560 (1987).

Koob, et al., "RecA-AC: single-site cleavage of plasmids and chromosomes at any predetermined restriction site", *Nucleic Acids Research*, vol. 20, No. 21, pp. 5831-5836, 1992.

Kowalczykowski, et al., "DNA-strand exchange promoted by RecA protein in the absence of ATP: Impliations for the mechanism of energy transduction in protein-promoted nucleic acid transactions", *Proc. Natl. Acad. Sci. USA*, vol. 92, pp. 3478-3482.

Kowalczykowski, Stephen C., "Biochemistry of Genetic Recombination: Energetics and Mechanism of DNA Strand Exchange," *Annu. Rev. Biophys. Chem.*, vol. 20, pp. 539-575 (1991).

Kricka et al., "Comparison of 5-Hydroxy-2, 3-Dihydrophthalazine-1, 4-Dione and Luminol as Co-Substrates for Detection of Horseradish Peroxidase in Enhanced Chemiluminescent Reactions," *Journal of Immunoassay* vol. 17 No. 1: pp. 67-83 (1996).

Kuramitsu, et al., "A Large-Scale Preparation and Some Physiochemical Properties of RecA Protein", *J. Biochem*, vol. 90, pp. 1033-1045, 1981.

Kwok, Pui-Yan, "Methods for Genotyping Single Nucleotide Polymorphisms," *Annu. Rev. Genomics Hum. Genet.* vol. 2: pp. 235-258 (2001).

Lander et al., "The Chipping Forecast," Supplement to *Nature Genetics* vol. 21 No. 1: pp. 1-60 (Jan. 1999).

Langer et al., "A Genetic Screen Identifies Novel Non-Compatible loxP Sites," *Nucleic Acids Research* vol. 30: pp. 3067-3077 (2002).

Larin et al., "Review: Advances in Human Artificial Chromosome Technology," *Trends in Genetics* vol. 18 No. 6: pp. 313-319 (2002).

Lawrence, et al., "A Fluorescence In Situ Hybridization Approach for Gene Mapping and the Study of Nuclear Organization", *Genome Analysis*, 1:1 (1990).

Leahy, et al., "Topography of the Interaction of recA Protein with Single-stranded Deoxyoligonucleotides," *J. Biol. Chem.*, 261:6954 (1986).

Lohse et al., "Double Duplex Invasion by Peptide Nucleic Acid: A General Principle for Sequence-Specific Targeting of Double-Stranded DNA," *Proc. Natl. Acad. Sci. USA* vol. 96 No. 21: pp. 11804-11808 (Oct. 12, 1999).

Lovett, et al.,, "Purification of a RecA Protein Analogue from *Bacillus subtilis*," *J. Biol. Chem.*, vol. 260, No. 6 pp. 3305-3313 (1985).

Lowenhaupt, et al., "*Drosophila melanogaster* Strand Transferase", *J. Biol. Chem.*, 264:20568 (1989).

Lundqvist et al., "Influence of Different Luminols on the Characteristics of the Chemiluminescense Reaction in Human Neutrophils," *J. Biolumin. Chemilumin.* vol. 10 No. 6: pp. 353-359 (1995).

Madiraju et al., "Properties of a Mutant *recA*-Encoded Protein Reveal a Possible Role for *Escherichia Coli recF*-Encoded Protein in Genetic Recombination," *Proc. Natl. Acad. Sci. USA* vol. 85 No. 18: pp. 6592-6596 (1988).

Maher III, et al., "Inhibition of DNA BInding Proteins by Oligonucleotide-Directed Triple Helix Formation," *Science* 245:725-730 (1989).

Makino, et al., "Monoclonal Antibodies with Specific Effects on Partial Activities of recA Protein of *Escherichia coli*", *J. Biol. Chem.*, 260, 15402, 1985.

McCarthy, et al., "Sensitive homologous recombination strand-transfer assay: Partial purification of a *Drosophila melanogaster* enzyme and detection of sequence effects on the strand-transfer activity of RecA protein", *Proc. Natl. Acad. Sci. USA*, 85:5854 (1988).

McEntee, et al., "Binding of the recA Protein of *Escherichia coli* to Single- and Double-Stranded DNA", *J. Biol. Chem.*, 256:8835-8844 (1981).

Menetski, et al., "Enhancement of *Escherichia coli* RecA Protein Enzymatic Function by dATP," *Biochem.* 28:5871-5881 (1989).

Moore, et al., "Purification and Characterization of a Protein from Human Cells Which Promotes Homologous Pairing of DNA", *J. Biol. Chem.*, 19:11108-11117 (1990).

Moreau, et al., "Rec-A Protein-promoted Cleavage of Lex-A Repressor in the Presence of ADP and Structural Analogues of Inorganic Phosphate, the Fluoride Complexes of Aluminum and Beryllium", *J. Biol. Chem.*, 264:2302-2306 (1989).

Morrical, et al., "Stabilization of recA Protein-ssDNA Complexes by the Single-Stranded DNA Binding Protein of *Escherichia coli*", *Biochemistry*, 29:837 (1990).

Moser, et al., "Sequence-Specific Cleavage of Double helical DNA by Triple Helix Formation", *Science* 238:645-650 (1987).

Nielsen et al., "An Introduction to Peptide Nucleic Acid," *Current Issues in Molecular Biology* vol. 1 No. 2: pp. 89-104 (1999).

Nielsen et al., "Peptide Nucleic Acids: On the Road to New Gene Therapeutic Drugs," *Pharmacology and Toxicology* vol. 86: pp. 3-7 (2000).

Nielsen, "DNA Analogues with Nonphosphodiester Backbones," *Annu. Rev. Biophys. Biomol. Struct.* vol. 24: pp. 167-183 (1995).

Nielsen, "Peptide Nucleic Acid: A Versatile Tool in Genetic Diagnostics and Molecular Biology," *Current Opinion in Biotechnology* vol. 12 No. 1: pp. 16-20 (2001).

Nielsen, "Targeting Double Stranded DNA with Peptide Nucleic Acid (PNA)," *Current Medicinal Chemistry* vol. 8 No. 5: pp. 545-550 (2001).

Norden et al., "Base Orientation of Second DNA in Rec-A-DNA Filaments", *The Journal of Biological Chemistry*, 273(25): 15682-15686 (1998).

Peterson et al., "Transgenic Mice Containing a 248-Kb Yeast Artificial Chromosome Carrying the Human Beta-Globin Locus Display Proper Developmental Control of Human Globin Genes," *Proc. Natl. Acad. Sci. USA* vol. 90 No. 16: pp. 7593-7597 (Aug. 15, 1993).

Peterson et al., "Use of Yeast Artificial Chromosomes (Yacs) for Studying Control of Gene Expression: Correct Regulation of the Genes of a Human Beta-Globin Locus YAC Following Transfer to Mouse Erythroleukemia Cell Lines," *Proc. Natl. Acad. Sci. USA* vol. 90 No. 23: pp. 11207-11211 (Dec. 1, 1993).

Podyminogin, et al., "Sequence-Specific Covalent Modification of DNA by Cross-Linking Oligonucleotides. Catalysis by RecA and Implication for the Mechanism of Synaptic Joint Formation", *Biochemistry*, vol. 34, pp. 13098-13108, 1995.

Pusch et al., "MALDI-TOF Mass Spectrometry-Based SNP Genotyping," *Pharmacogenomics* vol. 3 No. 4: pp. 537-548 (2002).

Radding, Charles M., "Helical Interactions in Homologous Pairing and Strand Exchange Driven by RecA Protein", *The Journal of Biological Chemistry*, vol. 266, No. 9, pp. 5355-5358, Mar. 1991.

Radding, Charles M., "Helical RecA Nucleoprotein Filaments Mediate Homologous Pairing and Strand Exchange", *Biochem. Biophys. Acta.*, 1008 (1989), pp. 131-145.

Radding, et al., "Homologous Pairing and Strand Exchange in Genetic Recombination." *Ann. Rev. Genet.* 16:405 (1983) 25:1990.

Revet, et al., "Homologous DNA Targeting with RecA Protein-coated Short DNA Probes with Electron Microscope Mapping on Linear Duplex Molecules", *J. Mol. Biol.*, vol. 232, pp. 779-791, 1993.

Rigas, et al., "Rapid Plasmid Library Screening Using RecA Coated Biotinylated Probes", *PNAC*, vol. 83, pp. 9591-9595, Dec. 1986.

Roca, et al., "The RecA Protein: Structure and Function," *Crit. Rev. Biochem. Molec. Biol.* 25:415 (1990).

Roche Diagnostics GmbH, "Classical Structural Genomics," http://www.roche-applied-science.com/usa/3327175B.pdf.

Roche Diagnostics GmbH, "recA Protein," Cat. No. 1 449 567, Cat. No. 1 449 575, Version 3 (Sep. 1999).

Sena, et al., "Targeting in Linear DNA Duplexes With Two Complementary Probe Strands for Hybrid Stability", *Nature Genetics*, vol. 3, pp. 365-372 (1993).

Shah et al., "Multiple *BCR-ABL* Kinase Domain Mutation Confer Polyclonal Resistance to the Tyrosine Kinase Inhibitor Imatinib (STI571) in Chronic Phase and Blast Crisis Chronic Myeloid Leukemia," *Cancer Cell* vol. 2: pp. 117-125 (Aug. 2002).

Shibata et al., "Homologous Genetic Recombination as an Intrinsic Dynamic Property of a DNA Structure Induced by RecA/Rad51-Family Proteins: A Possible Advantage of DNA over RNA as Genomic Material," *Proc. Natl. Acad. Sci. USA* vol. 98 No. 15: pp. 8425-8432 (Jul. 17, 2001).

Shibata, et al., "Purification of RecA Protein From *Escherichia coli*", *Method in Enzymology*, vol. 100, pp. 197-209.

Shibata, et al., "Purified *Escherichia coli* recA Protein catalyzed homologous pairing of superhelical DNA and single-stranded fragments." *Proc. Natl. Acad. Sci. USA* 76:1638 (1979).

Shibata, T., et al., "Homologous Pairing in Genetic Recombination", *J. Bio. Chem.*, 256:7557 (1981).

Shinohara et al., "Rad51/RecA Protein Families and the Associated Proteins in Eukaryotes," *Mutation Research* vol. 435: pp. 13-21 (1999).

Shinohara, et al., "Cloning of Human, Mouse and Fission Yeast Recombination Genes Homologous to RAD51 and RecA", *Nature Genetics*, vol. 4, pp. 239-243, Jul. 1993.

Shoemaker et al., "Quantitative Phenotypic Analysis of Yeast Deletion Mutants Using a Highly Parallel Molecular Bar-Coding Strategy," *Nature Genetics* vol. 14 No. 4: pp. 450-456 (1996).

Sluka, et al., "Synthesis of a Sequence-Specific DNA-Cleaving Peptide", *Science*, 238:1129 (1987).

Sugino, et al., "ATP-independent DNA strand transfer catalyzed by protein(s) from meiotic cells of the yeast *Saccharomyces cerevisiae*", *Proc. Natl. Acad. Sci. USA*, 85:3683, (1988).

Syvänen, Ann-Christine, "Accessing Genetic Variation: Genotyping Single Nucleotide Polymorphisms," *Nature: Reviews* vol. 2: pp. 930-942 (Dec. 2001).

Szybalski, Waclaw, "RecA-Mediated Achilles' Heel Cleavage," *Current Opinion in Biotechnology* vol. 8: pp. 75-81 (1997).

Teintze, et al., RecA Assisted Rapid Enrichment of Specific Clones From DNA Libraries, *Biochemical and Biophysical Research Communications*, vol. 211, No. 3, pp. 804-811, Jun. 26, 1995.

Thorpe et al., "Enhanced Chemiluminescent Reactions Catalyzed by Horseradish Peroxidase," *Methods in Enzymology* vol. 133: pp. 331-353 (1986).

Tsang, et al., "Networks of DNA and RecA Protein Are Intermediates in Homologous Pairing", *Biochemistry*, vol. 24, pp. 3226-3232, 1985.

Usher et al., "Targeting of a Chimeric Oligonucleotide to dsDNA for Site-Specific Gene Repair," *FAESB Journal* vol. 15 No. 4: Abstract No. 435.2, p. A518 (Mar. 2001).

Yoshimura et al., "Cloning and Sequence of the Human RecA-like Gene cDNA," *Nucleic Acids Research* vol. 21 No. 7: p. 1665 (1993).

Boado, Ruben "Antisense-Mediated Down-Regulation of the Human Huntingtin Gene"; Jnl of Pharmacology and Experimental Therapeutics; vol. 295; No. 1; pp. 239-243 (2000).

Nellemann, Christine "Inhibition of Huntingtin Synthesis by Antisense Oligodeoxynucleotides"; Molecular and Cellular Neuroscience 16; pp. 313-323 (2000).

* cited by examiner

Oligonucleotide Sequence of the Kan⁻ Target

```
  1  CAGGGGATCA AGATCTGATC AAGAGACAGG ATGAGGATCG TTTCGCATGA
 51  TTGAACAAGA TGGATTGCAC GCAGGTTCTC CGGCCGCTTG GGTGGAGAGG
101  CTATTCGGCT ATGACTGGGC ACAACAGACA ATCGGCTGCT CTGATGCCGC
151  CGTGTTCCGG CTGTCAGCGC AGGGGCGCCC GGTTCTTTTT GTCAAGACCG
201  ACCTGTCCGG TGCCCTGAAT GAACTGCAGG ACGAGGCAGC GCGGCTATCG
251  TGGCTGGCCA CGACGGGCGT TCCTTGCGCA GCTGTGCTCG ACGTTGTCAC
301  TGAAGC
```

FIGURE 13

Oligonucleotide Sequence of the Hyg⁻ Target

```
  1  cgctgagata ggtgcctcac tgattaagca ttggtaactg tcagaccaag
 51  tttactcata tactttag attgatttaa aacttcattt ttaatttaaa
101  aggatctagg tgaagatcct ttttgataat ctcatgacca aaatccctta
151  acgtgagttt tcgttccact gagcgtcaga ccccgtagaa aagatcaaag
201  gatcttcttg agatcctttt tttctgcgcg taatctgctg cttgcaaaca
251  aaaaaaccac cgctaccagc ggtggtttgt ttgccggatc aagagctacc
301  aactctttt ccgaaggtaa ctggcttcag cagagcgcag ataccaaata
351  ctgtccttct agtgtagccg tagttaggcc accacttcaa gaactctgta
401  gcaccgccta catacctcgc tctgctaatc ctgttaccag tggctgctgc
451  cagtggcgat aagtcgtgtc ttaccggg
```

FIGURE 15

GENOMICS APPLICATIONS FOR MODIFIED OLIGO NUCLEOTIDES

CROSS REFERENCE TO RELATED APPLICATIONS

This application is a continuation of International application PCT/US02/09691, filed Mar. 27, 2002, which claims benefit from U.S. Provisional Application No. 60/279,146, filed Mar. 27, 2001 and U.S. Provisional Application No. 60/325,828, filed Sep. 28, 2001, the disclosures of which are incorporated herein by reference in their entireties.

FIELD OF THE INVENTION

The technical field of the invention is in the area of the production and use of stable complexes of nucleic acid molecules and oligonucleotides.

BACKGROUND OF THE INVENTION

In the presence of ATP, the *Escherichia coli* RecA protein, or a homologous recombination protein from another organism, catalyzes strand exchange between a number of substrates, including between single- and double-stranded DNAs. A RecA protein coated single-stranded oligonucleotide interacts with double-stranded target nucleic acid sequence homologous to the oligonucleotide in a process called "synapsis." During synapsis an intermediate containing hybridized, partially joined molecules is formed followed by branch migration to form fully hybrid molecules between the original single- and double-stranded DNAs. The extent to which the nucleic acid molecules hybridize is dependent upon the extent of their homology and hybridization between two nucleic acids that are not completely complementary is stabilized in the presence of RecA.

RecA protein can form stable complexes with short oligonucleotides, at least approximately 9 nucleotides in length, in the presence of the non-hydrolyzable ATP analog, ATP-γ-S. These RecA coated nucleic acid complexes can then be mixed with target double-stranded nucleic acid to form triplex nucleic acid structures or "single D-loops," which are extremely unstable in the absence of RecA. Upon removal of RecA protein the single D-loop joints are stable in supercoiled but very unstable in relaxed DNA.

Addition of a second oligonucleotide that recognizes the strand of the target nucleic acid opposite to the first oligonucleotide results in the formation of a complement-stabilized or "double" D-loop structure. Although this structure is more stable after removal of RecA than the single D-loop structure, the stability depends on the length of the oligonucleotides, and when two DNA oligonucleotides are used the oligonucleotides generally must be at least about 80 nucleotides. See, for example, U.S. Pat. No. 5,670,316, which is incorporated herein by reference in its entirety. Previous efforts to enhance the stability of a double D-loop after removal of RecA involve complex dideoxyoligonucleotides which comprise unusual secondary structures. See, for example, international patent application WO 00/63365, which is incorporated herein by reference in its entirety.

When a linear, double-stranded nucleic acid target and oligonucleotides homologous to the end of the target are used, the structures that are formed at the end of the linear duplex are a subcategory of double D-loops designated "Y-loops". Y-loops can be formed by the same methods used to form double D-loops.

A need exists for stable oligonucleotide:target nucleic acid complexes made using simple, inexpensive oligonucleotides.

SUMMARY OF THE INVENTION

Novel double D-loop or Y-loop complexes (hereafter, "double D-loops") that are surprisingly stable after the removal of recombination proteins ("deproteinization") are described. These stable oligonucleotide:target double D-loops can be generated in recombination protein catalyzed reactions provided that at least one of the oligonucleotides which contain sequences complementary to the target nucleic acid, comprises a modified backbone that enhances hybrid stability or a modified base that enhances hybrid stability. In addition to the exceptional stability of the double D-loops of the invention, the oligonucleotides used to form them can be significantly shorter than the oligonucleotides used in previous methods for forming double D-loops. This discovery provides a number of opportunities for diagnostic applications and methods that exploit the stable double D-loops of the invention.

BRIEF DESCRIPTION OF THE DRAWINGS

FIG. 13. Oligonucleotide sequence of Kan⁻ target. The figure shows the oligonucleotide sequence of the Kan⁻ PCR product used as a target for double D-loop formation. The sequence corresponds to SEQ ID NO: 37.

FIG. 15. Oligonucleotide sequence of Hyg⁻ target. The figure shows the oligonucleotide sequence of the Hyg⁻ PCR product used as a target for double D-loop formation and as non-specific competitor DNA in Example 12. The sequence corresponds to SEQ ID NO: 44.

DETAILED DESCRIPTION OF THE INVENTION

Figure 1:
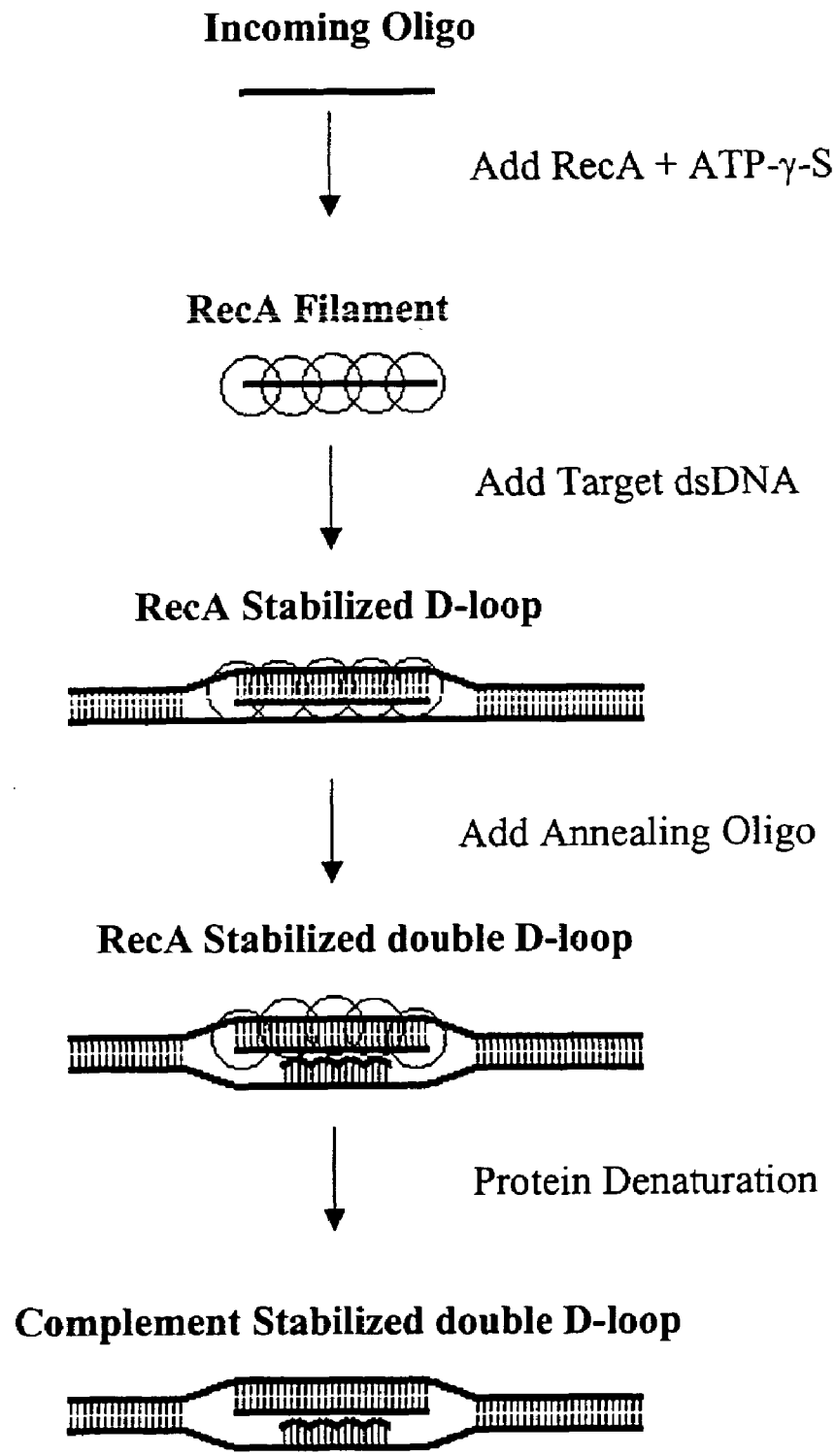
FIG. 1. Flow diagram for the generation of oligonucleotide:target double D-loops. The steps in the method for formation of the double D-loops according to the invention are diagramed.

The present invention describes a method for producing a stable double D-loop and diagnostic methods for detecting and/or isolating a duplex nucleic acid, where the duplex contains an internal target sequence. The target nucleic acid can be any duplex nucleic acid including, for example, linear nucleic acid, relaxed or supercoiled plasmid up to approximately 100 kilobasepairs, larger molecules such as artificial chromosomes including BACs and YACs, and chromosomal DNA. The target nucleic acid molecule can be isolated or it can be targeted in situ. The target nucleic acid molecule can be an artificial sequence, an intragenic sequence or any part of a gene including, for example, an exon, an intron, a promoter, an enhancer or a 3'- or 5'-untranslated region. When larger molecules are isolated care must be taken to avoid shearing.

The method provides a first oligonucleotide that contains sequence complementary to one strand of the target duplex nucleic acid molecule and a second oligonucleotide that contains sequence complementary to the other strand of the target duplex nucleic acid molecule. The first oligonucleotide, which is also designated the "incoming" oligonucleotide, can be bound by RecA. In a particularly useful embodiment, the second oligonucleotide which is also designated the "annealing" oligonucleotide is substantially not bound by RecA. An oligonucleotide is substantially not bound by RecA is for example, an oligonucleotide that is not coated with RecA, i.e. has not been incubated with RecA prior to addition to the reaction mixture. The incoming and annealing oligonucleotides also share a region of complementarity to each other and at least one oligonucleotide is a "modified" oligonucleotide. A modified oligonucleotide further comprises at least one "locked" nucleic acid ("LNA") residue, ribonucleic acid residue, peptide nucleic acid ("PNA") residue or a modified base that enhances hybrid stability. In a particularly useful embodiment, the annealing oligonucleotide is a modified oligonucleotide. Other modified bases that enhance hybrid stability may also be used including, for example, 2-aminoadenine or cytosine/uracil substituted at the 5 position with a methyl, propynyl or bromo group.

Particularly useful among such modifications are PNAs, which are oligonucleotide analogs where the deoxyribose backbone of the oligonucleotide is replaced by a peptide backbone. One such peptide backbone is constructed of repeating units of N-(2-aminoethyl)glycine linked through amide bonds. Each subunit of the peptide backbone is attached to a nucleobase (also designated "base"), which may be a naturally occuring, non-naturally occuring or modified base. PNA oligomers bind sequence specifically to complementary DNA or RNA with higher affinity than either DNA or RNA. Accordingly, the resulting PNA/DNA or PNA/RNA duplexes have higher melting temperatures ($T_m$). In addition, the $T_m$ of the PNA/DNA or PNA/RNA duplexes is much less sensitive to salt concentration than DNA/DNA or DNA/RNA duplexes. The polyamide backbone of PNAs is also more resistant to enzymatic degradation.

The synthesis of PNAs is described, for example, in WO 92/20702 and WO 92/20703, the contents of which are incorporated herein by reference in their entireties. Other PNAs are illustrated, for example, in WO 93/12129 and U.S. Pat. No. 5,539,082, issued Jul. 23, 1996, the contents of which are incorporated herein by reference in their entireties. In addition, many scientific publications describe the synthesis of PNAs as well as their properties and uses. See, for example, Patel, Nature, 1993, 365, 490; Nielsen et al., Science, 1991, 254, 1497; Egholm, J. Am. Chem. Soc., 1992, 114, 1895; Knudson et al., Nucleic Acids Research, 1996, 24, 494; Nielsen et al., J. Am. Chem. Soc., 1996, 118, 2287; Egholm et al., Science, 1991, 254, 1497; Egholm et al., J. Am. Chem. Soc., 1992, 114, 1895; and Egholm et al., J. Am. Chem. Soc., 1992, 114, 9677.

Useful modifications also include one or more monomers from the class of synthetic molecules known as locked nucleic acids (LNAs). LNAs are bicyclic and tricyclic nucleoside and nucleotide analogs and the oligonucleotides that contain such analogs. The basic structural and functional characteristics of LNAs and related analogs are disclosed in various publications and patents, including WO 99/14226, WO 00/56748, WO 00/66604, WO 98/39352, U.S. Pat. No. 6,043,060, and U.S. Pat. No. 6,268,490, all of which are incorporated herein by reference in their entireties.

The general LNA structure may be described by the following formula:

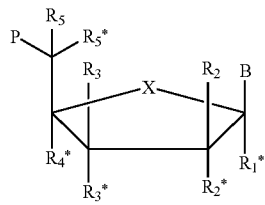

wherein X is selected from —O—, —S—, —N(R$^{N*}$)—, —C(R$^6$R$^{6*}$)—, —O—C(R$^7$R$^{7*}$)—, —C(R$^6$R$^{6*}$)—O—, —S—C(R$^7$R$^{7*}$)—, —C(R$^6$R$^{6*}$)—S—, —N(R$^{N*}$)—C(R$^7$R$^{7*}$)—, —C(R$^6$R$^{6*}$)—N(R$^{N*}$)—, and —C(R$^6$R$^{6*}$)—C(R$^7$R$^{7*}$)—;

B is selected from hydrogen, hydroxy, optionally substituted C$_{1-4}$-alkoxy, optionally substituted C$_{1-4}$-alkyl, optionally substituted C$_{1-4}$-acyloxy, and the nucleobases;

P designates an internucleoside linkage to an adjacent monomer, or a 5'-terminal group, such internucleoside linkage or 5'-terminal group optionally including the substituent R$^5$;

one of the substituents R$^2$, R$^{2*}$, R$^3$, and R$^{3*}$ is a group P* which designates an internucleoside linkage to an adjacent monomer, or a 3'-terminal group;

one or two pairs of non-geminal substituents selected from the present substituents of R$^{1*}$, R$^{4*}$, R$^5$, R$^{5*}$, R$^6$, R$^{6*}$, R$^7$, R$^{7*}$, R$^{N*}$, and the ones of R$^2$, R$^{2*}$, R$^3$, and R$^{3*}$ not designating P* each designates a covalent bridging moiety consisting of one or more of the following substituents: —C(R$^a$R$^b$)—, —C(R$^a$)=C(R$^b$)—, —C(R$^a$)=N—, —O—, —Si(R$^a$R$^b$)—, —S—, —SO$_2$—, —N(R$^a$)—, and >C=Z, wherein Z is selected from —O—, —S—, and —N(R$^a$)—, and R$^a$ and R$^b$ each is independently selected from hydrogen, optionally substituted C$_{1-12}$-alkyl, optionally substituted C$_{2-12}$-alkenyl, optionally substituted C$_{2-12}$-alkynyl, hydroxy, C$_{1-12}$-alkoxy, C$_{2-12}$-alkenyloxy, carboxy, C$_{1-12}$-alkoxycarbonyl, C$_{1-12}$-alkylcarbonyl, formyl, aryl, aryloxycarbonyl, aryloxy, arylcarbonyl, heteroaryl, heteroaryloxycarbonyl, heteroaryloxy, heteroarylcarbonyl, amino, mono- and di-(C$_{1-6}$-alkyl)amino, carbamoyl, mono- and di-(C$_{1-6}$-alkyl)aminocarbonyl, amino-C$_{1-6}$-alkylaminocarbonyl, mono- and di-C$_{1-6}$-dialkyl)amino-C$_{1-6}$-alkylaminocarbonyl, C$_{1-6}$-alkylcarbonylamino, carbamido, C$_{1-6}$-alkanoyloxy, sulphono, C$_{1-6}$-alkylsulphonyloxy, nitro, azido, sulphanyl, C$_{1-6}$-alkylthio, and the halogens, where aryl and heteroaryl may be optionally substituted, and where two geminal substituents R$^a$ and R$^b$ together may designate optionally substituted methylene (=CH2), and wherein two non-geminal or geminal substitutents selected from R$^a$, R$^b$, and any of the substituents R$^{1*}$, R$^2$, R$^{2*}$, R$^3$, R$^{3*}$, R$^{4*}$, R$^5$, R$^{5*}$, R$^6$ and R$^{6*}$, R$^7$, and R$^{7*}$ which are present and not involved in P, P*, or the covalent bridging moiety or moieties together may form an associated bridging moiety selected from substituents of the same kind as defined before; the pair(s) of non-geminal substituents thereby forming a mono- or bicyclic entity together with (i) the atoms to which the non-geminal substituents are bound and (ii) any intervening atoms; and each of the substituents R$^{1*}$, R$^2$, R$^{2*}$, R$^3$, R$^{4*}$, R$^5$, R$^{5*}$, R$^6$ and R$^{6*}$, R$^7$, and R$^{7*}$ which are present and not involved in P, P*, or the covalent bridging moiety or moieties is independently selected from hydrogen, optionally substituted C$_{1-12}$-alkyl, optionally substituted C$_{2-12}$-alkenyl, optionally substituted C$_{2-12}$-alkynyl, hydroxy, C$_{1-12}$-alkoxy, C$_{2-12}$-alkenyloxy, carboxy, C$_{1-12}$-alkoxycarbonyl, C$_{1-12}$-alkylcarbonyl, formyl, aryl, aryloxycarbonyl, aryloxy, arylcarbonyl, heteroaryl, heteroaryloxycarbonyl, heteroaryloxy, heteroarylcarbonyl, amino, mono- and di(C$_{1-6}$-alkyl)amino, carbamoyl, mono- and di(C$_{1-6}$-alkyl)aminocarbonyl, amino-C$_{1-6}$-alkylaminocarbonyl, mono- and di(C$_{1-6}$-alkyl)amino-C$_{1-6}$-alkylaminocarbonyl, C$_{1-6}$-alkylcarbonylamino, carbamido, C$_{1-6}$-alkanoyloxy, sulphono, C$_{1-6}$-alkylsulphonyloxy, nitro, azido, sulphanyl, C$_{1-6}$-alkylthio, and halogens, where aryl and heteroaryl may be optionally substituted, and where two geminal substituents together may designate oxo, thioxo, imino, or optionally substituted methylene, or together may form a spiro bridging moiety consisting of a 1–5 carbon atom(s) alkylene chain which is optionally interrupted and/or terminated by one or more substituents selected from —O—, —S—, and —(NR$^N$)— where R$^N$ is selected from hydrogen and C$_{1-4}$-alkyl, and where two adjacent (non-geminal) substituents may designate an additional bond resulting in a double bond; and R$^{N*}$, when present and not involved in a covalent bridging moiety, is selected from hydrogen and C$_{1-4}$-alkyl;

and basic salts and acid addition salts thereof.

In the instant specification, the terms "nucleobase" and "base" cover naturally occurring nucleobases as well as non-naturally occurring and modified nucleobases. It should be clear to the person skilled in the art that various nucleobases which previously have been considered "non-naturally occurring" have subsequently been found in nature. Thus, "nucleobase" or "base" include not only the known purine and pyrimidine heterocycles, but also heterocyclic analogs and tautomers thereof. Illustrative examples of nucleobases are adenine, guanine, thymine, cytosine, uracil, purine, xanthine, diaminopurine, 8-oxo-N$^6$-methyladenine, 7-deazaxanthine, 7-deazaguanine, N$^4$,N$^4$-ethanocytosine, N$^6$,N$^6$-ethano-2,6-diaminopurine, 5-methylcytosine, 5-(C$^3$-C$^6$)-alkynylcytosine, 5-fluorouracil, 5-bromouracil, pseudoisocytosine, 2-hydroxy-S-methyl-4-triazolopyridine, isocytosine, isoguanine, inosine and the "non-naturally occurring" nucleobases described in U.S. Pat. No. 5,432,272. The terms "nucleobase" and "base" are intended to cover each of these examples as well as analogs and tautomers thereof. Especially interesting nucleobases are adenine, guanine, thymine, cytosine, and uracil.

As is evident from the general formula above, and the definitions associated therewith, there may be one or several asymmetric carbon atoms present in the oligomers, depending on the nature of the substituents and possible covalent bridging moieties. The oligomers used in the present invention are intended to include all stereoisomers arising from the presence of any and all isomers of the individual monomer fragments as well as mixtures thereof, including racemic mixtures. Also included within the scope of the invention are variants of the general formula where B is in the α-configuration.

When considering the definitions and the known nucleosides (naturally occurring and non-naturally occurring) and nucleoside analogs (including known bi- and tricyclic analogs), it is clear that an oligomer may comprise one or more LNA(s) (which may be identical or different from one another, both with respect to the selection of substituent and with respect to selection of covalent bridging moiety) and one or more nucleosides and/or nucleoside analogs. In the instant specification "oligonucleotide" means a successive chain of nucleosides connected via internucleoside linkages; however, it should be understood that a nucleobase in one or more nucleotide units (monomers) in an oligomer (oligonucleotide) may have been modified with a substituent B as defined above.

As described above, the monomeric nucleosides and nucleoside analogs of an oligomer are connected with other monomers via an internucleoside linkage. In the present context, the term "internucleoside linkage" means a linkage consisting of 2 to 4, preferably 3, substituents selected from —$CH_2$—, —O—, —S—, —$NR^H$—, >C=O, >C=$NR^H$, >C=S, —Si(R")$_2$—, —SO—, —S(O)$_2$—, —P(O)$_2$—, —PO($BH_3$)—, —P(O,S)—, —P(S)$_2$—, —PO(R")—, —PO(O$C^H$3)—, and —PO(NH$R^H$)—, where $R^H$ is selected from hydrogen and $C_{1-4}$-alkyl, and R" is selected from $C_{1-6}$-alkyl and phenyl. In some cases, the internucleoside linkage may be chiral. The oligomers used in the present invention are intended to include all stereoisomers arising from ine presence of any and all isomers of the individual internucleoside linkages as well as mixtures thereof, including racemic mixtures.

In one series of useful embodiments, as disclosed in WO 99/14226 and U.S. Pat. No. 6,268,490, LNAs contain a methylene bridge connecting the 2'-oxygen of the ribose with the 4'-carbon according to the following formula:

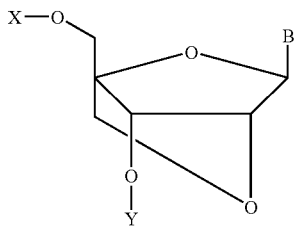

where B is a nucleobase, and X and Y are internucleoside linkages. Without intending to be bound by theory, the covalent bridging moiety of these analogs is believed to reduce the conformational flexibility of the ribose ring by locking it in a 3'-endo conformation and to thereby increase the local organization of the phosphate backbone.

In other interesting embodiments of this structure, the 2'-oxygen position is substituted with nitrogen or sulfur as shown in the following structures:

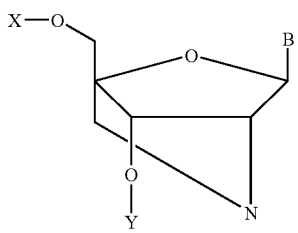

-continued

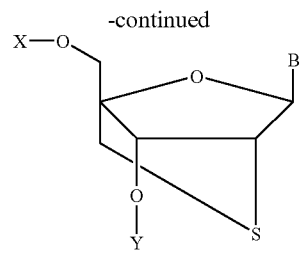

where B is a nucleobase, and X and Y are internucleoside linkages.

In other useful embodiments of the basic LNA structure, as disclosed in WO 99/14226, the covalent bridging moiety may include more than one carbon atom and may span other positions within the ribose ring according to the following structure

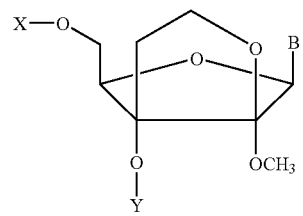

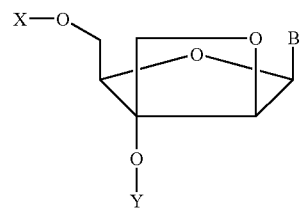

where B is a nucleobase, and X and Y are internucleoside linkages.

Alternatively, oligonucleotides of the present invention may include oligomers comprising at least one nucleoside having a xylo-LNA structure as disclosed in WO 00/56748 and having the general formula:

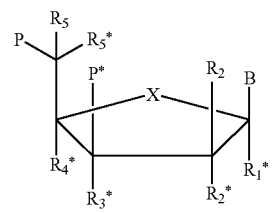

where the internucleoside linkages are designated by P and P*, and the other groups may be the substituents disclosed in WO 00/56748. Specific examples of this analog are disclosed in WO 00/50748 with the following structural framework:

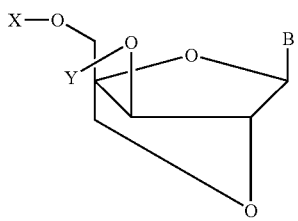

where B is a nucleobase, and X and Y are internucleoside linkages. Also disclosed in WO 00/56748 and considered within the scope of the current invention are nucleoside analogs that contain linkages between the 2' and 5' carbons of the ribose ring:

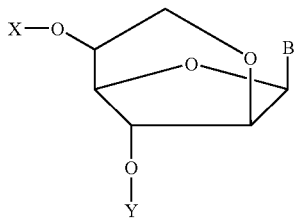

where B is a nucleobase, and X and Y are internucleoside linkages.

Other embodiments of the invention may include oligomers comprising at least one nucleoside having an L-Ribo-LNA structure as disclosed in WO 00/66604 and having the general formula:

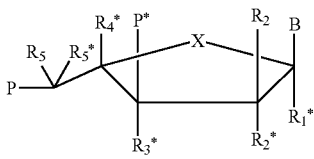

where the internucleoside linkages are designated by P and P*, and the other groups may be the substituents disclosed in WO 00/66604. Specific examples of this analog are disclosed in WO 00/66604 with the following structural framework:

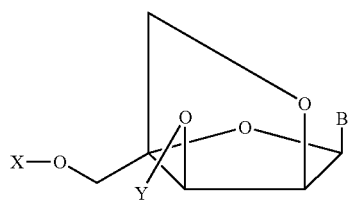

where B is a nucleobase, and X and Y are internucleoside linkages.

Other embodiments considered within the scope of the present invention include oligonucleotides that contain the nucleoside analogs disclosed in U.S. Pat. No. 6,043,060. These analogs are represented by monomer units of the general formula:

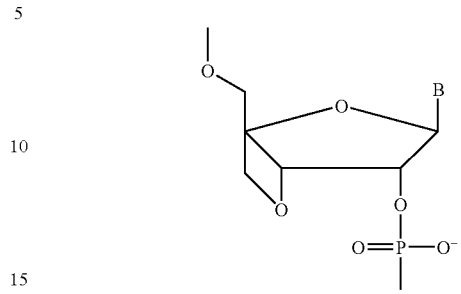

where B is a pyrimidine or purine nucleic acid base, or a derivative thereof, and where, within an oligomer, the plurality of B substituents may be identical to or different from one antoher.

Synthesis of the nucleosides and nucleoside analogs of the present invention and the oligomers that contain them can be performed as disclosed in WO 99/14226, WO 00/56748, WO 00/66604, WO 98/39352, U.S. Pat. No. 6,043,060, and U.S. Pat. No. 6,268,490.

It will be understood by one of skill in the art that the oligonucleotide sequence of the incoming oligonucleotide is complementary to one strand of the duplex target nucleic acid molecule and the annealing oligonucleotide is complementary to the other strand. It will further be understood by one of skill in the art that the incoming oligonucleotide can be complementary to either strand of the duplex target nucleic acid molecule and, therefore, that the annealing oligonucleotide can also be complementary to either strand of the duplex target nucleic acid molecule.

In a useful embodiment, the first or incoming oligonucleotide is a DNA oligonucleotide and the second or annealing oligonucleotide comprises a modified nucleic acid residue. The incoming oligonucleotide is coated with RecA protein and the oligonucleotides are then combined with a duplex nucleic acid target molecule which contains the target sequence under conditions that produce an oligonucleotide: target double D-loop. In one embodiment, the RecA-coated incoming oligonucleotide is added and the single D-loop is allowed to form before the addition of the annealing oligonucleotide. In another embodiment of the invention the oligonucleotides are added simultaneously. The resulting double D-loop contains both the incoming and annealing oligonucleotides and both strands of the duplex nucleic acid target molecule.

The double D-loops formed according to the methods of the invention are formed more efficiently than double D-loops formed with two DNA oligonucleotides. The yield of double D-loops formed according to the methods of the invention is greater than the yield of double D-loops formed with two DNA oligonucleotides by at least about two, three, four, five, six, seven, eight, nine, ten, twelve, fifteen, twenty, or thirty fold or more. The yield of double D-loops formed according to the methods of the invention is at least about 10%, 20%, 30%, 40%, 50%, 60%, 70%, 80% or 90%.

The double D-loops formed according to the methods of the invention are also substantially more stable than double D-loops formed with two DNA oligonucleotides. The double D-loops formed according to the methods of the invention using oligonucleotides that are complementary to the target nucleic acid sequence are stable at or below, for example, 4° C., 15° C., 20° C., 25° C., 30° C., 37° C., 45° C., 50° C. and room temperature. In this context, "stable" indicates that the half-life at a given temperature of a double D-loop formed with oligonucleotides according to the methods of the invention is at least about two, three, four, five, six, seven, eight, nine, ten, twelve, fifteen, twenty, or thirty fold greater than the half-life at the given temperature of a double D-loop formed with two DNA oligonucleotides having the same sequence.

In the present invention "RecA" or "RecA protein" refers to a family of RecA-like recombination proteins having essentially all or most of the same functions, particularly: (i) the ability to position properly oligonucleotides or polynucleotides on their homologous targets for subsequent extension by DNA polymerases; (ii) the ability topologically to prepare duplex nucleic acid for DNA synthesis; and, (iii) the ability of RecA/oligonucleotide or RecA/polynucleotide complexes efficiently to find and bind to complementary sequences. The best characterized RecA protein is from *E. coli*; in addition to the original allelic form of the protein a number of mutant RecA-like proteins have been identified, for example, RecA803. Further, many organisms have RecA-like strand-transfer proteins including, for example, yeast, *drosophila*, mammals including humans, and plants. These proteins include, for example, Rec1, Rec2, Rad51, Rad51B, Rad51C, Rad51D, Rad51E, XRCC2 and DMC1. See, for example, Fugisawa, H., et al.; Hsieh, P., et al., 1986; Hsieh, P., et al., 1989; Fishel, R. A., et al.; Cassuto, E., et al.; Ganea, D., et al.; Moore, S. P., et al.; Keene, K., et al.; Kmiec, E. B., 1984; Kmeic, E. B., 1986; Kolodner, R., et al.; Sugino, A., et al.; Halbrook, J., et al.; Eisen, A., et al.; McCarthy, J., et al., Lowenhaupt, K., et al. In a particularly useful embodiment the recombination protein is the RecA protein of *E. coli*. Alternatively, the RecA protein can be the mutant RecA-803 protein of *E. coli*, a RecA protein from another bacterial source or a homologous recombination protein from another organism.

The RecA protein coating reactions used in the methods of the present invention can be carried out using a variety of co-factors, including, for example, ATP-γ-S, GTP-γ-S, mixes of ATP-γ-S and rATP, or rATP alone in the presence of a rATP regenerating system. In a particularly useful embodiment the RecA protein coating reactions of the methods of the present invention are carried out using ATP-γ-S.

In one embodiment of the invention the oligonucleotides are of equal length. In a useful embodiment, the incoming oligonucleotide is longer than the second oligonucleotide. In some useful embodiments, the region of overlap between the oligonucleotides is at least about 15 base pairs and less than about 500 base pairs. In other useful embodiments, the region of overlap between the oligonucleotides is at least about 10 base pairs and less than about 100 base pairs. In one embodiment of the invention, the region of complementary overlap between the oligonucleotides extends the entire length of the shorter oligonucleotide. Either oligonucleotide optionally may also contain an end terminal nucleic acid extension that is not complementary to either target strand. When present, any end terminal nucleic acid extension may be present on either the 5' or the 3' end of the oligonucleotide. When both oligonucleotides contain such an end terminal extension, these nucleic acid extensions optionally may be complementary to each other.

Detection of the oligonucleotides in double D-loops according to the methods of the present invention may be accomplished on the RecA-containing complex, or, optionally, following deproteinization of the oligonucleotide:target complex. The detecting may optionally be followed by separation of the oligonucleotide:target complex from free oligonucleotide and from non-target nucleic acid. Separation includes, for example, gel electrophoresis, capillary electrophoresis, and chromatography. The oligonucleotide:target complex can be deproteinized by a variety of methods including treatment with SDS or proteinase K, as well as standard chemical deproteinization methods, such as phenol-based methods. Such deproteinization can occur after or, optionally, before the detecting.

In another embodiment, the detecting includes the use of a capture system that traps the oligonucleotide:target complex, where one oligonucleotide is labeled with a capture moiety. Generally, one of the oligonucleotides, usually the oligonucleotide that is not labeled with a capture moiety, is also labeled with a detection moiety. For example, one oligonucleotide strand can be biotin labeled and the other radioactively labeled. The oligonucleotide:target complex can then be captured by solid support-streptavidin (or avidin) and detected by, for example, autoradiography or scintillation counting. Alternatively, both oligonucleotides can be labeled with moieties for either capture or detection. For example, one oligonucleotide strand can be biotin labeled and the other digoxigenin labeled. The oligonucleotide: target complex can then be captured/detected by solid support-streptavidin (or avidin)/labeled anti-digoxigenin, or solid support-anti-digoxigenin antibody/labeled streptavidin (or adivin). In one useful embodiment, the solid support is magnetic beads including, for example, Dynabeads™. It will be understood by one of skill in the art that other detectable and/or capturable epitopes can be used in the practice of the instant invention. Where the detecting includes the use of a capture system, it is preferred that the oligonucleotide:target complex be deproteinized. From the foregoing, it is apparent that any combination of capture or detection moieties can be used in the oligonucleotides used to form the double D-loops of the invention. It is also readily apparent to those of skill in the art that a detection using a capture moiety could be further used for the isolation of the nucleic acid molecule.

A wide range of modifications to oligonucleotides that can be used for subsequent capture are known to those of skill in the art, including, for example, labeling the oligonucleotides with biotin and using streptavidin (or avidin) for capture. Alternatively, labeling with an epitope tag and using an antibody that recognizes the epitope for capture, for example, labeling the oligonucleotide with digoxigenin and using an anti-digoxigenin antibody for capture. Haptens that are commonly conjugated to nucleotides for subsequent capture include biotin (biotin-11-dUTP, Molecular Probes, Inc., Eugene, Oreg., USA; biotin-21-UTP, biotin-21-dUTP, Clontech Laboratories, Inc., Palo Alto, Calif., USA), digoxigenin (DIG-11-dUTP, alkali labile, DIG-11-UTP, Roche Diagnostics Corp., Indianapolis, Ind., USA), and dinitrophenyl (dinitrophenyl-11-dUTP, Molecular Probes, Inc., Eugene, Oreg., USA).

The oligonucleotides can also be labeled for detection using a number of different modifications that are well known to those of skill in the art. These modifications include, for example, radioactive nucleotides, biotin- or digoxigenin-conjugated nucleotides, or fluorescent modifications. Commercially available fluorescent nucleotide analogs readily incorporated into the nucleic acids of the present invention include, for example, Cy™3-dCTP, Cy™3-dUTP, Cy™5-dCTP, Cy™5-dUTP (Amersham Pharmacia Biotech, Piscataway, N.J., USA), fluorescein-12-dUTP, tetramethylrhodamine-6-dUTP, Texas Red®-5-dUTP, Cascade Blue®-7-dUTP, BODIPY® FL-14-dUTP, BODIPY® R-14-dUTP, BODIPY® TR-14-dUTP, Rhodamine Green™-5-dUTP, Oregon Green® 488-5-dUTP, Texas Red®-12-dUTP, BODIPY® 630/650-14-dUTP, BODIPY® 650/665-14-dUTP, Alexa Fluor® 488-5-dUTP, Alexa Fluor® 532-5-dUTP, Alexa Fluor® 568-5-dUTP, Alexa Fluor® 594-5-dUTP, Alexa Fluor® 546-14-dUTP, fluorescein-12-UTP, tetramethylrhodamine-6-UTP, Texas Red®-5-UTP, Cascade Blue®-7-UTP, BODIPY® FL-14-UTP, BODIPY® TMR-14-UTP, BODIPY® TR-14-UTP, Rhodamine Green™-5-UTP, Alexa Fluor® 488-5-UTP, Alexa Fluor® 546-14-UTP (Molecular Probes, Inc. Eugene, Oreg., USA). Fluorescein labels can also be used to capture or isolate a target using commercially available anti-fluorescein antibodies. Radioactive labels can be identified by, for example, autoradiography or scintillation counting. The presence of biotin or digoxigenin can be detected by streptavidin or an anti-digoxigenin antibody, respectively, where the streptavidin (or avidin) or anti-digoxigenin is radioactively labeled, enzyme labeled (e.g., alkaline phosphatase, peroxidase, beta-galactosidase or glucose oxidase) or fluorochrome-labeled (e.g., fluorescein, R-phycoerythrin, or rhodamine).

In another embodiment a detecting oligonucleotide is a "molecular beacon" such as those described in U.S. Pat. No. 6,177,555, the disclosure of which is incorporated herein by reference in its entirety. A molecular beacon is a unimolecular nucleic acid molecule comprising a stem-loop structure, wherein the stem is formed by intramolecular base pairing of two complementary sequences such that the 5' and 3' ends of the nucleic acid are at the base of the stem. The loop links the two strands of the stem, and is comprised of sequence complementary to the sequence to be detected. A fluorescent group is covalently attached to one end of the molecule, and a fluorescence quenching group is attached to the other end. In the stem-loop configuration, these two moieties are physically adjacent to one another. Thus, when the molecular beacon is illuminated with light corresponding to the excitation wavelength of the fluorescent group, the proximity of the fluorescence quenching group prevents fluorescence. However, when the molecular beacon hybridizes to sequence complementary to the loop, the fluorescent group and the quenching group become physically separated such that the quenching group no longer absorbs light emitted from the fluorescent group. Thus, binding of the molecular beacon to its target nucleic acid sequence is detected by an increase in fluorescence emission from the fluorescent group. It is possible to simultaneously use two or more molecular beacons with different sequence specificities in the same assay where each molecular beacon is labeled with at least a different fluorescent group. The bound oligonucleotides are then detected by monitoring for the spectral changes characteristic for the binding of each particular molecular beacon to its complementary sequence.

In a particularly useful embodiment, hybridization of an oligonucleotide of the invention is detected by fluorescence resonance energy transfer ("FRET"). FRET and similar terms refer to the situation where a donor fluorophore can transfer resonance energy to an acceptor fluorophore such that the acceptor fluorophore produces a measurable fluorescence emission. If the donor fluorophore and acceptor fluorophore are too far apart, then the donor fluorophore can not effectively transfer resonance energy to the acceptor fluorophore. However, adjacent hybridization of two oligonucleotides can be detected where one oligonucleotide is labeled with a donor fluorophore and the other oligonucleotide is labeled with an acceptor fluorophore such that the donor fluorophore can transfer resonance energy to the acceptor fluorophore which then produces measurable fluorescence emission. A double D-loop can be formed according to the methods of the invention that contains more than two oligonucleotides, e.g., one incoming oligonucleotide and two annealing oligonucleotides. Annealing of said two annealing oligonucleotides could be readily detected by FRET analysis. Procedures for FRET analysis are well known to those of skill in the art and are described, for example, in Cardullo, R. A., et al., "Detection of Nucleic Acid Hybridization by Nonradiative Fluorescence Resonance Energy Transfer," Proc. Natl. Acad. Sci. USA, vol. 85, pp. 8790–8794 (1988); Ghosh, S. S., et al., "Real Time Kinetics of Reduction Endonuclease Cleavage Monitored by Fluorescence Resonance Energy Transfer," Nucleic Acids Research, vol. 22, No. 15, pp. 3155–3159 (1994); and Hiyoshi, M., et al., "Assay of DNA Denaturation by Polymerase Chain Reaction-Driven Fluorescence Resonance Energy Transfer," Analytical Biochemistry, vol. 221, pp. 306–311 (1994), the disclosures of which are incorporated herein by reference in their entireties.

Detection of the oligonucleotides in the oligonucleotide:target complex can also be accomplished, for example, by RNA or DNA polymerase mediated primer extension from the 3'-end of either oligonucleotide, where the primer extension is performed in the presence of one or more dNTPs containing a detectable moiety. For example, the invention contemplates detection using a "rolling circle replication" reporter systems as described in, for example, U.S. Pat. Nos. 5,854,033 and 6,329,150, which are incorporated herein by reference in their entireties. Examples of detectable moieties, include, for example, those that are detectable by chromogenic detection, chemiluminescent detection and fluorescent detection or inorganic labels, such as colloidal gold particles or ferritin. Additional labels that may be used include marker enzymes such as alkaline phosphatase ("AP"), β-galactosidase or horseradish peroxidase, which are detected using a chromogenic substrate. For example, AP may be detected using 5-bromo-4-chloro-3-indolyl phosphate or nitroblue tetrazolium salt. Other labels include fluorescent tags such as fluorescein, rhodamine, and resorufin, and derivatives thereof, as well as coumarins such as hydroxycoumarin.

The methods of the present invention further contemplate one or more additional set(s) of two oligonucleotides which are complementary to additional duplex target sequences. For example, a third and a fourth oligonucleotide, where the third oligonucleotide contains sequence complementary to one strand of a second target sequence and the fourth oligonucleotide contains sequence complementary to the other strand of the second target sequence, where (i) the third and fourth oligonucleotides also have a region of complementary overlap to each other, and (ii) the second set of oligonucleotides does not hybridize to the first set of oligonucleotides. The first and third oligonucleotides are coated with RecA protein in a RecA protein coating reaction and the oligonucleotides are combined with the linear duplex DNA containing the two target sequences. The combining is done under conditions that produce two oligonucleotide:target complexes which contain all four oligonucleotide strands and both target strands. In one embodiment, the first and third oligonucleotides are added and synapsis allowed to proceed prior to the addition of the second and fourth oligonucleotides. Alternatively, the two double D-loops can be formed sequentially. The resulting oligonucleotide:target double D-loops are stable to deproteinization. The presence of one or more of the oligonucleotides is then detected in the oligonucleotide:target complexes according to any of the methods described herein or known to those of skill in the art. In one application multiple double D-loops can be formed at unique sequences within a chromosomal spread and detected by fluorescence microscopy following primer extension conducted in the presence of a fluorescent labeled dNTP. Mapping of sites can be accomplished by carrying out reactions in which each pair of targeting oligonucleotides is sequentially omitted from the cocktail. Resolution is superior to protocols that use single-stranded probes designed to hybridize to denatured DNA. Where there is more than one duplex target sequence, they may be, but need not necessarily be, contiguous, i.e. present in the same nucleic acid molecule. One of skill in the art will understand from that the methods could equally apply to the formation of three, four, five or more separate double D-loops in one or more duplex target nucleic acid molecules.

The method involving two or more sets of oligonucleotides can be utilized in many of the same ways as described above for a single set of oligonucleotides. For example, the first set of oligonucleotides can be labeled with a capture moiety and the second set of oligonucleotides labeled with a detection moiety. Methods involving the formation of two or more double D-loops are particularly useful in the isolation of large nucleic acid molecules. In addition, methods involving two or more sets of oligonucleotides can usefully be combined with the double D-loop-mediated cleavage methods described herein to generate specific deletions in a duplex target nucleic acid molecule.

The double-stranded oligonucleotide:duplex target complexes involving two sets of oligonucleotides can also be used in a RecA protein facilitated DNA amplification method. For example, the two sets of oligonucleotides can be hybridized to their duplex target sequences in the presence of ATP-γ-S and reacted in a reaction mixture comprising: dNTPs, RecA protein and DNA polymerase. This reaction is performed below the temperature required for thermal dissociation of the two target strands and continued until a desired degree of amplification of the target sequence is achieved. The amplification reactions may further include repeated additions of (i) DNA polymerase and (ii) RecA protein-coated probes during the course of the amplification reactions. Other approaches to amplification, which can be applied to the present invention, are describe in U.S. Pat. No. 5,223,414, incorporated herein by reference in its entirety. In each set of oligonucleotides, the 3' end of one oligonucleotide will be internal to the region defined by the two sets of oligonucleotides; these ends are necessary for the amplification reaction. However, the opposite 3' ends of each primer pair, external to the region defined by the two primer sets, can optionally be blocked to inhibit the formation of extension products from these ends. This amplification method can also be used as a detection method or capture method, where detection or capture is accomplished by DNA polymerase facilitated primer extension from the 3'-ends of each oligonucleotide strand, where the primer extension reaction is performed in the presence of dNTP(s) and where one or more dNTP contains a detectable or capture moiety.

An oligonucleotide:target double D-loop can also be used to block cleavage of any targeted restriction site. Blocking cleavage can be accomplished in a number of ways including, for example: (i) forming the oligonucleotide:target double D-loop and treating with restriction enzyme before deproteinization of the complex; (ii) using methylated or un-methylated oligonucleotides, depending on the sensitivity of a selected enzyme to the presence of methyl groups; (iii) introducing a sequence mismatch in each strand of the oligonucleotide, which eliminates the restriction site when the oligonucleotide hybridizes to the target; and (iv) forming the double D-loop and adding an enzyme to add/remove methyl groups to/from the DNA, depending on the sensitivity of a selected enzyme to the presence of methyl groups, at sites that are not within the double D-loop; followed by dissociation of the double D-loop and digestion with the appropriate restriction enzyme. There are many restriction enzymes that are sensitive to the presence of methyl groups in various target sequences, including, for example, AatI, AatII, AccI, AccII, AccIII, Acc65I, AccB7I, AciI, AclI, AdeI, AfaI, AfeI, AflI, AflIII, AflIIII, AgeI, AhaII, AhdI, AloI, AluI, AlwI, Alw21I, Alw26I, Alw44I, AlwNI, AmaI, AorI, Aor51HI, AosII, ApaI, ApaLI, ApeI, ApoI, ApyI, AquI, AscI, Asp700I, Asp718I, AspCNI, AspMI, AspMDI, AtuCI, AvaI, AvaII, AviII, BaeI, BalI, BamFI, BamHI, BamKI, BanI, BanII, BazI, BbeI, BbiII, BbrPI, BbsI, BbuI, BbvI, BbvCI, Bca77I, Bce243I, BceAI, BcgI, BciVI, BclI, BcnI, BepI, BfiI, Bfi57I, Bfi89I, BfrI, BfuI, BglI, BglII, BinI, BloHI, BlpI, BmaDI, Bme216I, Bme1390I, Bme1580I, BmeTI, BmgBI, BnaI, BoxI, BpiI, BplI, BpmI, BpuI, Bpu10I, Bpu1102I, BsaI, Bsa29I, BsaAI, BsaBI, BsaHI, BsaJI, BsaWI, BsaXI, BscI, BscFI, BseCI, BseDI, BseGI, BseLI, BseMI, BseMII, BseRI, BseSI, BseXI, BsgI, Bsh1236I, Bsh1285I, Bsh1365I, BshGI, BshNI, BshTI, BsiBI, BsiEI, BsiHKAI, BsiLI, BsiMI, BsiQI, BsiWI, BsiXI, BslI, BsmI, BsmAI, BsmBI, BsmFI, BsoBI, BsoFI, Bsp49I, Bsp51I, Bsp52I, Bsp54I, Bsp56I, Bsp57I, Bsp58I, Bsp59I, Bsp60I, Bsp61I, Bsp64I, Bsp65I, Bsp66I, Bsp67I, Bsp68I, Bsp72I, Bsp91I, Bsp105I, Bsp106I, Bsp119I, Bsp120I, Bsp122I, Bsp143I, Bsp143II, Bsp1286I, Bsp2095I, BspAI, BspDI, N.BspD6I, BspEI, BspFI, BspHI, BspJ64I, BspKT6I, BspLI, BspLU11III, BspMI, BspMII, BspPI, BspRI, BspST5I, BspT104I, BspT107I, BspXI, BspXII, BspZEI, BsrBI, BsrBRI, BsrDI, BsrFI, BsrPII, BssHII, BssKI, BssSI, BstI, Bst1107I, BstAPI, BstBI, BstEII, BstEIII, BstENII, BstF5I, BstGI, BstKTI, BstNI, BstOI, BstPI, BstSCI, BstUI, Bst2UI, BstVI, BstXI, BstYI, BstZ17I, Bsu15I, Bsu36I, BsuBI, BsuEII, BsuFI, BsuMI, BsuRI, BsuTUI, BtcI, BtgI, BtrI, BtsI, CacI, Cac8I, CaiI, CauII, CbiI, CboI, CbrI, CceI, CcrI, CcyI, CfoI, CfrI, Cfr6I, Cfr9I, Cfr10I, Cfr13I, Cfr42I, CfrBI, CfuI, ClaI, CpeI, CpfI, CpfAI, CpoI, CspI, Csp5I, Csp6I, Csp45I, Csp68KII, CthII, CtyI, CviAI, CviAII, CviBI, M.CviBIII, CviJI, N.CviPII, CviQI, N.CviQXI, CviRI, CviRII, CviSIII, CviTI, DdeI, DpnI, DpnII, DraI, DraII, DraIII, DrdI, DsaV, EaeI, EagI, Eam1104I, Eam1105I, EarI, EcaI, EciI, Ec136II, EclXI, Ecl18kI, Eco24I, Eco31I, Eco32I, Eco47I, Eco47III, Eco52I, Eco57I, Eco72I, Eco88I, Eco91I, Eco105I, Eco147I, Eco1831I, EcoAI, EcoBI, EcoDI, EcoHI, EcoHK31I, EcoKI, EcoO65I, EcoO109I, EcoPI, EcoP15I, EcoRI, EcoRII, M.EcoRII, EcoRV, EcoR124I, EcoR124II, EcoT22I, EheI, EsaBC3I, EsaBC4I, EsaLHCI, Esp3I, Esp1396I, FauI, FbaI, FnuDII, FnuEI, Fnu4HI, FokI, FseI, FspI, Fsp4HI, GsuI, HaeII, HaeIII, HaeIV, HapII, HgaI, HgiAI, HgiCI, HgiCII, HgiDI, HgiEI, HgiHI, HhaI, HhaII, Hin1I, Hin6I, HinPII, HincII, HindIII, HindIII, HinfI, HpaI, HpaII, HphI, Hpy8I, Hpy99I, Hpy99II, Hpy188I, Hpy188III, HpyAIII, HpyAIV, HpyCH4III, HpyCH4IV, HsoI, ItaI, KasI, KpnI, Kpn2I, KspI, Ksp22I, KspAI, Kzo9I, LlaAI, LlaKR2I, MabI, MaeII, MamI, MbiI, MboI, MboII, MflI, MlsI, MluI, Mlu9273I, Mlu9273II, MlyI, MmeI, MmeII, MnlI, MroI, MscI, MseI, MslI, MspI, M.MspI, MspA1I, MspBI, MspR9I, MssI, MstII, MthTI, MthZI, MunI, MvaI, Mva1269I, MvnI, MwoI, NaeI, NanII, NarI, NciI, NciAI, NcoI, NcuI, NdeI, NdeII, NgoBV, NgoBVIII, NgoCI, NgoCII, NgoFVII, Ngo- MIV, NgoPII, NgoSII, NgoWI, NheI, NlaIII, NlaIV, NlaX, NmeSI, NmuCI, NmuDI, NmuEI, NotI, NruI, NsbI, NsiI, NspI, NspV, NspBII, NspHI, PacI, PaeI, PaeR7I, PagI, PauI, PdiI, PdmI, Pei9403I, PfaI, Pfl23II, PflFI, PflMI, PleI, Ple19I, PmaCI, PmeI, PmiI, PpiI, PpuMI, PshAI, Psp5II, Psp1406I, PspGI, PspOMI, PspPI, PstI, PsuI, PsyI, PvuI, PvuII, Ral8I, RalF40I, RflFI, RflFII, Rrh4273I, RsaI, RshI, RspXI, RsrI, RsrII, SacI, SacII, SalI, SalDI, SapI, Sau96I, Sau3239I, Sau3AI, SauLPI, SauMI, Sbo13I, ScaI, Scg2I, SchI, ScrFI, SdaI, SduI, SenPI, SexAI, SfaNI, SfiI, SfoI, SfuI, SgfI, SgrAI, SinI, SmaI, SmlI, SnaBI, SnoI, SolI, SpeI, SphI, SplI, SpoI, SrfI, Sru30DI, SscL1I, Sse9I, Sse8387I, SsoI, SsoII, SspRFI, SstI, SstII, Sth368I, StsI, StuI, StyD4I, StyLTI, StyLTIII, StySJI, StySPI, StySQI, TaaI, TaiI, TaqI, TaqII, TaqXI, TfiI, TflI, ThaI, TliI, TseI, Tsp45I, Tsp509I, TspRI, Tth111I, TthHB8I, Van91I, VpaK11BI, VspI, XapI, XbaI, XceI, XcmI, XcyI, XhoI, XhoII, XmaI, XmaIII, XmiI, XmnI, XorII, XspI, and ZanI. Similarly, many enzymes that can be used to methylate the duplex target nucleic acid molecule (methylases) are known, including, for example, M.AacDam, M.AaoHemKP, M.AarAIP, M.AatII, M.AbrI, M.AccI, M.AccIII, M.AciI, M.AcII, M.AflII, M.AflIII, M.AfuHemKP, M.AfuORF1409P, M.AfuORF1715P, M.AfuORF2345P, M.AgeI, M.AhdI, M.AimAI, M.AimAII, M.AloI, M.AluI, M.AlwI, M.Alw26I, M.ApaI, M.ApaLI, M.ApeKHemKP, M.ApeKORF73P, M.ApeKORF446P, M.ApeKORF554P, M.ApeKORF872P, M.ApeKORF1835P, M.ApeKORF2002P, M.ApoI, M.AquI, M.AscI, M.AseI, M.AsiSI, M.AspCNI, M.AthBP, M.AthI, M.AthIII, M.AthIVP, M.AthVP, M.AthVIP, M.AthVIIP, M.AthVIIIP, M.AtuCHemKP, M.AtuCHemK2P, M.AtuCHemK3P, M.AtuCORF8P, M.AtuCORF1453P, M.AtuCORF1997P, M.AvaI, M.AvaII, M.AvaIII, M.AvaIVP, M.AvaV, M.AvaVI, M.AvaVI, M.AvaVIII, M.AvaIX, M.AvrII, M.BabI, M.BalI, M.BamHI, M.BamHII, M.BanI, M.BanII, M.BanIII, M.BbuB31HemKP, M.Bbulp25ORF2P, M.Bbulp25ORF29P, M.Bbulp56ORF67P, M.BbvI, M.BbvCIA, M.BbvCIB, M.Bce10987IP, M.BceAIA, M.BceAIB, M.BcgI, M.BchI, M.BclI, M.BcnIA, M.BcnIB, M.BepI, M.BfaIA, M.BfaIB, BfaHemKP, M.BfaORFC113P, M.BfaORFC143P, M.BfaORFC157P, M.BfaORFC196P, M.BfaORFC198P, M.BfaORFC205P, M.BfaORFC223P, M.BfaORFC240P, M.BfiIA, M.BfiIB, M.BfuAIA, M.BfuAIB, M.BgII, M.BgIII, M.BhaHemKP, M.BhaORF3508P, M.BhaORF3535P, M.BhaORF4003AP, M.BhaORF4003BP, M.BlpI, M.BmrIA, M.BmrIB, M.BolIP, M.BolIIP, M.BpmIA, M.BpmIB, M.Bpu10IA, M.Bpu10IB, M.BsaIA, M.BsaIB, M.BsaAI, M.BsaJI, M.BsaWI, M.BscGIA, M.BscGIB, M.Bse634I, M.BseCI, M.BseDI, M.BseMII, M.BseRIA, M.BseRIB, M.BseYI, M.BsgIA, M.BsgIB, M.BsII, M.BsmIA, M.BsmIB, M.BsmAI, M.BsmBI, M.BsoBI, M.Bsp6I, M.Bsp98I, M.BspCNIA, M.BspCNIB, M.BspHI, M.BspLU11IIIA, M.BspLU11IIIB, M.BspLU11IIIC, M.BspMIA, M.BspMIB, M.BspRI, M.BsrIA, M.BsrIB, M.BsrBIA, M.BsrBIB, M.BsrDIA, M.BsrDIB, M.BsrFI, M.BssHI, M.BssHII, M.BssSI, M.BstF5I, M.BstLVI, M.BstNBI, M.BstNBII, M.BstVI, M.BstYI, M.Bsu36I, M.Bsu168IP, M.Bsu168IIP, M.Bsu168IIIP, M.BsuBI, M.BsuFI, M.BsuRI, M.BusHemKP, M.BusHemK2P, M.Cac824I GCNGC, M.Cac824HemKP, M.Cac824ORF1222P, M.Cac824ORF2309P, M.Cac824ORF3358P, M.Cac824ORF3534AP, M.Cac824ORF3534BP, M.CauJHemKP, M.CauJORFC101P, M.CauJORFC102P, M.CauJORFC103P, M.CauJORFC104P, M.CauJORFC107P, M.CauJORFC110P, M.CauJORFC111P, M.CauJORFC112P, M.CauJORFC113P, M.CauJORFC114P, M.CauJORFC116P, M.CauJORFC117P, M.CauJORFC119P, M.CcrMI GANTC, M.CcrMHemKP, M.CcrMHemK2P, M.CcrMHemK3P, M.CcrMORF620P, M.CcrMORF1033P, M.CcrMORF3626P, M.Cdi630HemKP, M.Cdi630ORFC636P, M.Cdi630ORFC861P, M.Cdi630ORFC898P, M.Cdi630ORFC633aP, M.Cdi630ORFC633bP, M.CelHemKP, M.CeqI, M.Cfr9I, M.Cfr10I, M.CfrBI, M.CgII, M.ChuAHemKP, M.ChuAORFC123P, M.ChuAORFC127P, M.CjeI, M.CjeNHemKP, M.CjeNORF31P, M.CjeNORF208P, M.CjeNORF690P, M.CjeNORF1051P, M.CjeNORF1553P, M.CmuHemKP, M.CpaIOWAIP, M.CpnAHemKP, M.CpnHemKP, M.CpnJHemKP, M.CsyAIP, M.CsyBIP, M.CtrHemKP, M.CviAI, M.CviAII, M.CviAIIIP, M.CviAIV, M.CviAV, M.CviBI, M.CviBIII, M.CviJI, M.CviPI, M.CviQI, M.CviQIII, M.CviQVP, M.CviQVI, M.CviQVII, M.CviRI, M.CviSI, M.CviSII, M.CviSIII, M.CviSVIP, M.DcaI, M.DcaII, M.DdeI, M.DhaHemKP, M.DhaORFC135P, M.DhaORFC140P, M.DhaORFC141P, M.DhaORFC512P, M.DmeORFAP, M.DmeORFBP, M.DnoIP, M.DpnIIA, M.DpnIIB, M.DraIII, M.DraRHemKP, M.DraRORFB138P, M.DraRORFC20P, M.DreIP, M.DsaV, M.EaeI, M.EagI, M.EarIA, M.EarIB, M.EcaI, M.Ecl18kI, M.Eco31I, M.Eco47I, M.Eco47II, M.Eco56I, M.Eco57IA, M.Eco57IB, M.Eco72I, M.EcoAI, M.EcoBI, M.Eco67Dam, M.EcoEI, M.EcoHK31I, M.EcoKI, M.EcoKIIP, M.EcoK12AhemKP, M.EcoKDam, M.EcoKDcm, M.EcoKHemKP, M.EcoKO157DamP, M.EcoKO157DcmP, M.EcoKO157HemKP, M.EcoKO157HemK2P, M.EcoKO157HemK3P, M.EcoKO157ORF1196P, M.EcoKO157ORF1780P, M.EcoKO157ORF2981P, M.EcoKO157ORF4134P, M.EcoKO157ORF5307P, M.EcoNI, M.EcoN15ORF52P, M.EcoN15ORF58P, M.EcoO109I, M.EcoO157IP, M.EcoO157DamP, M.EcoO157DcmP, M.EcoO157HemKP, M.EcoO157HemK2P, M.EcoO157HemK3P, M.EcoO157HemK4P, M.EcoO157ORF1454P, M.EcoO157ORF2060P, M.EcoO157ORF2389P, M.EcoO157ORF3349P, M.EcoO157ORF4622P, M.EcoO157ORF5947P, M.EcoPI, M.EcoP15I, M.EcoP1Dam, M.EcoRI, M.EcoRII, M.EcoRV, M.EcoR9I, M.EcoR124I, M.EcoR124II, M.EcoT1Dam, M.EcoT2Dam, M.EcoT4Dam, M.EcoVIII, M.EcoVT2Dam, M.Eco933WdamP, M.Eco29kI, M.EcoprrI, M.EfaAHemKP, M.EfaAORFC149P, M.EfaAORFC151P, M.EfaAORFC154P, M.EfaORFAP, M.EfaORFC154P, M.EniIP, M.EsaBC1I, M.EsaBC2I, M.EsaBC3I, M.EsaBC4I, M.EsaBS1I, M.EsaBS2I, M.EsaDix1I, M.EsaDix2I, M.EsaDix3I, M.EsaDix4I, M.EsaDix5I, M.EsaDix6I, M.EsaDix7I, M.EsaLHCI, M.EsaLHCII, M.EsaLHCIII, M.EsaLHC2I, M.Esp3I, M.FacHemKP, M.FacHemK2P, M.FacORFC156P, M.FacORFC157AP, M.FacORFC157BP, M.FacORFC158P, M.FacORFC160P, M.FauI, M.FnuDI, M.Fnu4HI, M.FokI, M.FseI, M.FspI, M.Fsp7605IP, M.Fvi3I, M.GgaI, M.GshIP, M.GsuI, M.H2I, M.HaeII, M.HaeIII, M.HaeIV, M.HgaIA, M.HgaIB, M.HgiBI, M.HgiCI, M.HgiCII, M.HgiDI, M.HgiDII, M.HgiEI, M.HgiGI, M.HhaI, M.HhaII, M.HinHP1Dam, M.HinPII, M.HincII, M.HindI, M.HindII, M.HindIII, M.HindIV, M.HindV, M.HindHemKP, M.HindHemK2P, M.HindORF1056P, M.HindORF1286P, M.HinfI, M.HpaI, M.HpaII, M.HphIA, M.HphIB, M.HpyI, M.Hpy8I, M.Hpy9I, M.Hpy99II, M.Hpy99III, M.Hpy99IV, M.Hpy99VA, M.Hpy99VBP, M.Hpy99VI, M.Hpy99VII, M.Hpy99VIII, M.Hpy99IX, M.Hpy99X, M.Hpy99XI, M.Hpy166DP, M.Hpy166EP, M.Hpy166FP, M.Hpy166IVP, M.Hpy178IP, M.Hpy188I, M.Hpy188II, M.Hpy188III, M.HpyAI, M.HpyAIIA, M.HpyAIIB, M.HpyAIII, M.HpyAIV, M.HpyAV, M.HpyAVIA, M.HpyAVIB, M.HpyAVII, M.HpyAVIII, M.HpyAIX, M.HpyAX, M.HpyAXI, M.HpyAHemKP, M.HpyAORF263P, M.HpyAORF369P, M.HpyAORF463P, M.HpyAORF481P, M.HpyAORF483P, M.HpyAORF850P, M.HpyAORF1354P, M.HpyAORF1370P, M.HpyAORF1403P, M.HpyAORF1472P, M.HpyAORF1517P, M.HpyAORF1522P, M.HpyCH4IV, M.HpyCH4V, M.Hpy166GP, M.Hpy166HP, M.Hpy99HemKP, M.Hpy99ORF415P, M.Hpy99ORF430P, M.Hpy99ORF433P, M.Hpy99ORF613P, M.Hpy99ORF786P, M.Hpy99ORF846P, M.Hpy99ORF1012P, M.Hpy99ORF1284P, M.Hpy99ORF1296P, M.Hpy99ORF1365P, M.Hpy99ORF1409P, M.Hpy99ORF1411P, M.Hpy99ORF1423P, M.HsaIB, M.HsaIIP, M.HsaIIIA, M.HsaIIIB, M.HsaIVP, M.HsaHemKP, M.HsaHemK2P, M.HspNIP, M.HspNHemKP, M.HspNORF106P, M.HspNORF1543P, M.HspNORF2242P, M.HspNORF6135AP, M.HspNORF6135BP, M.KpnI, M.Kpn2I, M.KpnAI, M.LdvIP, M.LesIP, M.LinHemKIP, M.LlaI, M.Lla82I, M.Lla1403I, M.Lla2009IP, M.Lla2614I, M.LlaAIA, M.LlaAIB, M.LlaBI, M.LlaBIIP, M.LlaBIII, M.LlaCI, M.LlaDII, M.LlaDCHIA, M.LlaDCHIB, M.LlaFI, M.LlaGI, M.Lla1403HemKP, M.LlaKR2I, M.Lla509ORFAP, M.LlaPI, M.LldI, M.LmoA118I, M.Lsp1109I, M.MamI, M.MarMIP, M.MbaHemKP, M.MbaORFC198P, M.MbaORFC203P, M.MbaORFC206P, M.MbaORFC207P, M.MbaORFC531P, M.MbaORFC533P, M.MboIA, M.MboIB, M.MboIIA, M.MboIIB, M.MboAHemKP, M.MboAORFC210P, M.MboAORFC263P, M.MboAORFC271P, M.Mca27343I, M.MfeI, M.MgeHemKP, M.MgeORF184P, M.MgrIP, M.MjaI, M.MjaII, M.MjaIII, M.MjaIVP, M.MjaV, M.MjaVI, M.MjaHemKP, M.MjaORF132P, M.MjaORF563P, M.MjaORF1200P, M.MjaORF1220P, M.MjaORFCL42P, M.MleHemKAP, M.MleHemKBP, M.MleSHemKP, M.MleSORF756P, M.MloI lemKP, M.MloORFmll9056P, M.MloORFmll9333P, M.MloORFmlr7520P, M.MloORFmlr7992P, M.MloORFmlr8517P, M.MluI, M.MlyI, M.MmaMHemKP, M.MmaMHemK2P, M.MmaMHemK3P, M.MmaMORF527P, M.MmaMORFC170P, M.MmaMORFC174P, M.MmaMORFC175AP, M.MmaMORFC175BP, M.MmaMORFC525P, M.MmaMORFC527P, M.MmuI, M.MmuIIP, M.MmuIIA, M.MmuIIB, M.MmyIP, M.MneAORF1590P, M.MnIIA, M.MnIIB, M.MpnIP, M.MpnHemKP, M.MpnORFDP, M.MpuCHemKP, M.MpuCORF430AP, M.MpuCORF430BP, M.MpuCORF810AP, M.MpuCORF810BP, M.MpuCORF1850AP, M.MpuCORF1850BP, M.MpuCORF3960P, M.MpuCORF3970P, M.MpuCORF3980P, M.MpuCORF4330P, M.MpuCORF4800P, M.MpuCORF6780P, M.MpuCORF6880P, M.MpuUI, M.MsaRVIP, M.MsaV2IP, M.MsaV3IP, M.MsaV4IP, M.MseI, M.MspI, M.MspA1I, M.MspMCHemKP, M.MspMCHemK2P, M.MspMCHemK3P, M.MspMCORFC183P, M.MspMCORFC184P, M.MspMCORFC186P, M.MspMCORFC187AP, M.MspMCORFC187BP, M.MthHHemKP, M.MthHORF495P, M.MthHORF724P, M.MthHORF942P, M.MthTI, M.MthZI, M.MtuCTHemKP, M.MtuCTORF2076P, M.MtuCTORF2082P, M.MtuCTORF2826P, M.MtuCTORF3363P, M.MtuHHemKP, M.MtuHORF2756P, M.MtuHORF3263P, M.MunI, M.MvaI, M.MwoI, M.NaeI, M.NarAORFC306P, M.NcoI, M.NcrNI, M.NdeI, M.NeuHemKP, M.NeuORFC215AP, M.NeuORFC215BP, M.NeuORFC218P, M.NeuORFC219P, M.NgoBI, M.NgoBIIP, M.NgoBV, M.NgoBVIIA, M.NgoBVIIIB, M.NgoFVII, M.NgoLII, M.NgoLHemKP, M.NgoMIV, M.NgoMX, M.NgoMXV, M.NgoMorf2P, M.NgoPII, M.NgoSII, M.Ngo125VIIP, M.NheI, M.NlaIII, M.NlaIV, M.NlaX, M.NmeAHemKP, M.NmeAHemK2P, M.NmeAORF59P, M.NmeAORF191P, M.NmeAORF427P, M.NmeAORF532P, M.NmeAORF561P, M.NmeAORF1035P, M.NmeAORF1038P, M.NmeAORF1385P, M.NmeAORF1432P, M.NmeAORF1453P, M.NmeAORF1467P, M.NmeAORF1500P, M.NmeAORF1590P, M.NmeBIA, M.NmeBIB, M.NmeBF13P, M.NmeBHemKP, M.NmeBHemK2P, M.NmeBORF76P, M.NmeBORF826P, M.NmeBORF829P, NmeBORF1033P, M.NmeBORF1223P, M.NmeBORF1261P, M.NmeBORF1290P, M.NmeBORF1375P, M.NmeB1940ORF1P, M.NmeDIP, M.Nme212ORF1P, M.NmeSI, M.NmeST1117ORF1P, M.NotI, M.NpuHemKP, M.NpuORFC221P, M.NpuORFC222P, M.NpuORFC224P, M.NpuORFC226P, M.NpuORFC227P, M.NpuORFC228P, M.NpuORFC229P, M.NpuORFC230P, M.NpuORFC231P, M.NpuORFC232P, M.NpuORFC234P, M.NpuORFC237P, M.NpuORFC242P, M.NspI, M.NspIII, M.NspV, M.NspHI, M.OkrAI, M.OsaIP, M.PabHemKP, M.PabORF588P, M.PabORF1205P, M.PabORF1283P, M.PabORF2149P, M.PabORF2246P, M.PabORF2317P, M.Pac25I, M.PaePAHemKP, M.PaePAHemK2P, M.PaePAHemK3P, M.PaePAHemK4P, M.PaePAORF370P, M.PaePAORF2735P, M.PaeR7I, M.PcopB4P, M.PflMI, M.PflPHemKP, M.PflPHemK2P, M.PflPHemK3P, M.PflPHemK4P, M.PfuAIP, M.PgiI, M.PhaAI, M.PhaBI, M.PhiBssHII, M.PhiCh1I, M.PhiGIP, M.PhiHIAP, M.PhiHIBP, M.PhiHII, M.PhiMx81, M.Phi3TI, M.Phi3TII TCGA, M.PhoHemKP, M.PhoORF39P, M.PhoORF338P, M.PhoORF584P, M.PhoORF905P, M.PhoORF1032P, M.PhoORF1948P, M.PleI, M.PliMCI, M.PmaMEDHemKP, M.PmuDamP, M.PmuHemKP, M.PmuHemK2P, M.PmuHemK3P, M.PmuORF698P, M.PmuORF1537P, M.Ppu21I, M.ProHemKP, M.ProORFC262P, M.PsaI, M.PshAI, M.PspGI, M.PspPI, M.PstI, M.PstII, M.PvuII, M.QpaIP, M.RcoHemKP, M.RcoORFC690P, M.RcoORF1350P, M.RhmIP, M.Rho11sI, M.RhyI, M.Rle39BI, M.RmeADamP, M.RmeAHemKP, M.RmeAHemK2P, M.RmeAORFC243P, M.RmeAORFC246P, M.RnoIP, M.RpaORFC296AP, M.RpaORFC296BP, M.RpaORFC298P, M.RpaORFC302P, M.RpaORFC303P, M.RprHemKP, M.RsaI, M.RshYP, M.RshXP, M.RspAIP, M.RspDORFC282AP, M.RspDORFC282BP, M.RspDORFC283P, M.RspDORFC285P, M.RspDORFC291P, M.RsrI, M.SPBetaI, M.SPRI, M.SacI, M.SacII, M.SalI, M.SapIA, M.SapIB, M.Sau421, M.Sau961, M.Sau3AI, M.SauMu50HemKP, M.SauMu50ORF431P, M.SauMu50ORF1808P, M.SauN315HemKP, M.SauN315ORF391P, M.SauN315ORF1626P, M.ScaI, M.SceHemKP, M.SciSpV1P, M.ScoA3HemKP, M.ScrFIA, M.ScrFIB, M.SenPI, M.SeqHemKP, M.SeqORFC20AP, M.SeqORFC20BP, M.SeqORFC57P, M.SeqORFC175P, M.SeqORFC272P, M.SeqORFC395P, M.SeqORFC448P, M.SfiI, M.SfoI, M.SgrAI, M.SinI, M.SmaI, M.SmaII, M.SmeIP, M.SmeHemK1P, M.SmeHemK2P, M.SmeORF2296P, M.SmeORF3763P, M.SnaBI, M.SobIP, M.SpeI, M.SphI, M.Spn526IP, M.Spn5252IP, M.SpnHemKP, M.SpnORF505P, M.SpnORF886P, M.SpnORF122IP, M.SpnORF1336P, M.SpnORF1431P, M.SpnRHemKP, M.SpnRHemK2P, M.SpnRORF449P, M.SpnRORF790P, M.SpnRORF1101P, M.SpnRORF1287P, M.SpnRORF1665P, M.SpomI, M.SpomHemKP, M.SprHemKP, M.SpyHemKP, M.SpyORF1077P, M.SpyORF1906P, M.Sse9I, M.SsfORF265P, M.SsoI, M.SsoII, M.SspI, M.Ssp6803I, M.Ssp6803HemKP, M.Ssp6803ORF729P, M.Ssp6803ORF1803P, M.SssI, M.Ssu2479IA, M.Ssu2479IB, M.Ssu4109IA, M.Ssu4109IB, M.Ssu4961IA, M.Ssu4961IB, M.Ssu8074IA, M.Ssu8074IB, M.Ssu11318IAP, M.Ssu11318IBP, M.SsuDAT1IA, M.SsuDAT1IB, M.Sth368I, M.SthER35IP, M.SthSfi1ORF535P, M.SthSt0IP, M.SthSt8IP, M.StoHemKP, M.StoORF335P, M.StsI, M.StyCORFAP, M.StyD4I, M.StyDam, M.StyDcmIP, M.StyLTI, M.StyLTIII, M.StyLT2DamP GATC, M.StyLT2DcmP, M.StyLT2FelsDamP, M.StyLTHemKP, M.StyLT2HemKP, M.StyLT2HemK2P, M.StyLT2ORF357P, M.StyLT2ORF3386P, M.StyLT2ORF4525P, M.StyR27ORF41P, M.StyR27ORF43P, M.StyR27ORF154P, M.StySBLI, M.StySBLIIP, M.StySJI, M.StySKI, M.StySPI, M.SwaI, M.TaqI TCGA, M.TfiI GAWTC, M.TfuORFC321AP, M.TfuORFC321 BP, M.TfuORFC325P, M.TfuORFC327P, M.ThaI, M.ThaHemKP, M.ThaHemK2P, M.ThaORF318P, M.ThaORF644P, M.ThaORF1168P, M.ThaORF1336AP, M.ThaORF1336BP, M.ThaORF1417P, M.TliI, M.TmaI, M.TmaHemKP, M.TpaI, M.TpaHemKP, M.TseI, M.Tsp45I, M.Tsp509I, M.TspRI, M.Tth111I, M.TthHB8I, M.TvoORF124AP, M.TvoORF124BP, M.TvoORF442P, M.TvoORF681P, M.TvoORF725P, M.TvoORF849P, M.TvoORF1192P, M.TvoORF1400P, M.TvoORF1413P, M.TvoORF1416P, M.TvoORF1436P, M.UurHemKP, M.UurORF98P, M.UurORF100P, M.UurORF477P, M.UurORF528P, M.Van9II, M.Vch01IP, M.VchADamP, M.VchAHemKP, M.VchAHemK2P, M.VchAORF198P, M.VchAORF1769P, M.VspI, M.XamI, M.XbaI, M.XcmI, M.XcyI, M.XfaAORFC332P, M.XfaAORFC333P, M.XfaAORFC340P, M.XfaHemKP, M.XfaHemK2P, M.XfaORF297P, M.XfaORF641P, M.XfaORF935P, M.XfaORF1774P, M.XfaORF1804P, M.XfaORF1968P, M.XfaORF2297P, M.XfaORF2313P, M.XfaORF2723P, M.XfaORF2724P, M.XfaORF2728P, M.XfaORF2742P, M.XhoI, M.XhoII, M.XlaI, M.XmaI, M.XmaXhI, M.XmnI, M.XorII, M.YpeIP, M.ZmaI, M.ZmaIIA, M.ZmaIII, M.ZmaV, and M.ZmaORFAP. The "Achilles' Heel" protocol could also be used (See, e.g., Ferrin and Camerini-Otero, Science 254: 1494–1497 [1991]).

An oligonucleotide:target double D-loop can also be used to generate a specific cleavage site in double-stranded target DNA. The Type IIs restriction endonucleases are also particularly useful in the methods of the invention. Type IIs restriction enzymes have distinct DNA binding and cleavage domains; therefore, they recognize a specific sequence but cleave a defined distance away. For example, the Type IIs restriction enzyme, FokI, binds to a site containing the sequence GGATG and cleaves 9 and 13 base pairs away from the recognition site in a staggered fashion. Other Type IIs and Type IIs-like enzymes can be used including, for example, restriction enzyme StsI, Group I intron homing endonuclease I-TevI, R2 retrotransposon endonuclease R2, P1 transposase SCEI and bacterial recombination RecBCD. Other homing endonucleases include, for example, F-SceI, F-SceII, F-SuvI, F-TevI, F-TevII, I-AmaI, I-AniI, I-BmoI, I-CeuI, I-CeuAIIP, I-ChuI, I-CmoeI, I-CpaI, I-CpaII, I-CreI, I-CrepsbIP, I-CrepsbIIP, I-CrepsbIIIP, I-CrepsbIVP, I-CsmI, I-CvuI, I-CvuAIP, I-DdiI, I-DdiII, I-DirI, I-DmoI, I-HmuI, I-HmuII, I-HspNIP, I-LlaI, I-MsoI, I-NaaI, I-NanI, I-NcIIIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PpbIP, I-PpoI, I-SPBetaIP, I-ScaI, I-SceI, I-SceII, I-SceIII, I-SceIV, I-SceV, I-SceVI, I-SceVII, I-SexIP, I-SneIP, I-SpomCP, I-SpomIP, I-SpomIIP, I-SquIP, I-Ssp6803I, I-SthPhIJP, I-SthPhIST3P, I-SthPIS3bP, I-deIP, I-TevI, I-TevII, I-TevIII, I-UarAP, I-UarHGPA1P, I-UarHGPA13P, I-VinIP, I-ZbiIP, PI-MgaI, PI-MtuI, PI-MtuHIP, PI-MtuHIIP, PI-PfuI, PI-PfuII, PI-PkoI, PI-PkoII, PI-PspI, PI-Rma43812IP, PI-SP-BetaIP, PI-SceI, PI-TfuI, PI-TfuII, PI-ThyI, PI-TliI, and PI-TliII. Also Type IIB restriction enzymes that cleave on both sides of the binding site could be used such as BcgI and BplI. The recognition site for a Type IIs, Type IIs-like or Type IIB restriction enzyme can be formed by, for example, an extension on one of the oligonucleotides in the double D-loop which folds back forming a double-stranded portion containing the recognition site. Alternatively, the recognition site can be formed by homologous extensions on both oligonucleotides in the double D-loop which hybridize to form the recognition site for a Type IIs, Type IIs-like or Type IIB restriction enzyme. Cleavage occurs in the target duplex 5' to the complex.

Alternately, a cleavage domain or peptide having endonucleolytic activity that is not sequence specific can linked to one of the oligonucleotides in the double D-loop. Examples of such an endonucleolytic activity include, for example, EDTA-FeII (for iron/EDTA facilitated cleavage), non-specific phosphodiesterases, and non-specific restriction endonucleases. For example, a cleavage domain or peptide having endonucleolytic can be linked covalently to one of the oligonucleotides in the double D-loop or it can be linked to an oligonucleotide through a ligand-receptor interaction. The double D-loop directs cleavage to the specific site where the double D-loop is formed because the cleavage domain is either linked directly to one of the oligonucleotides or binds the ligand attached to the oligonucleotide. As a further example, the double D-loop structure may be cleaved with a single-strand specific endonuclease, for example, S1 nuclease. As yet another example, the cleavage can be accomplished using a resolvase that recognizes the double D-loop structure, such as the MRE11. In any of these cases, the site of cleavage specificity is conferred by the target sequence which is defined by the oligonucleotides. Several approaches described above for blocking cleavage of a restriction site can also be used to generate a specific cleavage site, including, for example, the "Achilles' Heel" protocol or forming a double D-loop and incubating with an enzyme to add/remove methyl groups as described, depending on the sensitivity of a selected enzyme to the presence of methyl groups.

Both the restriction site protection method and the site specific cleavage method are useful in restriction fragment length polymorphism analysis.

The incoming oligonucleotides used in the methods of the present invention may be about 10 to about 500 nucleotides in length, usefully about 15 to about 50 nucleotides in length, and generally about 20 to 40 nucleotides in length. In some embodiments, the incoming oligonucleotide is a DNA oligonucleotide or a DNA oligonucleotide with modified terminal segments. The incoming oligonucleotide comprises enough DNA residues to allow sufficient RecA to bind to promote annealing between the incoming oligonucleotide and the target duplex nucleic acid molecule. In another embodiment, the incoming oligonucleotide is at least as long as the annealing oligonucleotide.

The annealing oligonucleotide used in the methods of the present invention may be about 5–50 nucleotides in length, usefully about 10–30 nucleotides in length, and generally about 12–20 nucleotides in length. In one embodiment, the annealing oligonucleotide comprises at least one LNA, RNA, or PNA or any combination thereof. In another embodiment the annealing oligonucleotide comprises more than 10, 20, 30, 40, 50, 60, 70, 80, or 90% LNA, RNA, or PNA. In a particularly useful embodiment, the annealing oligonucleotide comprises enough LNA, RNA, or PNA such that RecA does not bind to a significant extent to the annealing oligonucleotide. In some embodiments, the incoming oligonucleotide is centrally positioned relative to the annealing oligonucleotide.

If there are self-dimerization structures within the oligonucleotide, lengths longer than about 35 bases are preferred for both oligonucleotides. Oligonucleotides that are both shorter and longer than certain of the exemplified oligonucleotide described in the examples herein are useful for the methods of the invention and are within the scope of the present invention.

Once an oligomer is chosen, it can be tested for its tendency to self-dimerize. Checking for self-dimerization tendency can be accomplished manually or, more easily, by using a software program. One such program is Oligo Analyzer 2.0, available through Integrated DNA Technologies (Coralville, Iowa 52241) (http://www.idtdna.com); this program is available for use on the world wide web at http://www.idtdna.com/program/oligoanalyzer/oligoanalyzer.asp.

For each oligonucleotide sequence input into the program, Oligo Analyzer 2.0 reports possible self-dimerized duplex forms, which are usually only partially duplexed, along with the free energy change associated with such self-dimerization. Delta G-values that are negative and large in magnitude, indicating strong self-dimerization potential, are automatically flagged by the software as "bad". Another software program that analyzes oligomers for pair dimer formation is Primer Select from DNASTAR, Inc., 1228 S. Park St., Madison, Wis. 53715, Phone: (608) 258-7420 (http://www.dnastar.com/products/PrimerSelect.html).

If the sequence is subject to significant self-dimerization, the addition of further sequence complementarity to the target nucleic acid can improve the utility of the oligonucleotide for the methods of the invention. The optimal lengths, complementarity and composition of the oligonucleotides for a given target nucleic acid sequence can be determined by the assays described herein.

The oligonucleotides used in the present invention are substantially complementary to one strand of a duplex target nucleic acid molecule. Generally, the oligonucleotides of the present invention are at least 80% identical in sequence to one strand of a duplex target nucleic acid molecule, typically at least 90% identical in sequence to a target nucleic acid, and more typically at least 95% identical in sequence to a target nucleic acid. In most applications, the oligonucleotides of the present invention are identical in sequence to a target nucleic acid or have a single mismatch relative to the sequence of the target. Where the oligonucleotides are not identical in sequence to the target nucleic acid sequence any differences in sequence of the oligonucleotide as compared to the targeted nucleic acid are generally located at about the middle of the oligonucleotide sequence.

The double-stranded probe:duplex target complexes of the present invention can also be used for diagnostic in situ detection techniques.

In another aspect, the invention relates to a method for detecting a polymorphism, including a single nucleotide polymorphism ("SNP"), in a target sequence. A polymorphism refers to the existence of two or more alternative sequences which can be, for example, different allelic forms of a gene. A polymorphism may comprise one or more base changes including, for example, an insertion, a repeat, or a deletion.

SNPs usually refer to polymorphisms that are the result of a single nucleotide alteration. SNPs usually arise due to a difference of one nucleotide at the polymorphic site but can also arise from the deletion or insertion of a nucleotide relative to a reference allele. A target duplex nucleic acid molecule analyzed by the method for detecting a polymorphism, including a SNP, can be amplified, for example by PCR, or unamplified. Further, the target nucleic acid molecule can be analyzed in vitro, either in solution or affixed to a solid matrix, or in situ.

In one useful embodiment, the incoming oligonucleotide is labeled with a detectable moiety. In another useful embodiment the annealing oligonucleotide is labeled with a detectable moiety. In some embodiments, both the incoming and the annealing oligonucleotides are labeled with a detectable moiety. When both oligonucleotides are so labeled, the labels may be the same or different.

In another useful embodiment, the method of the invention is used to screen an individual to determine the genotype at a specific SNP. Genetic factors contribute to many human diseases, conferring susceptibility or resistance and affecting both progression and severity of the disease. Many of these genetic factors are associated with particular alleles of specific genes that are represented by SNPs. For example, variations in the apoE gene are associated with Alzheimer's disease, variations in the CCR5 chemokine receptor gene are associated with resistance to HIV infection, and variations in the hemoglobin gene are associated with sickle cell anemia. Further, response to specific therapies may also be affected by genetic differences. Thus, information about variations in DNA sequence may assist in the analysis of disease and in the development of diagnostic, therapeutic, and preventative strategies. Thus, the ability to identify the specific genetic constitution of an individual will aid in the diagnosis, treatment, and prevention of disease.

The following examples are provided by way of illustration only, and are not intended to limit the scope of the invention disclosed herein.

EXAMPLE 1

General Protocols for Formation and Detection of Double D-Loops and Y-Arms

Formation of double D-loops. Typically, we form double D-loops or Y-arms by combining the following in a 7 µl reaction so that the final concentration in 10 µl is: 80 nM of the first or "incoming" oligonucleotide; 2.5 µM *Escherichia coli* RecA protein; 1.0 mM ATP-γ-S; 25 mM Tris-acetate, pH 6.8; 1 mM dithiothreitol; and 1 mM magnesium acetate. This reaction is incubated for 10 minutes at 37° C. to allow for binding of RecA protein to the oligonucleotide ("presynapsis", see FIG. 1 for an outline of the method). We then add double-stranded nucleic acid target, which is generally $^{32}$P-end-labeled using T4 polynucleotide kinase to facilitate detection of the complex, at a concentration of approximately 20 nM and 10 mM magnesium acetate to a final volume of 10 µl. We incubate this reaction for 10 minutes at 37° C. to allow for synapsis between to the incoming oligonucleotide and the target nucleic acid molecule. We then add the second or "annealing" oligonucleotide in 1 µl to a concentration of 640 nM (calculated for the original 10

μl reaction volume) and incubate for 10 minutes at 37° C. to allow the second oligonucleotide to anneal to the target nucleic acid. We then denature the RecA bound to the oligonucleotide:target complex by cooling the reaction to about 4° C. in an ice bath and adding 1 μl of 10% SDS. The samples are then used immediately or stored at −20° C.

Detection of double D-loops. We may analyze the samples prepared as described above by separating by polyacrylamide gel electrophoresis (PAGE). We dry the gels and detect the $^{32}$P-labeled target duplex nucleic acid by either autoradiography or using a phosphorimager. We monitor the formation of the double D-loops under these assay conditions by detecting the retarded migration of the labeled nucleic acid in the gel: the labeled target nucleic acid in double D-loops migrates more slowly than duplex target nucleic acid.

EXAMPLE 2

Double D-loop Formation Using an Oligonucleotide Comprising LNA

Oligonucleotides used in this example. We employ the protocol described in Example 1 to form double D-loops between two DNA oligonucleotides and linear, duplex target DNA. The target duplex DNA is composed of two linear 70-mer oligonucleotides with sequence complementary to each other. The sequence of the first target strand, designated "OligoA", is: 5'-CTCCGGCCGCTTGGGTGGAG AGGCTATTCGGCTA CGACTGGGCACAACAGACAATCGGCTGCTCTGAT-GC-3' (SEQ ID NO: 1) and the sequence of the second target strand, designated "OligoB", is: 3'-GAGGCCGGCGAAC-CCACCTCTCCGATAAGCCGAT GCTGACCCGTGTTGTCTGTTAGCCGACGAGACTA-CG-5' (SEQ ID NO: 2). The nucleotide which is approximately at the center of the target sequence is indicated in underlined to allow for easy identification of the complementary sequence of subsequent DNA oligonucleotides. The first or incoming oligonucleotide, designated "OligoC", is a 30-mer with the following sequence: 5'-AGGCTATTCG-GCTACGACTGGGCACAACAG-3' (SEQ ID NO: 3) which is complementary to OligoB. The second or annealing oligonucleotide, designated "OligoI", is a 25-mer with the following sequence: 5'-TTGTGCCCAGTC GTAGCCGAATAGC-3' (SEQ ID NO: 4) which is complementary to OligoA. In certain experiments, we use in place of OligoI as the annealing oligonucleotide the following 15-mer LNA oligonucleotide, designated "OligoN": 5'-GC-CCAGTCGTAGCCG-3' (SEQ ID NO: 5).

To test the formation of Y-arms under our assay conditions, we use a different target duplex DNA composed of two linear 67-mer oligonucleotides with sequence complementary to each other. The sequence of the first target strand, designated "OligoT", is: 5'-ACAACTGTGTTCACTAG-CAACCTCAAACAGACACCATGGTGCAC-CTGACTCCTGAGGAGAAGTCTGC-3' (SEQ ID NO: 6) and the sequence of the second target strand, designated "OligoU", is: 3'-TGTTGACACAAGTGATCGTTG-GAGTTTGTCTGTGGTACCACGTGGACT-GAGGACTCCTCTTCAGACG-5' (SEQ ID NO: 7). We use two oligonucleotides complementary to the end of the OligoT/OligoU linear target duplex in these Y-arm experiments. The first or incoming oligonucleotide, designated "OligoX", is a 30-mer with the following sequence: 5'-GCAGACTTCTCCTCAGGAGTCAGGTGCACC-3' (SEQ ID NO: 8) which is complementary to the end of the OligoT strand of the target duplex. The second or annealing oligonucleotide, designated "Oligo5", is a 30-mer with the following sequence: 5'-GTTGCACCTGACTCCTGAG-GAGAAGTCTGC-3' (SEQ ID NO: 9) which is complementary to OligoU.

Figure 2:
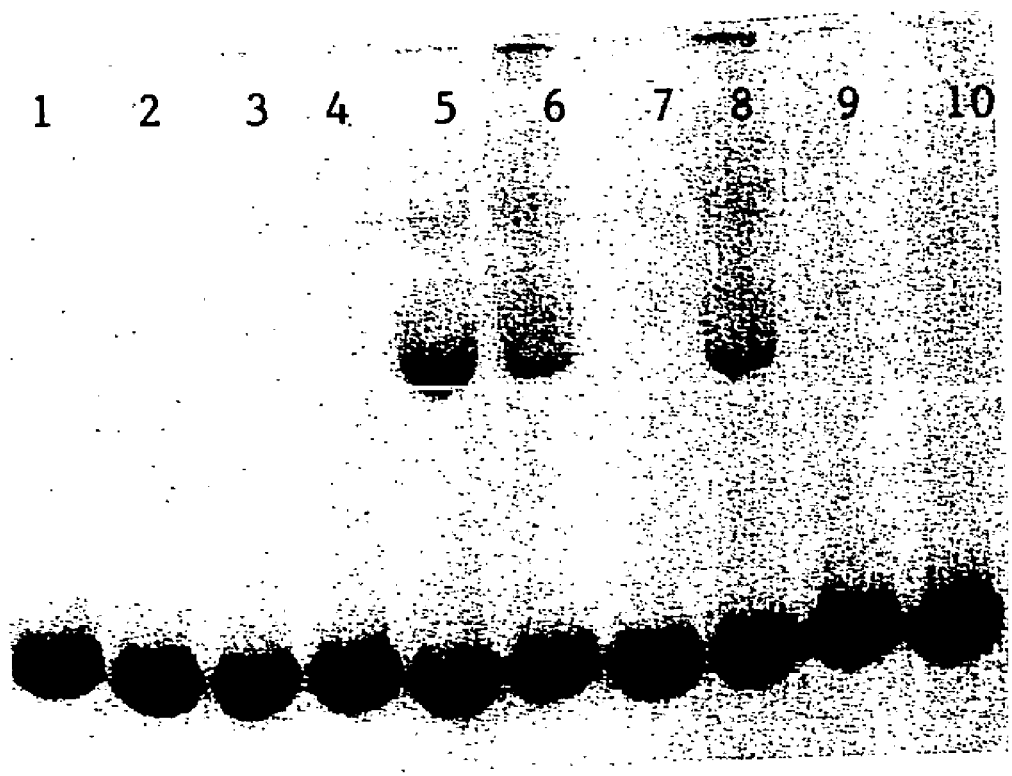
FIG. 2. Conditions for formation of double D-loops using two DNA oligonucleotides. OligoA/OligoB target was mixed with OligoC incoming and with OligoI annealing under a variety of conditions: 1) target only; 2) no annealing oligonucleotide; 3) deproteinize at 37° C. while adding annealing oligonucleotide; 4) deproteinize at 4° C. while adding annealing oligonucleotide; 5) standard protocol in Example 1 except deproteinization at 37° C.; 6) standard protocol; 7) adding a second addition of excess incoming oligonucleotide prior to addition of annealing oligonucleotide; 8) adding a second addition of excess incoming oligonucleotide after addition of annealing oligonucleotide; 9) both oligonucleotides added simultaneously after incubating together with RecA; 10) both oligonucleotides added simultaneously after incubating separately with RecA.

Annealing oligonucleotide and RecA are required for formation of double D-loops. We demonstrate that both the annealing oligonucleotide and a recombination protein are required by following the protocol as described in Example 1 but omitting certain reagents or steps. The results of these experiments are shown in FIG. 2 (using OligoA/OligoB target and OligoC/OligoI), FIG. 3 (using OligoA/Oligo B target and OligoC/OligoN) and FIG. 4 (using OligoT/OligoU target and OligoX/Oligo5).

In a control experiment shown in lane 1 of these Figures, omitting both oligonucleotides leads to no complex formation. Similarly, when we deproteinize the complex after the addition of the incoming oligonucleotide and omit the annealing oligonucleotide, we do not observe any stable complexes (lane 2). This confirms that single D-loops containing DNA oligonucleotides are unstable after deproteinization.

Finally, as shown in lanes 3 and 4 of these figures, when we deproteinize the complexes while adding the annealing oligonucleotide, we observe no double D-loop formation. This was observed regardless of whether the annealing step was carried out at 37° C. (lane 3) or 4° C. (lane 4). These results indicate that the single D-loop must remain stabilized by the recombination protein for the annealing oligonucleotide to be incorporated into the structure.

To confirm this result, we perform a competition experiment where we add an excess of incoming oligonucleotide after the formation of the single D-loop and before the addition of the annealing oligonucleotide. As shown in lane 7 of FIGS. 2, 3 and 4, the addition of excess incoming oligonucleotide that has not been coated with RecA abolishes formation of double D-loops where the target sequence is in the middle of the linear duplex (FIGS. 2 and 3) and dramatically reduces the formation of Y-arms (FIG. 4). By sequestering the annealing oligonucleotide in a hybrid with the complementary incoming oligonucleotide, formation of a double D-loop is inhibited.

However, if the double D-loop or Y-arm structure is formed first by adding annealing oligonucleotide before the addition of excess free incoming oligonucleotide there is essentially no impairment of double D-loop formation. This result comfirms that the annealing oligonucleotide is incorporated into the double D-loop prior to deproteinization of the complex.

Oligonucleotides comprising LNA form double D-loops more efficiently. The results shown in FIG. 2 (using OligoA/OligoB target and OligoC/OligoI), FIG. 3 (using OligoA/Oligo B target and OligoC/OligoN) and FIG. 4 (using OligoT/OligoU target and OligoX/Oligo5) lanes 5 and 6 demonstrate that using an oligonucleotide comprising LNA results in much greater double D-loop formation than when oligonucleotides containing only DNA residues are used. We observe this result both when we perform the deproteinization step, i.e. addition of SDS, at 4° C. as in the standard protocol described in Example 1 (lane 6) or when we perform deproteinization at 37° C. (lane 5). In addition, comparison of the results shown in FIG. 3, lanes 5 and 6 to the results shown in FIG. 2, lanes 5 and 6 also clearly shows that the use of an oligonucleotide comprising LNA results in much greater formation of double D-loops than when oligonucleotides containing only DNA residues are used.

Oligonucleotides comprising LNA can form double D-loops in a single-step reaction. If incoming and annealing oligonucleotides are added simultaneously to the target duplex, double D-loop formation is severely impaired or absent. We demonstrate this using DNA oligonucleotides (OligoC/OligoI with OligoA/OligoB target) as shown in FIG. 2, lane 9 and lane 10. For these experiments we follow the protocol outlined in Experiment 1, except that we coat both oligonucleotides with RecA and then simultaneously add them in equimolar amounts to the target nucleic acid. In FIG. 2, lane 9 the oligonucleotides are combined and coated with RecA together before adding them to the target nucleic acid and in FIG. 2, lane 10 the oligonucleotides are first separately coated with RecA and then added together to the target nucleic acid. As shown in FIG. 4, lane 9 and lane 10, simultaneous addition of two DNA oligonucleotides also fails to support the formation of Y-arms.

Figure 3:
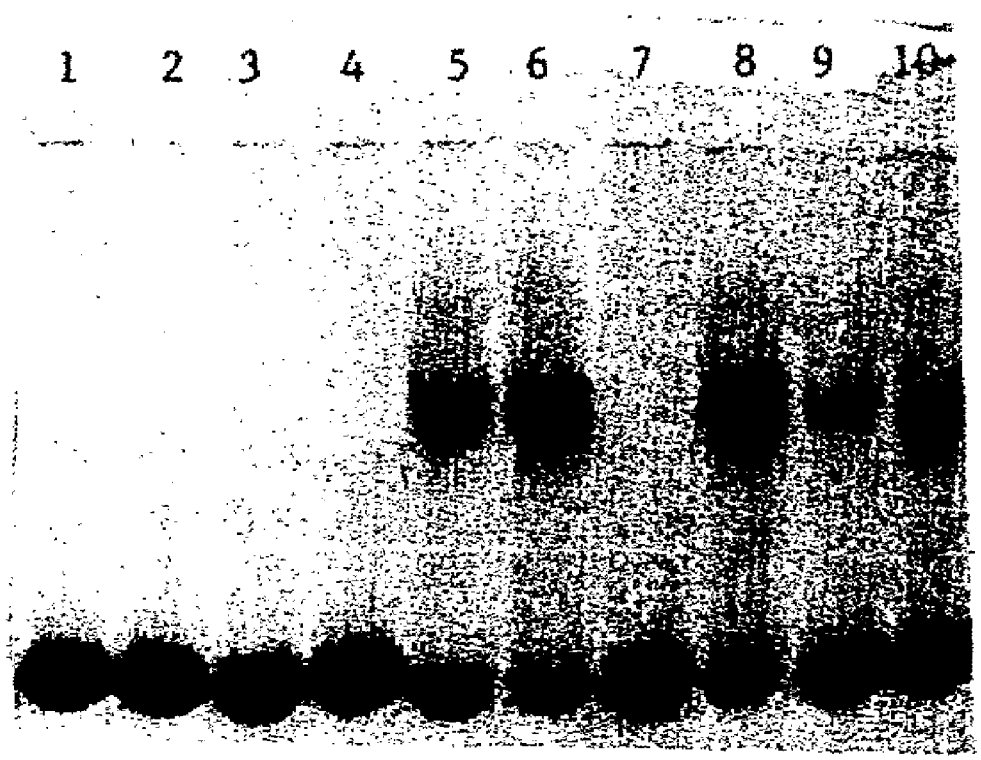
FIG. 3. Conditions for formation of double D-loops using an LNA oligonucleotide. OligoA/OligoB target was mixed OligoC incoming and OligoN annealing under a variety of conditions (lanes as indicated in FIG. 2).
Figure 4:
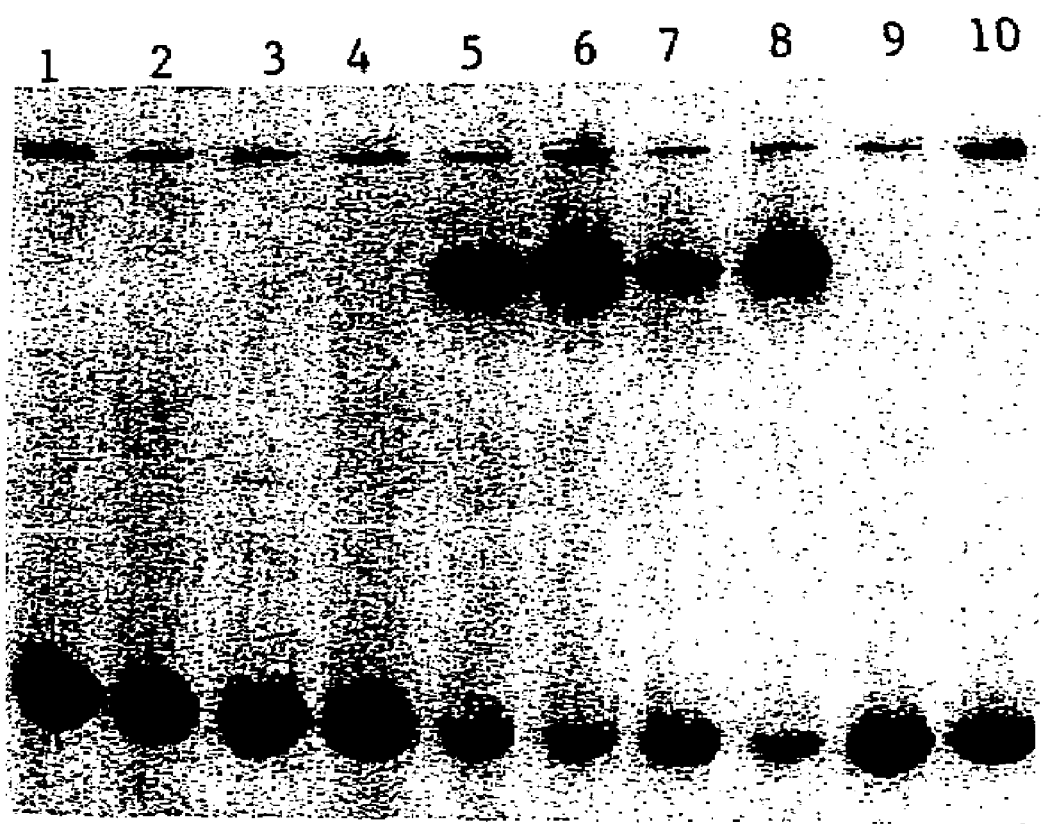
FIG. 4. Conditions for formation of Y-arms using two DNA oligonucleotides. OligoT/OligoU target was mixed with OligoX incoming and with Oligo5 annealing under a variety of conditions (lanes as indicated in FIG. 2).

However, as shown in FIG. 3, lane 9 and lane 10, simultaneous addition of two oligonucleotides where one of the oligonucleotides is composed of LNA residues results in surprisingly significant formation of double D-loops. The extent of double D-loop formation is greater when the oligonucleotides were separately coated with RecA before addition to the target nucleic acid (lane 10) than when they are mixed together before coating with RecA (lane 9).

EXAMPLE 3

Figure 5:
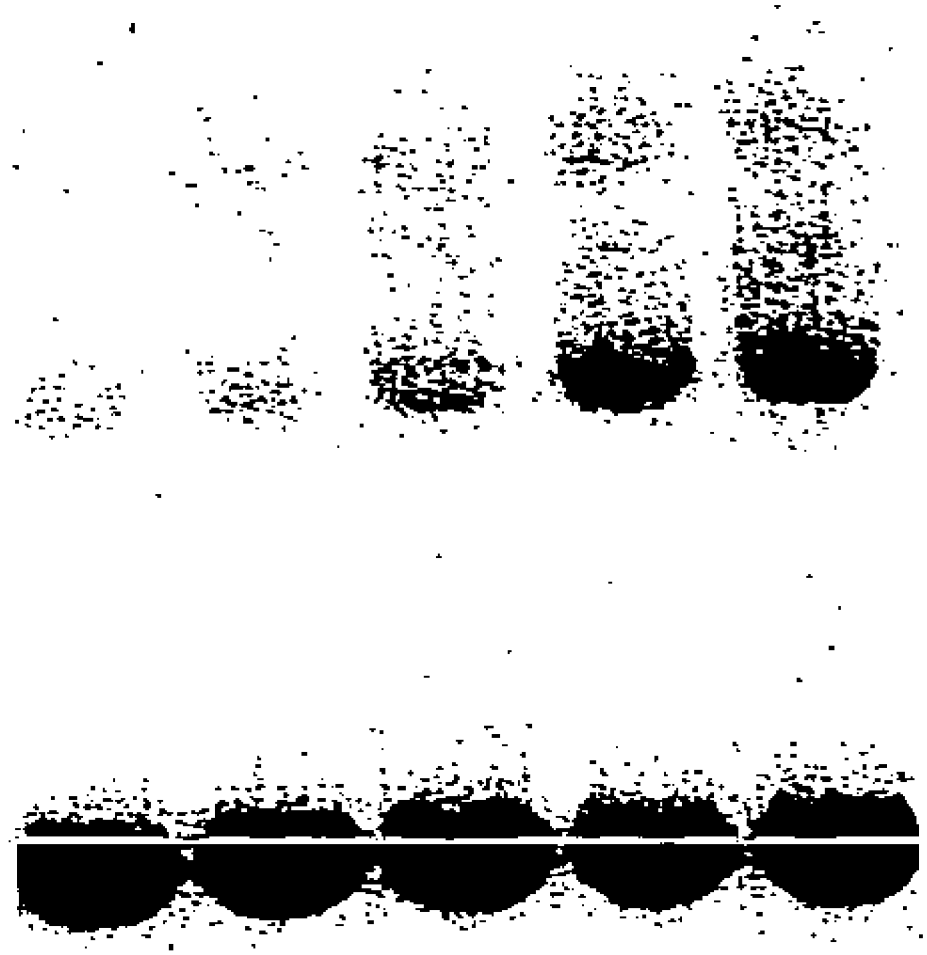
FIG. 5. Optimal annealing temperature for double D-loop formation. Double D-loop formation using OligoA/OligoB as target, OligoC as incoming and OligoI as annealing oligonucleotide over a range of temperatures (in ° C.) as indicated.

Determination of Optimal Temperature and Annealing Times for Formation of Double D-Loops Determination of optimal annealing temperature. We test the formation of double D-loops using the OligoA/OligoB duplex as the target, OligoC as the incoming oligonucleotide and OligoI as the annealing oligonucleotide (target sequence and oligonucleotides as described in Example 2). We follow the protocol described in Example 1, except we vary the temperature at which the reaction is incubated after the addition of the annealing oligonucleotide. As shown in FIG. 5, we test incubation at 4° C., 15° C., 25° C., 37° C. and 45° C. We observe increased formation of the double D-loop as we increase the temperature up to approximately 37° C. The extent of double D-loop formation at 37° C. is approximately equal to the extent of double D-loop formation at 45° C.

Figure 6:
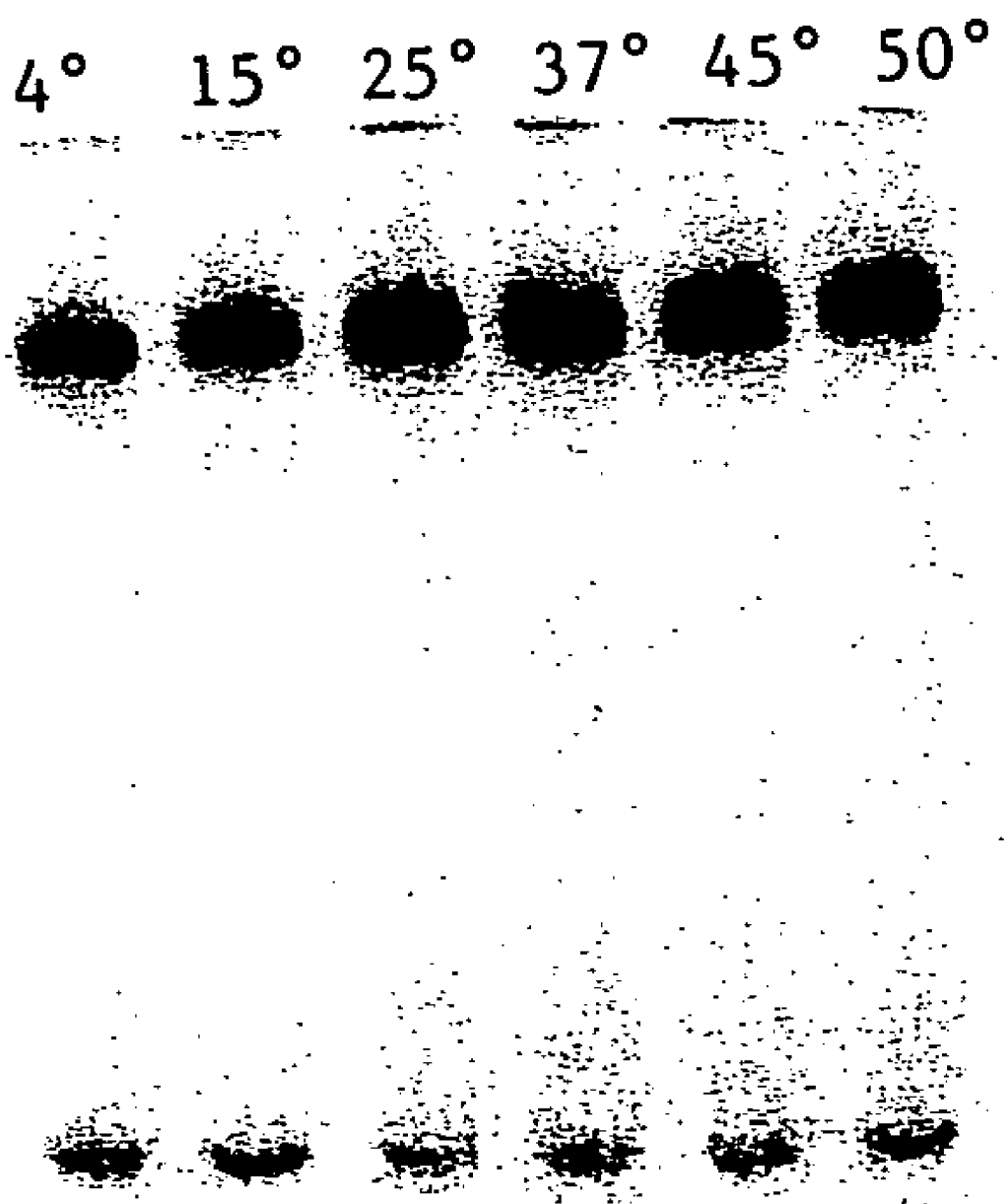
FIG. 6. Optimal annealing temperature for Y-arm formation. Y-arm formation using OligoT/OligoU as target, OligoX as incoming and Oligo5 as annealing oligonucleotide over a range of temperatures (in ° C.) as indicated.

We also determine the optimal temperature for the formation of Y-arms using the OligoT/OligoU duplex as the target, OligoX as the incoming oligonucleotide and Oligo5 as the annealing oligonucleotide. We vary the temperature as described above for the OligoA/OligoB experiment. As shown in FIG. 6, we test incubation at 4° C., 15° C., 25° C., 37° C., 45° C. and 50° C. We observe almost quantitative conversion of the free duplex target to oligonucleotide-containing Y-arms at all temperatures. However, as seen in the OligoA/OligoB experiment, increasing temperature clearly result in incremental increases in Y-arm formation, with optimal Y-arm formation at approximately 37° C.

It is readily apparent to one of skill in the art that this procedure can be applied to any target nucleic acid or set of oligonucleotides to determine the annealing temperature that leads to optimal formation of the corresponding double D-loop or Y-arm structure.

Figure 7:
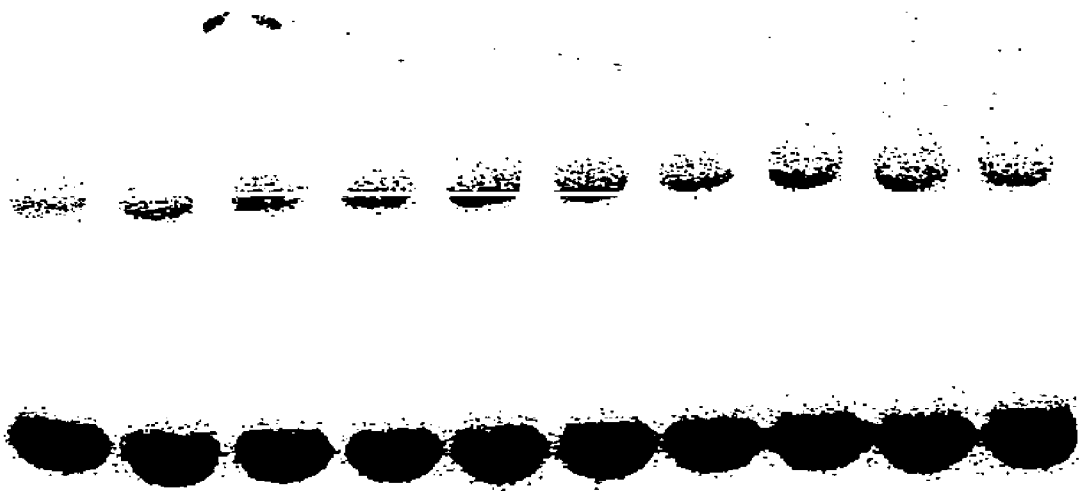
FIG. 7. Optimal annealing time for double D-loop formation. Double D-loop formation using OligoA/OligoB as target, OligoC as incoming and OligoI as annealing oligonucleotide over a range of times (in minutes) as indicated.

Determination of optimal annealing time. We test the formation of double D-loops using the OligoA/OligoB duplex as the target, OligoC as the incoming oligonucleotide and OligoI as the annealing oligonucleotide. We follow the protocol described in Example 1, except we vary the incubation time at 37° C. after the addition of the annealing oligonucleotide. As shown in FIG. 7, we test incubation for 1, 2, 3.5, 5, 7.5, 10, 20, 30, 45 and 60 minutes. We observe that double D-loop formation occurs very rapidly and that the extent of double D-loop formation increases up to an incubation time of approximately 10 minutes. After 10 minutes, we observe that the proportion of target nucleic acid in double D-loops begins to decrease, probably due to instability of the double D-loop, which contained only DNA oligonucleotides.

Figure 8:
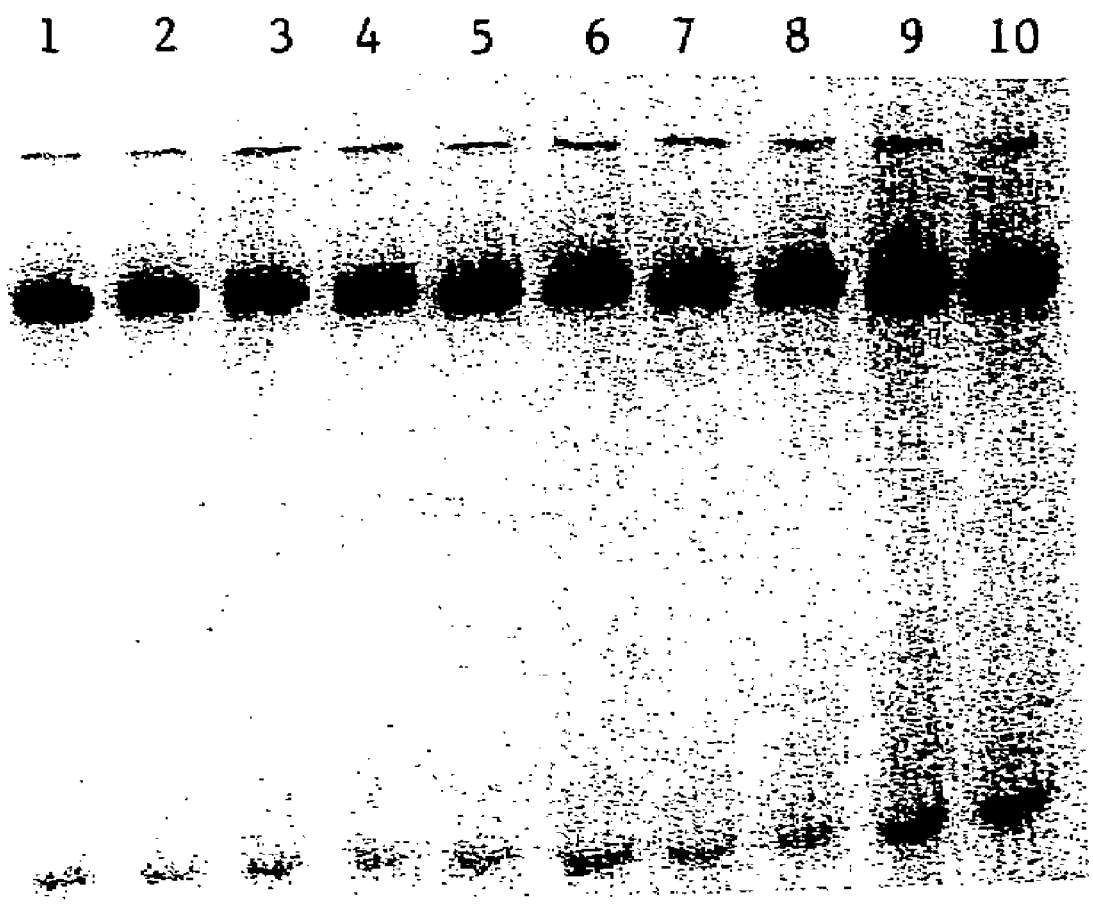
FIG. 8. Optimal annealing time for Y-arm formation. Y-arm formation using OligoT/OligoU as target, OligoX as incoming and Oligo5 as annealing oligonucleotide over a range of times (in minutes) as indicated.

We determine the optimal annealing time for the formation of Y-arms using the OligoT/OligoU duplex as the target, OligoX as the incoming oligonucleotide and Oligo5 as the annealing oligonucleotide. We vary the annealing time as described above for the OligoA/OligoB experiment. As shown in FIG. 8, we test incubation at 37° C. for 1, 2, 3, 4, 5, 6, 8, 10, 15 and 20 minutes. We observe almost quantitative conversion of the free duplex target to oligonucleotide-containing Y-arms at the one-minute time point and we do not observe a substantial increase in Y-arm formation with longer incubation times. In contrast to the OligoA/OligoB experiment, however, we do not see a reduction in the ratio of free duplex target to target complexed with oligonucleotides in the Y-arms, which is probably due to the fact that double D-loops formed at the end of a linear duplex target (i.e. Y-arms) are generally more stable that double D-loops formed in the middle of a linear duplex target.

It is readily apparent to one of skill in the art that this procedure can be applied to any target nucleic acid or set of oligonucleotides to determine the annealing time that leads to optimal formation of the corresponding double D-loop.

EXAMPLE 4

Determination of Optimal Oligonucleotide Lengths for Formation of Double D-Loops or Y-Arms Oligonucleotides used in this example. We use the OligoT/OligoU duplex as the target nucleic acid for these experiments. We use incoming DNA oligonucleotides complementary over a range of lengths to the end of the duplex target as follows: OligoV is a 20-mer with the sequence 5'-GCAGACTTCTCCTCAGGAGT-3' (SEQ ID NO: 10); OligoW is a 25-mer with the sequence 5'-GCAGACTTCTCCTCAGGAGTCAGGT-3' (SEQ ID NO: 11); OligoX is a 30-mer (SEQ ID NO: 8); OligoY is a 35-mer with the sequence 5'-GCAGACTTCTCCTCAGGAGTCAGGTGCACCATGGT-3' (SEQ ID NO: 12); OligoZ is a 40-mer with the sequence 5'-GCAGACTTCTCCTCAGGAGTCAGGTGCACCATGGTGTCTG-3' (SEQ ID NO: 13); and OligoI is a 46-mer with the sequence 5'-GCAGACTTCTCCTCAGGAGTCAGGTGCACCATGGTGTCTGTTTGAG-3' (SEQ ID NO: 14). We use annealing DNA oligonucleotides complementary to the end of the duplex target (and to the incoming oligonucleotides) over a range of lengths as follows: Oligo2 is a 20-mer with the sequence 5'-ACTCCTGAGGAGAAGTCTGC-3' (SEQ ID NO: 15); Oligo4 is a 25-mer with the sequence 5'-ACCTGACTCCTGAGGAGAAGTCTGC-3' (SEQ ID NO: 16); Oligo5 is a 30-mer with the sequence 5'-GTTGCACCTGACTCCTGAGGAGAAGTCTGC-3' (SEQ ID NO: 9); Oligo6 is a 35-mer with the sequence 5'-ACCATGGTGCACCTGACTCCTGAGGAGAAGTCTGC-3' (SEQ ID NO: 17); Oligo7 is a 40-mer with the sequence 5'-CAGACACCATGGTGCACCTGACTCCTGAGGAGAAGTCTGC-3' (SEQ ID NO: 18); and Oligo8 is a 46-mer with the sequence 5'-ACCTGACTCCTGAG-GAGAAGTCTGCCGTTACTGCCCTGTGGGGCAA-3' (SEQ ID NO: 19).

Figure 9:
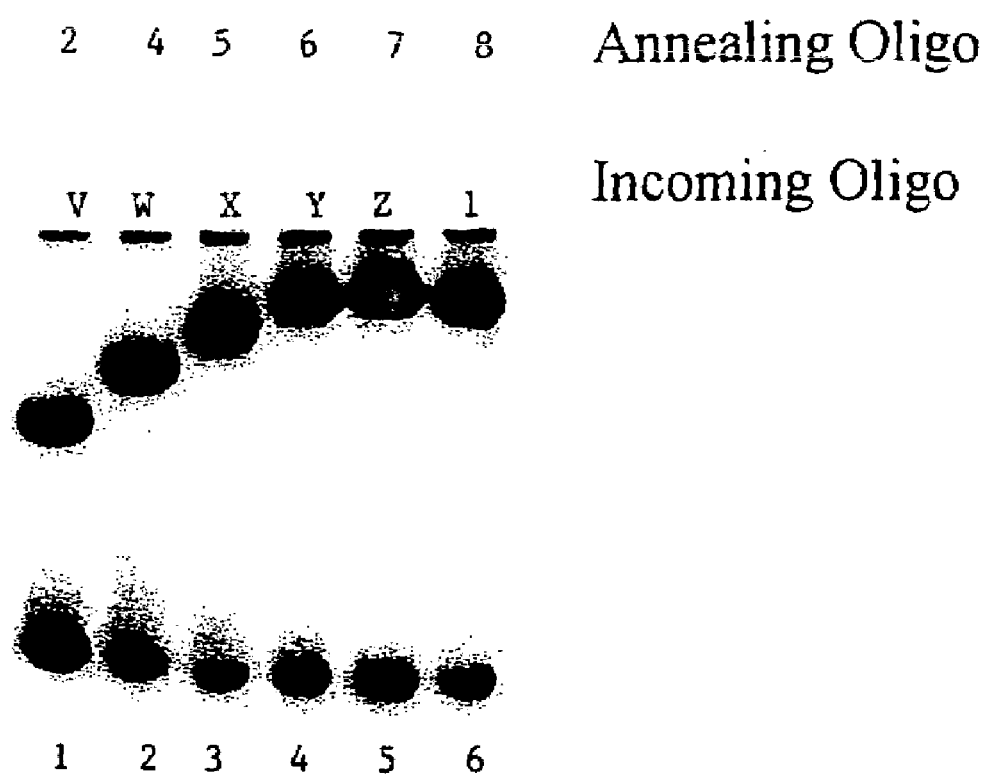
FIG. 9. Optimal oligonucleotide length for double D-loop (Y-arm) formation. Y-arm formation using OliaoT/OligoU as target and varying incoming and annealing oligonucleotides as indicated.
Figure 10:
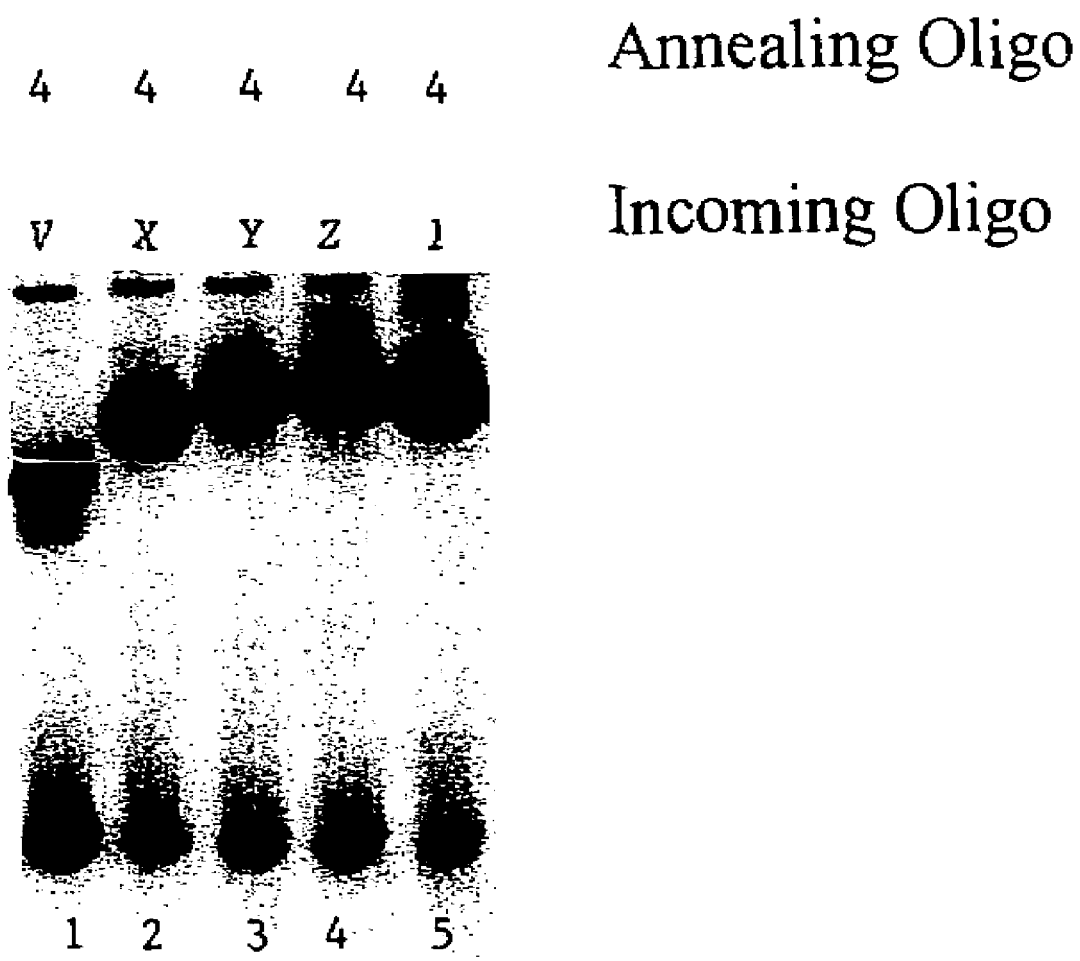
FIG. 10. Oligonucleotides can be of different lengths. Y-arm formation using OligoT/OligoU as target and varying incoming and annealing oligonucleotides as indicated.

Oligonucleotides of different lengths form double D-loops and Y-arms. We use the oligonucleotides described above to form Y-arms according to the protocol detailed in Example 1. As shown in FIG. 9, lanes 1–6, all of these oligonucleotides, ranging in size from 20 nucleotides to 46 nucleotides, efficiently form a Y-arm when the oligonucleotides are of equal length. This experiment does show, however, that longer oligonucleotides appear to form a Y-arm more efficiently. We show in FIG. 10, lanes 1–5, that the oligonucleotides used for the formation of a Y-arm do not need to be of the same length and that the annealing oligonucleotide can be either longer (lane 1) or shorter (lanes 2–5) than the incoming oligonucleotide.

It is readily apparent to one of skill in the art that this procedure can be applied to any target nucleic acid or set of oligonucleotides to determine the length of the oligonucleotides that lead to optimal formation of the corresponding double D-loop.

EXAMPLE 5

Determination of Optimal Oligonucleotide Composition for Formation of Double D-Loops Oligonucleotides used in this example. We use the OligoA/OligoB duplex as the target nucleic acid for these experiments. As the incoming oligonucleotide, we use either OligoC (SEQ ID NO: 3) or the complementary oligonucleotide which targets the opposite strand of the duplex target, designated "OligoD", which has the sequence 5'-CTGT-TGTGCCCAGTCCTAGCCGAATAGCCT-3' (SEQ ID NO: 20). We then use the following annealing oligonucleotides: OligoE is a DNA 30-mer with the sequence 5'-AGGCTAT-TCGGCTACGACTGGGCACAACAG-3' (SEQ ID NO: 21); OligoF is a DNA 25-mer with the sequence 5'-GCTAT-TCGGCTACGACTGGGCACAA-3' (SEQ ID NO: 22); OligoG is a DNA 20-mer with the sequence 5'-ATTCGGCTA CGACTGGGCAC-3' (SEQ ID NO: 23); OligoH is a DNA 30-mer with the sequence 5'-CTGTTGTGCCCAGTC CTAGCCGAATAGCCT-3' (SEQ ID NO: 24); OligoI is a DNA 25-mer with the sequence 5'-TTGTGCCCAGTC GTAGCCGAATAGC-3' (SEQ ID NO: 4); OligoJ is a 2'-O-methyl-RNA (2'-OMe-RNA) 25-mer with the sequence 5'-GCUAUUCGGCUACGACUGGGCACAA-3' (SEQ ID NO: 25); OligoK is a 2'-OMe-RNA 30-mer with the sequence 5'-CUGUUGUGCCCAGUC CUAGCCGAAUAGCCU-3' (SEQ ID NO: 26); OligoL is a 2'-O-methyl-RNA 25-mer with the sequence 5'-UUGUGC-CCAGUCGUAGCCGAAUAGC-3' (SEQ ID NO: 27); OligoM is a DNA 25-mer with phosphorothioate backbone linkages with the sequence 5'-TTGTGCCCAGTC GTAGCCGAATAGC-3' (SEQ ID NO: 28); OligoN is an LNA 15-mer (SEQ ID NO: 5); OligoO is a LNA-DNA-LNA 15-mer with the sequence 5'-GCCCagtcgtaGCCG-3', where the LNA residues are indicated with capital letters and the DNA residues are in lowercase (SEQ ID NO: 29); OligoP is an LNA-DNA-LNA 25-mer with the sequence 5'-TTGtgc-ccagtcgtagccgaatAGC-3', where the LNA residues are indicated with capital letters and the DNA residues are in lowercase (SEQ ID NO: 30); OligoQ is a PNA 18-mer with the sequence lys-ACGGGTCAGGATCGGCTT-gly (SEQ ID NO: 31); OligoR is a PNA 18-mer with the sequence lys-ACGGGTCAGCATCGGCTT-gly (SEQ ID NO: 32); OligoS is a PNA 20-mer with the sequence Ac-E-GTGC-CCAGTCCTAGCCGAAT-E-NH$_2$ (SEQ ID NO: 33). All of the oligonucleotides (or PNAs) are completely complementary to the target sequence except OligoH, OligoK, OligoQ and OligoS which each have a single basepair mismatch.

Figure 11:
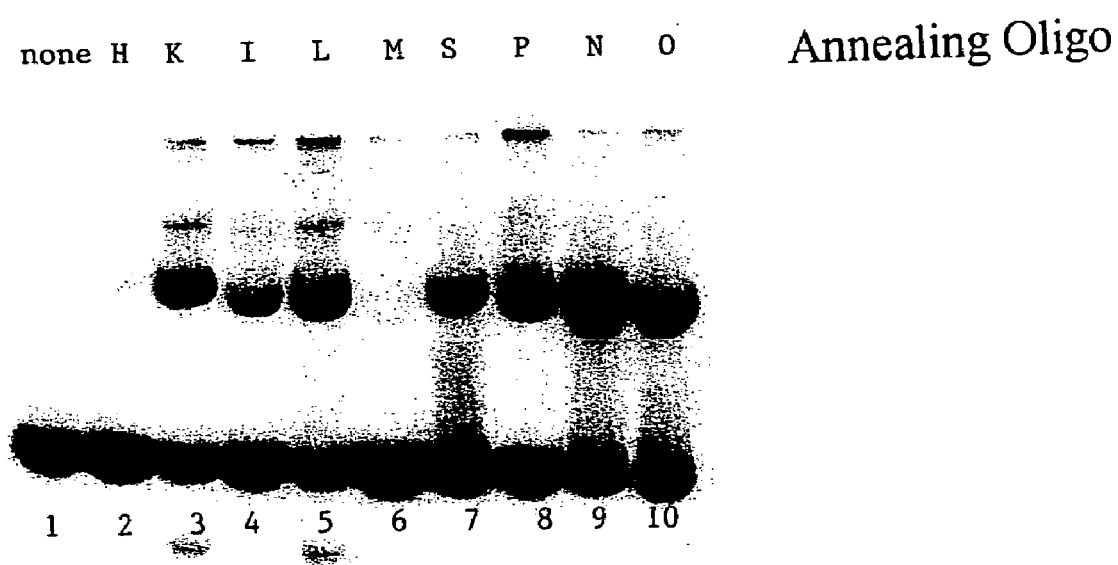
FIG. 11. Oligonucleotides with different modifications and/or mismatches. Double D-loop formation using OligoA/OligoB target, OligoC as incoming oligonucleotide and annealing oligonucleotide as indicated.

We show in FIG. 11 the formation of double D-loops using OligoA/OligoB as the target nucleic acid, OligoC as the incoming oligonucleotide and the oligonucleotides as the annealing oligonucleotide as indicated in the Figure. From these data it is apparent that oligonucleotides with a mismatched base can form a double D-loop (lanes 2 and 3) and that when we use 2'-OMe-RNA oligonucleotides (lanes 3 and 5), PNA (lane 7) and LNA oligonucleotides (lanes 8–10) as annealing oligonucleotides the formation of double D-loops is more robust that with DNA oligonucleotides. We also find that annealing oligonucleotides containing phosphorothioate modifications do not function as well as DNA for the formation of double D-loops (lane 6). Finally, this experiment confirms that oligonucleotides that are partially modified still enhance double D-loop formation relative to a DNA oligonucleotide (lanes 8 and 10).

Figure 12:
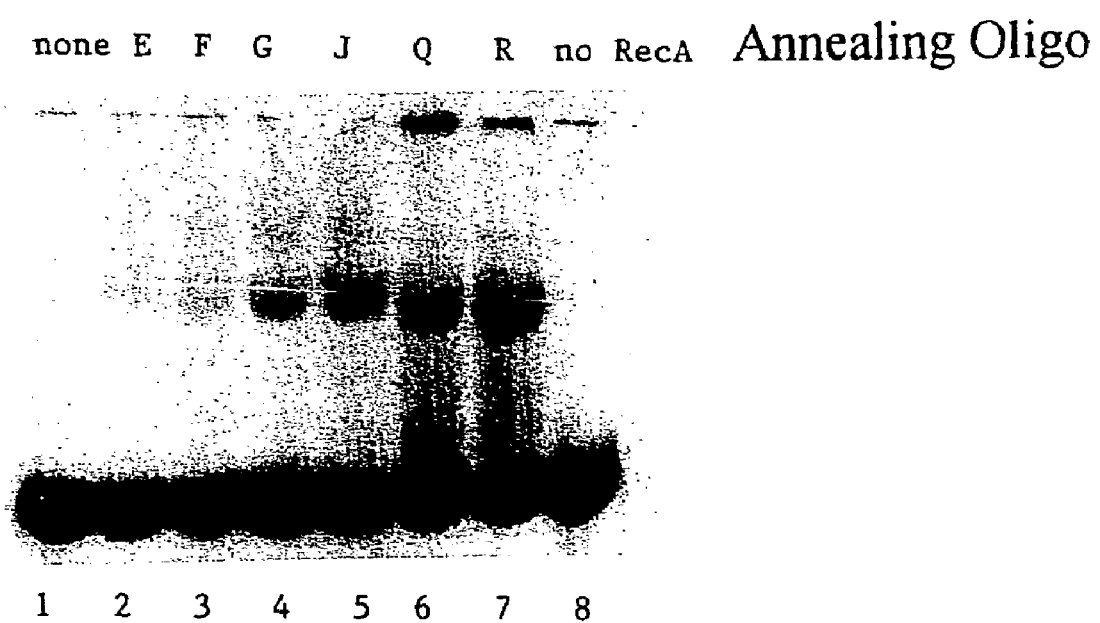
FIG. 12. Oligonucleotides with different modifications and/or mismatches. Double D-loop formation using OligoA/OligoB target, OligoD as incoming oligonucleotide and annealing oligonucleotide as indicated.

We confirm these results using the OligoA/OligoB target nucleic acid, OligoD as the incoming oligonucleotide, which recognizes the opposite strand of the OligoA/OligoB target nucleic acid relative to the previous experiment, and annealing oligonucleotides as indicated in FIG. 12. These data confirm that an oligonucleotide with a mismatched base can form a double D-loop (lane 6) and that when we use 2'-OMe-RNA oligonucleotides (lane 5) and PNA (lanes 6 and 7) as annealing oligonucleotides the formation of double D-loops is more robust that with DNA oligonucleotides. Combined with the previous experiment, these data also show that the double D-loop can be formed when the incoming oligonucleotide recognizes either strand of the target duplex.

It is readily apparent to one of skill in the art that this procedure can be applied to any target nucleic acid or set of oligonucleotides to determine the composition of the oligonucleotides that lead to optimal formation of the corresponding double D-loop and that a wide range of oligonucleotides functions in the methods of the invention.

EXAMPLE 6

Oligonucleotide: Target Capture and DNA Detection

Oligonucleotides used in this example. We use the OligoA/OligoB duplex as the target nucleic acid for these experiments. We use a $^{32}$P-labeled DNA oligonucleotide as the incoming oligonucleotide. We then use a biotin-labeled annealing oligonucleotide comprising at least one modified backbone that enhances hybrid stability or a modified base that enhances hybrid stability.

The capture/detection assay. We assay the presence of two oligonucleotides (one biotin-labeled and the other $^{32}$P-labeled) on the OligoA/OligoB duplex target molecule by capturing biotin-containing-oligonucleotide:target double D-loops on streptavidin-coated paramagnetic beads. The beads are washed in 1×RecA reaction buffer (1.0 mM ATP-γ-S; 25 mM Tris-acetate, pH 6.8; 1 mM dithiothreitol; and 1 mM magnesium acetate), 10×RecA reaction buffer, and finally in 1×RecA reaction buffer. Before DNA capture, equal aliquots of washed beads are added to individual 1.5 ml microcentrifuge tubes and the final wash buffer is removed. Liquid is removed from all bead suspensions by placing microcentrifuge tubes containing the bead mixtures in a magnetic separating rack.

The double D-loop containing samples from above are each added to a microcentrifuge tube containing an aliquot of the washed paramagnetic beads. The samples are mixed, and incubated at room temperature for 15 min. The mixtures are shaken several times during incubation to ensure efficient biotin:streptavidin interaction. After the capture reaction, i.e., the binding of streptavidin to biotin, the paramagnetic beads in each reaction are amassed with a magnet and the reaction buffer removed.

Each sample of beads is washed three times with 1×RecA reaction buffer. The presence of $^{32}$P-labeled probe strand is assessed by scintillation counting of the DNA captured by each bead reaction.

The results indicate that the hybridization product, containing two complementary but differentially labeled oligonucleotides, can be captured using the streptavidin interaction with the biotin labeled probe strand and subsequently detected by a label in the complementary probe strand.

EXAMPLE 7

RecA+ Facilitated DNA Amplification without Target DNA Denaturation

Reaction conditions for RecA protein facilitated DNA amplification have been described in U.S. Pat. No. 5,223, 414, incorporated herein by reference in its entirety.

We use a double-stranded duplex DNA target derived from plasmid DNA and two sets of oligonucleotides that form double D-loops at discrete sites separated by at least 200 nucleotides for ease of detection. We ensure that elongation of DNA primers occurs in only the desired direction, by terminating the 3'-ends of the appropriate primers with 2',3'-dideoxynucleotide, which lacks the 3'-hydroxyl group present in the conventional dNTPs and essential for elongation therefrom. We add the dideoxynucleotide to the primer using the enzyme terminal deoxynucleotide transferase.

We form double D-loops in the target nucleic acid using the two sets of oligonucleotides described above and the method described in Example 1. We then use the resulting two sets of double D-loops as the substrate in a typical DNA amplification reaction. The DNA reaction can be carried out in buffer containing 10 mM Tris-HCl (pH 7.5), 8–12 mM $MgCl_2$, and 50 mM NaCl supplemented with 200–750 μM dNTPs and DNA polymerase (e.g., exonuclease-free, DNA polymerase 1, Klenow, or T7 DNA polymerase). The reaction may additionally be supplemented with other enzymes or proteins (e.g. DNA helicase, DNA ligase and SSB protein) which may facilitate the formation of the specific amplification product. The reaction is allowed to proceed for as long as necessary at 37° C. Upon termination, samples are optionally deproteinized and analyzed by gel electrophoresis. After electrophoretic separation, the resulting amplified DNA can be visualized by either ethidium bromide staining of the DNA in the gel or by DNA hybridization with a target specific DNA probe. Alternatively, one of the DNA oligonucleotides can be biotinylated and the newly synthesized DNA captured by appropriate means and then detected as previously described.

DNA synthesis reactions are initiated by the addition of 1–2 unit(s) of exonuclease-free E. coli DNA polymerase I (U.S. Biochemicals) and 750 μM of each dNTP. The reactions are incubated at 37° C.

Following the initial addition of polymerase, the reactions can be supplemented with 1 unit of e.g., Klenow and/or additional dNTPs, at specific intervals spaced over the time course of the reaction.

Samples are treated with proteinase K, before being loaded for electrophoretic separation. After electrophoretic separation the resulting amplified DNA fragments can be visualized by either ethidium bromide staining of the gel or by hybridization with a target specific probe.

For hybridization analysis the gel can be transferred by standard protocols onto hybridization transfer membrane. We then detect the DNA using end-labeled probe corresponding to the DNA sequence of the target nucleic acid internal to the two double D-loops. We then detect hybridization signal by autoradiography or using a phosphorimager.

EXAMPLE 8

In Situ DNA Detection Utilizing the Double D-Loop Reactions

Preparation of oligonucleotide complex. We design oligonucleotides to form a double D-loop a target nucleic acid. One of these oligonucleotides comprises LNA and one of these oligonucleotides comprises a detectable fluorophore.

Preparation and transformation of HeLa cells. We grow HeLa cells at 37° C. and 5% $CO_2$ in a humidified incubator to a density of $2\times10^5$ cells/ml in an 8 chamber slide (Lab-Tek). We replace the DMEM with Optimem and transfect the cells with 5 μg of RecA-coated oligonucleotides that are previously complexed to 10 μg lipofectamine according to manufacturer's directions (Life Technologies). We treat the cells with the liposome, oligonucleotide mix for 6 hours at 37° C. We wash the treated cells with PBS and add fresh DMEM. After a 16–18 hour recovery period we assay the cells for fluorescence indicative of formation of the double D-loop. Specific signals are detected using standard fluorescence microscopy observation techniques.

EXAMPLE 9

RecA Mediated Double D-Loop Hybridization Reactions Using a Variety of Cofactors Oligonucleotides used in this example. We use the $^{32}$P-labeled OligoA/OligoB duplex as the target nucleic acid for these experiments. We use the DNA oligonucleotide OligoC as the incoming oligonucleotide and OligoN as the annealing oligonucleotide.

Double-D-loops can be formed using different cofactors for the RecA protein. We use the above-mentioned oligonucleotides to form double D-loops according to Example 1 except we substitute rATP, dATP or GTP-γ-S for ATP-γ-S in the RecA coating reaction. These reactions are performed with or without a regenerating system. The double D-loops are then deproteinized and detected as described previously.

EXAMPLE 10

Double D-Loop Formation Occurs Under a Range of Conditions

We test the ability of the double D-loop formation reaction to tolerate variations in reagent concentrations. We form double D-loops by combining 1.1 μl of fluorescently labeled incoming oligonucleotide LDF/45G (5'-Cy™5-GGTG- GAGAGGCTATTCGGCTAGGACTGGGCA-CAACAGACAATCGG-3'; SEQ ID NO: 34), 3 µl of 5× Synaptic Buffer (125 mM Tris-acetate, 5 mM Mg(acetate)$_2$ and 5 mM DTT), 1.5 µl 10 mM ATP-γ-S, water and 73.5 µM RecA. We vary the concentration of incoming oligonucleotide in the 1.1 µl sample using 2.25 µM, 4.5 µM, 9 µM or 18 µM. We vary the concentration of RecA relative to the concentration of the incoming oligonucleotide in the mixture, e.g. we add 0.5 µl RecA (73.5 µM) to the mixture when the concentration of the incoming oligonucleotide is 2.25 µM, 1.0 µl RecA when the concentration is 4.5 µM, and so on. Prior to the addition of RecA, water is added to the reaction mixture so that the final volume after the addition of RecA is 14 µl. We incubate this reaction for 10 minutes at 37° C. to allow for binding of RecA protein to the oligonucleotide ("presynapsis", see FIG. 1 for an outline of the method).

We prepare a double-stranded target by PCR from a neomycin phosphotransferase gene with a point mutation (Kan$^-$) using two oligonucleotide primers: 3910U (5'-CAGGGGATCAAGATCTGAT-3'; SEQ ID NO: 35) and 3CGT$^{th}$ (5'-GCTTCAGTGACAACGTCGAG-3'; SEQ ID NO: 36). The sequence of the resulting PCR product is shown in FIG. 13 (SEQ ID NO: 37). We add 3.5 µl of the PCR product at a concentration of 0.7 µM and 2.5 µl 74 mM Mg(acetate)$_2$. We incubate this reaction for 10 minutes at 37° C. to allow synapsis between the incoming oligonucleotide and the target nucleic acid molecule. We then add 0.74 µl of 27 µM annealing oligonucleotide KLO2 which comprises LNA modified residues (5'-GCCCAGTCGTAGCCG-3'; SEQ ID NO: 38). We incubate this reaction for 5 minutes at 37° C. to allow the annealing oligonucleotide to anneal to the target nucleic acid. We then stop the reaction by placing briefly on dry ice. We denature the RecA bound to the oligonucleotide:target complex by placing the reaction at about 4° C. in an ice bath and adding 2 µl of 10% SDS and 2 µl of 10× loading dye (15–25% Ficoll, optionally supplemented with 0.05% bromophenol blue).

We analyze the samples prepared as described above by separating on a 2.5% agarose gel at 4° C. The gel does not contain ethidium bromide. We strain the gels after running then with 1×SYBR® green, a dye which binds double-stranded DNA, and scan on a Typhoon™ imager. We monitor the gel positions of the double D-loop and the double-stranded target DNA by detecting the SYBR® green dye. We monitor the formation of double D-loops under these assay conditions by detecting the retarded migration of the fluorescently labeled incoming oligonucleotide.

We observe that double D-loops are formed at all incoming oligonucleotide concentrations. The fraction of target molecules that are in double D-loops at the different incoming oligonucleotide concentrations is 33% with 2.25 µM oligonucleotide; 37% with 4.5 µM oligonucleotide; 39% with 9 µM oligonucleotide; and 42% with 18 µM oligonucleotide. This indicates that the efficiency of double D-loop formation varies depending on the incoming oligonucleotide concentration. These results also indicate that double D-loop formation occurs over a wide range of oligonucleotide concentrations. Based on these results, unless indicated otherwise, the reaction in the following examples uses 1.11 µl of 18 µM incoming oligonucleotide and 2.0 µl of RecA.

EXAMPLE 11

Effect of Varying Annealing Oligonucleotide Composition and Target Sequence on Double D-Loop Formation We test the effect of varying the length, composition and sequence of the annealing oligonucleotide and the sequence of the target nucleic acid molecule on double D-loop formation.

We form double D-loops using the Kan$^-$ double-stranded PCR product as the target nucleic acid molecule following the protocol described in Example 10 except that we incubate the reaction after adding the annealing oligonucleotide for 10 minutes at 37° C. We analyze the samples prepared by separating on a 2.5% agarose gel at 4° C. as described above.

Figure 14:
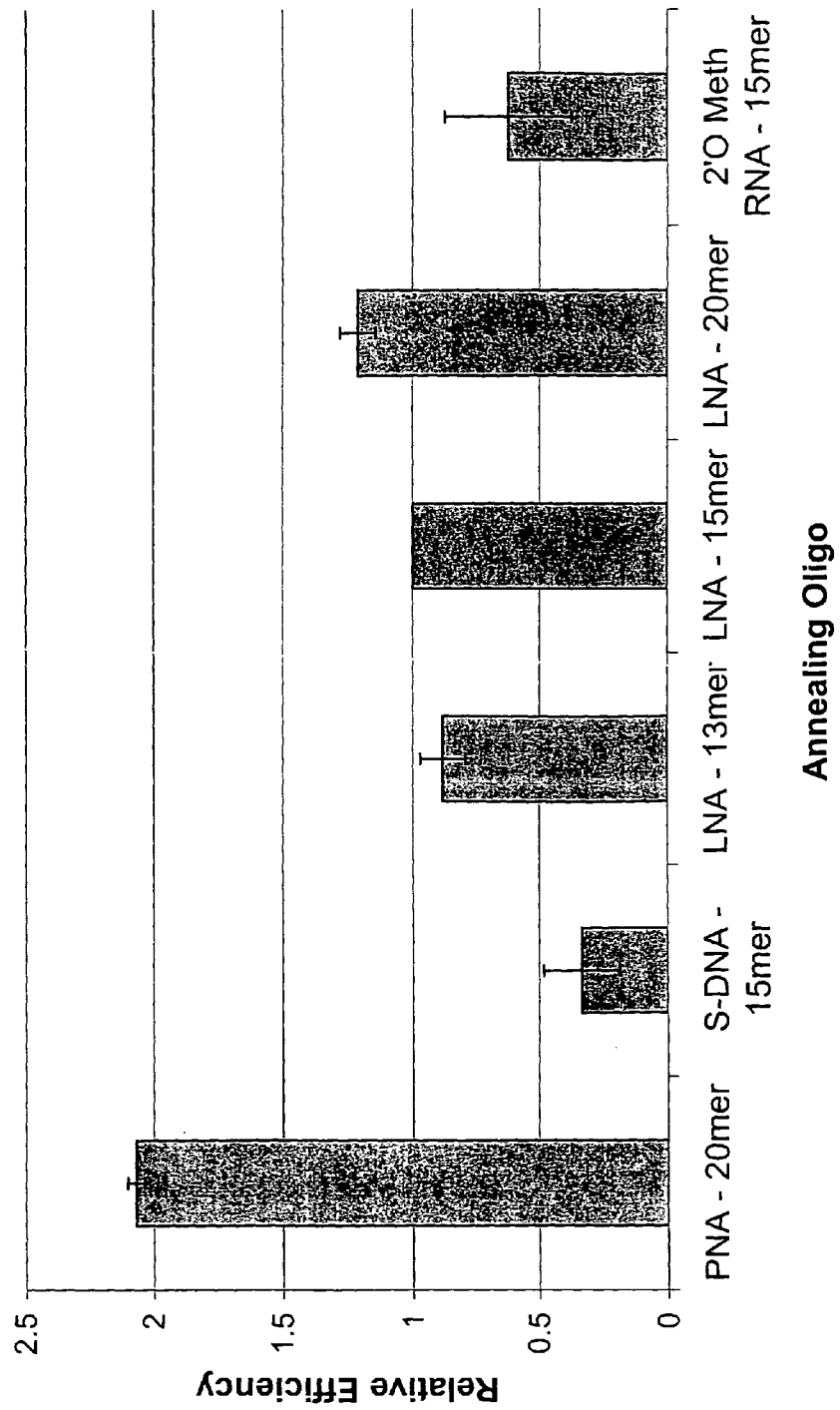
FIG. 14. Effect of annealing oligonucleotide on double D-loop formation. The figures shows the efficiency of double D-loop formation using the Kan⁻ PCR product as the target. Efficiency is normalized to double D-loop formation efficiency with KLO2 (indicated in the figure as LNA-15mer).

We test annealing oligonucleotides comprising PNA; DNA with a phosphorothioate backbone; 2'-O-methyl RNA; and LNA as indicated in Table 1. As indicated in Table 1, we test annealing oligonucleotides of various lengths. We normalize the percentage of double D-loop formation relative to the percentage of double D-loop formation using KLO2 as the annealing oligonucleotide to calculate relative efficiency. As indicated in FIG. 14, we observe that stable double D-loop formation occurs using any of the test annealing oligonucleotides. In this reaction, we observe that double D-loop formation is most efficient when oligonucleotides comprising PNA are used in the reaction. As indicated by the error bars in FIG. 14, the variation in the efficiency of double D-loop formation is very low, indicating that double D-loop formation can be used in quantitative as well as qualitative applications.

TABLE 1

Annealing Oligonucleotides for Kan- Target

| Name | Composition* | Sequence | SEQ ID NO: |
|---|---|---|---|
| KM2 | PNA | Ac-E-GTGCCCAGTCCTAGCCGAAT-E-NH$_2$ | 39 |
| UDS15G | DNA with phosphorothioate backbone | 5'-GCCCAGTCGTAGCCG-3' | 40 |
| UR15G | 2'-O-Me RNA | 5'-GCCCAGUCGUAGCCG-3' | 41 |
| KLO2 | LNA | 5'-GCCCAGTCGTAGCCG-3' | 42 |

TABLE 1-continued

Annealing Oligonucleotides for Kan- Target

| Name | Composition* | Sequence | SEQ ID NO: |
|---|---|---|---|
| KLO6 | LNA | 5'-CCCAGTCGTAGCC-3' | 43 |
| KLO15 | LNA | 5'-GTGCCCAGTCGTAGCCGAAT-3' | 62 |

*The underlined residues in KLO15 are DNA, the remainder are LNA.

We also form double D-loops using a PCR product produced from a plasmid containing the a functional hygromycin resistance gene (Hyg⁺) or a hygromycin resistance gene containing a point mutation (Hyg⁻; FIG. 15; SEQ ID NO: 44) using primers AUR123f (5'-TCTGCA-CAATATTTCAAGC-3'; SEQ ID NO: 45) and Hyg1560r (5'-AAATCAGCCATGTAGTG-3'; SEQ ID NO: 46). We follow the protocol described in this Example for the formation of double D-loops in the Kan⁻ PCR product using HygUDF/45G as the incoming oligonucleotide (5'-Cy™5-CGCAGCTATTTACCCGCAGGACCTATC-CACGCCCTCCTACATCGA-3'; SEQ ID NO: 47) and various annealing oligonucleotides as indicated in Table 2. We analyze the samples prepared by separating on a 2.5% agarose gel at 4° C. as described above.

Figure 16:
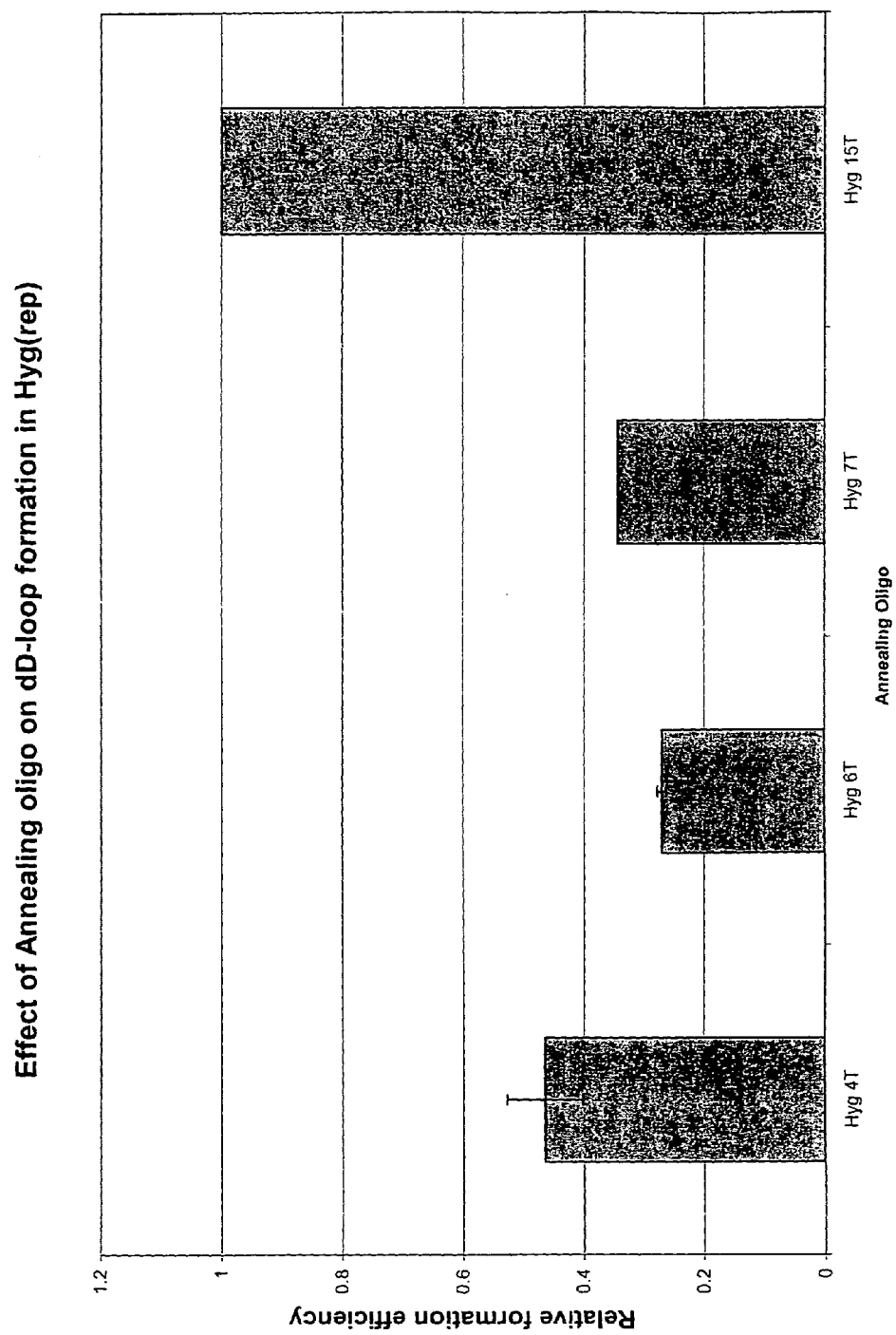
FIG. 16. Effect of annealing oligonucleotide on double D-loop formation. The figures shows the efficiency of double D-loop formation using the Hyg⁻ PCR product as the target. Efficiency is normalized to double D-loop formation efficiency with Hyg15T.

We test annealing oligonucleotides comprising LNA as indicated in Table 2. As indicated in Table 2, we also test annealing oligonucleotides of various lengths. We normalize the percentage of double D-loop formation relative to the percentage of double D-loop formation using Hyg15T as the annealing oligonucleotide to calculate relative efficiency. As indicated in FIG. 16, we observe that stable double D-loop formation occurs using any of the test annealing oligonucleotides. In this reaction, we observe that double D-loop formation is most efficient when we use the longest of the test oligonucleotides. As indicated by the error bars in FIG. 16, the variation in the efficiency of double D-loop formation in this reaction is also very low.

TABLE 2

Annealing Oligonucleotides for Hyg- Target

| Name | Composition* | Sequence | SEQ ID NO: |
|---|---|---|---|
| Hyg4 | LNA | 5'-GGATAGGTCC-3' | 48 |
| Hyg6 | LNA | 5'-TGGATAGGTCCT-3' | 49 |
| Hyg7 | LNA | 5'-GTGGATAGGTCCTGC-3' | 50 |
| Hyg15 | LNA | 5'-GTGGATAGGTCCTGC-3' | 51 |

*The underlined residues in these oligonucleotides are DNA, the remainder are LNA.

EXAMPLE 12

Double D-Loop Formation is Sequence-Specific

We test the effect of heterologous nucleic acid molecules on the efficiency of double D-loop formation. We form double D-loops using the Kan⁻ double-stranded DNA target as described in Example 10 except that we add heterologous competitor nucleic acid molecules along with the Kan⁻ target and Mg(acetate)₂. We perform the competition experiments using two competing nucleic acid molecules which do not have significant sequence homology with the Kan⁻ target or either the incoming or annealing oligonucleotides: the Hyg⁻ PCR product described above (FIG. 15; SEQ ID NO: 44) and poly dI-dC (Sigma).

We first add the Hyg⁻ PCR fragment to the mixture in a 1:1, 5:1 and 10:1 molar ratio relative to the amount of the Kan⁻ target nucleic acid molecule. We observe that the addition of the non-specific Hyg⁻ PCR fragment has no noticeable effect on the efficiency of double D-loop formation. We then add the poly dI-dC non-specific competitor nucleic acid molecule in vast excess ($10^1$-, $10^2$-, $10^3$-, $10^4$- and $10^5$-fold excess over the amount of the Kan⁻ target nucleic acid molecule). Even with such a vast excess of competitor, we observe no noticeable effect on the efficiency of double D-loop formation. In the presence of $10^5$-fold excess of the poly dI-dC non-specific competitor, we observed approximately 50% efficiency of double D-loop formation and the concentration of the Kan⁻ target nucleic acid molecule was limiting for double D-loop formation. These results indicate that double D-loop formation is sequence specific and that a nucleic acid molecule that represents a very small fraction of the nucleic acid molecules in a reaction serves as the target for double D-loop formation.

EXAMPLE 13

Double D-Loop Formation in a Linearized Plasmid Target

We test the efficiency of formation of double D-loops in a large plasmid target. We form double D-loops as described in Example 10 except that we add 2.5 µl (0.5 µg) of a linearized 8.2 kb plasmid comprising the Kan⁻ target gene and 7.35 μl of water. We add additional water to the reaction because of the higher target concentration. We then monitor the formation of double D-loops in the target plasmid using different annealing oligonucleotides (KM2, KLO2, KLO6, and KLO15; Table 1). We analyze the samples prepared by separating on a 1% agarose gel at 4° C. as described above and detect formation of the double D-loop by monitoring colocalization of the SYBR® green and the Cy™5 marker on the incoming oligonucleotide. We can not accurately assess the efficiency of double D-loop formation in these reactions because the formation of the double D-loop does not produce a large enough mobility shift in the target.

We observe efficient double D-loop formation in the plasmid target with any of the four annealing oligonucleotides. In contrast to our observations with a smaller Kan⁻ nucleic acid target molecule (Example 11; FIG. 14), we observe that the a shorter, 15mer oligonucleotide (KLO2; SEQ ID NO: 38) forms double D-loops at a slightly greater efficiency than a 20mer oligonucleotide (KLO15; SEQ ID NO: 43). In addition, we observe little or no difference in the apparent efficiency of double D-loop formation when we use an annealing oligonucleotide comprising PNA or LNA. These results indicate that the size of the target does not significantly affect the efficiency of double D-loop formation.

EXAMPLE 14

Topoisomerase I Enhances Double D-Loop Formation in a Supercoiled Plasmid Target We test the effect of adding topoisomerase I on the formation of double D-loops in a large, supercoiled plasmid target. We form double D-loops as described in Example 13 except that the plasmid comprising the Kan⁻ target gene is supercoiled and we add various amounts of topoisomerase 1 (0.5, 1.0 and 1.5 units[1]) to the reaction along with the target and we increase the incubation during that step to 30 minutes at 37° C. We then monitor the formation of double D-loops in the target plasmid using different annealing oligonucleotides (KM2 and KLO2; Table 1). We analyze the samples by separating on a 1% agarose gel at 4° C. as described above and detect formation of the double D-loop by monitoring colocalization of the bound SYBR® green marker and the Cy™5 marker on the incoming oligonucleotide.

[1] One unit of topoisomerase I relaxes completely 0.5 μg of plasmid in 30 minutes at 37° C.

We observe efficient double D-loop formation in the supercoiled plasmid target with either annealing oligonucleotide in both the presence and absence of topoisomerase 1. We observe that increasing the amount of topoisomerase I increases the amount of double D-loop formation. Both LNA and PNA support comparable levels of double D-loop formation in supercoiled target nucleic acid. The reactions in which the double D-loops are formed with PNA have less background than reactions using LNA. These results indicate that double D-loops can be formed in a supercoiled target following the teachings of the instant invention. Further, topoisomerase I enhances, but is not essential for, double D-loop formation in a supercoiled target.

EXAMPLE 15

Purification of Nucleic Acid Molecules Using Double D-Loops

We test whether the sequence specificity of double D-loop formation can be used for purification of a nucleic acid molecule of defined sequence from a complex mixture. We form double D-loops as described in Example 14 with the following exceptions: we use LDB/45G at a concentration of 18 μM and 5 units of topoisomerase I; the target nucleic acid is a 1:1 mixture of supercoiled pBR322 (Ap$^R$, Tet$^R$) and the supercoiled Kan$^R$ plasmid used in Example 14; and the reaction is incubated for 1 hour at 37° C. after addition of the target and topoisomerase I. LDB/45G has the same sequence as LDF/45G (used in Example 10), except that LDB/45G is not labeled with Cy™5 and has a biotin molecule attached at the 3' end by a TEG linker (5'-GGTGGAGAGGCTAT-TCGGCTAGGACTGGGCACAACAGACAA TCGG-3'bioTEG; SEQ ID NO: 52). Neither the incoming oligonucleotide (LDF/45G) or the annealing oligonucleotide (KLO2) has significant sequence complementarity to any sequence in pBR322.

We denature the RecA by cooling the reaction to about 4° C. by placing it in an ice bath and adding 2 μl 10% SDS as above. We then add KCl to a final concentration of 100 mM to precipitate the SDS, spin at 5000 rpm for 5 minutes in a microcentrifuge to pellet the precipitated SDS and transfer the supernatant to another tube. We add 2 μl of Dynabeads™ diluted in 1× Synaptic Buffer and incubate the reaction for 2 hours at 4° C. with vertical rotation to mix the solution. We then separate the magnetic Dynabeads™ by placing in a magnetic tube holder for 5 minutes and remove the supernatant. We wash twice in 1×TE buffer (GibcoBRL) by suspending the pellets in 50 μl ice-cold TE and agitating for 5 minutes at 4° C., separating the magnetic Dynabeads™ by placing in a magnetic tube holder for 5 minutes at 4° C. and removing the supernatant. We elute the plasmid DNA from the Dynabeads™ by adding 10 μl TE and heating the solution at 65° C. for 15 minutes. We collect the eluant and mix 5 μl with 20 μl electrocompetent DH10B cells. We electroporate the sample in a Cell-Porator® set at 330 μF, 4 Ω and 400 V. We remove the cells and place them in 1 ml of SOC medium and allow them to recover by incubating at 37° C. for 1 hour. We then dilute the cells into 4 ml of SOC medium and incubate on a shaker at 37° C. for 2 hours. We spin the cells down in a table top centrifuge for 5 minutes at 3750 rpm and resuspend the cells in 750 μl LB. We dilute these cells 1:10 into fresh LB and plate 100 μl of cells on LB plates supplemented with either 10 μg/ml tetracycline or 20 μg/ml kanamycin. We incubate the plates at 37° C. overnight and count the colonies after approximately 16 hours.

We observe extremely clean purification of the target plasmid. See Table 3. We are unable to determine the efficiency of purification because we observe no background colonies. These results indicate that the double D-loops formed according to the methods of the invention can be used to purify a nucleic acid molecule of known sequence away from other nucleic acid molecules.

TABLE 3

Separation of Kan$^R$ plasmid from pBR322 using double D-loops

| Sample | Tet$^R$ Colonies | Kan$^R$ Colonies |
|---|---|---|
| No Dynabeads ™ | >5000 | >5000 |
| No annealing oligonucleotide | 0 | 0 |
| No RecA | 0 | 6 |
| Complete reaction | 0 | 163 |

We also test whether the sequence specificity of double D-loop formation can be used for purification of a large nucleic acid molecule, for example a YAC. We inoculate a 5 ml culture of growth medium with a single colony from a YAC-containing strain of yeast and allow it to grown overnight until saturated. The following day we inoculate an additional 100 ml culture of growth medium with 1 ml of the overnight starter culture and grow this culture overnight until saturated. We use a hemocytometer to determine the cell count, which is generally about $1 \times 10^8$ cells/ml. We harvest the cells by centrifugation at 1300×g for 5 minutes and wash the pellet twice with 50 mM EDTA pelleting between washes for 5 minutes at 1300×g. We resuspend the cells in 50 mM EDTA to a concentration of $2 \times 10^9$ cells/ml and warm the cell suspension to 45° C. for 5 minutes. We add an equal volume of 1% InCert agarose in 50 mM EDTA, also prewarmed to 45° C. Alternatively, we use 1% or 2% SeaPlaque agarose. We mix the suspension by vortexing and pipet 500 µl aliquots into an agarose plug mold to harden. A 100 ml culture will yield about 20 plugs. We allow the plugs to set at room temperature or at 4° C. which takes about 15 minutes.

We extrude each plug into a dish and add 6 ml of freshly prepared yeast spheroplasting solution (40 ml 1 M sorbitol; 1.6 ml 0.5 M EDTA, pH 8.0; 0.4 ml 1 M Tris-HCl, pH 7.5; 40 µl 2-mercaptoethanol; and 40 mg yeast lytic enzyme (ICN)). We incubate the plugs at 37° C. for 2 to 4 hours with gentle shaking. We aspirate off the spheroplast solution, add 6 ml of LDS solution (1% lithium dodecyl sulfate; 100 mM EDTA; and 10 mM Tris-HCl, pH 8.0) and incubate at 37° C. with gentle shaking for 1 hour. We remove the solution and add 6 ml fresh LDS solution and incubate with gentle shaking at 37° C. overnight. We wash the plugs three times with gentle shaking at room temperature for 30 minutes with 6 ml 0.2×NDS (1×NDS is 0.5 M EDTA; 10 mM Tris base; 1% Sarkosyl; pH 9.5). We then wash the plugs five times with gentle shaking at room temperature for 30 minutes with 6 ml TE, pH 8.0. Plugs are either used directly or stored at 4° C. in covered with TE, pH 8.0.

We form a double D-loop in the YAC DNA in the agarose plug. We coat an incoming biotinylated oligonucleotide with RecA using a 5× amount of reactants as described in Example 10. We soak the plug in the solution containing the RecA-coated incoming oligonucleotide at 37° C. for between 20 minutes and 2 hours. We then add 5× volume of annealing oligonucleotide to the plug and soak for an additional 10 minutes to 1 hour. We insert the plug into a pulse field electrophoresis gel containing low melt agarose and a strip of conjugated agarose-streptavidin. We run the pulse field gel such that the DNA migrates across the streptavidin containing band allowing the YAC DNA containing the biotinylated double-D loop to be captured by the band. We excise the strip, heat it to melt the agarose, and elute the target from the band. We then transform spheroplasted yeast cells with the eluant by lithium acetate transformation.

EXAMPLE 16

Double D-Loop Hybridization Reactions can Discriminate Single Basepair Differences in Target Sequences We test whether the sequence specificity of double D-loop formation can be used to discriminate single basepair differences in a target sequence. We form the double D-loop as described in Example 10 except that we use a 50:50 mixture of two incoming oligonucleotides.

For example, we use 0.55 µl of an 18 µM solution of LDF/31 G (5'-Cy™5-GAGGCTATTCGGCTAG-GACTGGGCACAACAG-3'; SEQ ID NO: 53) and 0.55 µl of an 18 µM solution of LDF/31C (5'-Cy™3-GAGGCTAT-TCGGCTACGACTGGGCACAACAG-3'; SEQ ID NO: 54). The incoming oligonucleotide LDF/31G is complementary to the sequence of the mutant $Kan^R$ gene with the nucleotide corresponding to the point mutation centrally positioned and the incoming oligonucleotide LDF/31C is fully complementary to the sequence of a functional $Kan^R$ gene. The RecA-coated mixture of incoming oligonucleotides is added separately to either the Kan⁻ or the Kan⁺ PCR product. We add KM2 (SEQ ID NO: 39) as the annealing oligonucleotide. The KM2 oligonucleotide is perfectly complementary to the Kan⁻ target sequence. We also perform this experiment with an individual annealing oligonucleotide specific for the Kan⁺ target sequence and with a mixture of the two oligonucleotides. We perform these experiments with annealing oligonucleotides comprising a variety of combinations of modfied backbones or bases, including, for example, LNA, PNA, 2'-O-methyl RNA and 2-aminoadenine or cytosine/uracil substituted at the 5 position with a methyl, propynyl or bromo group.

We test the stability of the double D-loops formed as described above by denaturing the RecA bound to the oligonucleotide:target complex by adding SDS and, optionally KCl, and heating the samples to various temperature, e.g. 37° C., for varying periods of time. We then analyze the samples by separating by agarose gel electrophoresis. We monitor the stability of the double D-loops under these assay conditions by detecting the fluorescent labels on the Cy™3- and Cy™5-labeled oligonucleotides. The migration of these labeled oligonucleotides is retarded when they are part of a double D-loop complex.

We observe that double D-loop complexes in which the labeled incoming oligonucleotide is mismatched to the template are significantly less stable after denaturing the RecA than complexes in which the oligonucleotide is perfectly complementary to the template. This difference is readily detectable and after only 2.5 minutes at 37° C. a double D-loop made with a mismatched annealing oligonucleotide is almost completely undetectable. Accordingly, it is possible to determine which target sequence is in a sample based on which fluorescently labeled incoming oligonucleotide is present in the complex. This result indicates that stable double D-loops may be used to detect a single-nucleotide polymorphism in a target sequence or a mixture of target sequences.

EXAMPLE 17

Double D-Loop Hybridization Reactions Can Discriminate Single Basepair Differences in a Genomic Target Sequence We test the effect of varying the annealing oligo sequence to double D-loop formation efficiency in genomic DNA. We form double D-loops as in Example 16 using a 50:50 mixture of HYG(NT)D5Cy5/31C(rep) (5'-Cy™5-ATTTAC-CCGCAGGACCTATCCACGCCCTCCT-3'; SEQ ID NO: 55) which is perfectly matched to a hygromycin resistance gene with a point mutation (Hyg⁻) and HYG/(NT)D5Cy3/31G(cnv) (5'-Cy™3-ATTTACCCGCAGGACGTATC-CACGCCCTCCT-3'; SEQ ID NO: 56) which is perfectly matched to a copy of the hygromycin resistance gene which contains a point mutation but which remains functional (Hyg⁺). We add this to a genomic prep from two yeast strains, one from Mata-intHyg⁻ which contains an integrated Hyg⁻ gene. We compare this to a genomic prep of Mata-intHyg⁺ strain which contains an integrated Hyg⁺ gene. We use the following annealing oligonucleotides which are composed of LNA residues except for the underlined bases which are DNA: HygLNA15T (5'-GT<u>GG</u>AT<u>A</u>GGT <u>C</u>CTGC-3'; SEQ ID NO: 57) which is perfectly matched to Hyg⁻, Hyg15LNAT(cnv)C (5'-GT<u>GG</u>AT<u>A</u>CGT<u>C</u>CTGC-3'; SEQ ID NO: 58) which is perfectly matched to Hyg⁺, and Hyg15LNAT(wt)T (5'-GT<u>GG</u>AT<u>A</u>TGT<u>C</u>CTGC-3'; SEQ ID NO: 59) which is perfectly matched to the wild-type, functional hygromycin resistance gene sequence (Hyg(wt)). We add SDS to remove the RecA at 37° C. for 30 seconds, and run on a 0.7% agarose gel at 4° C.

Figure 17:
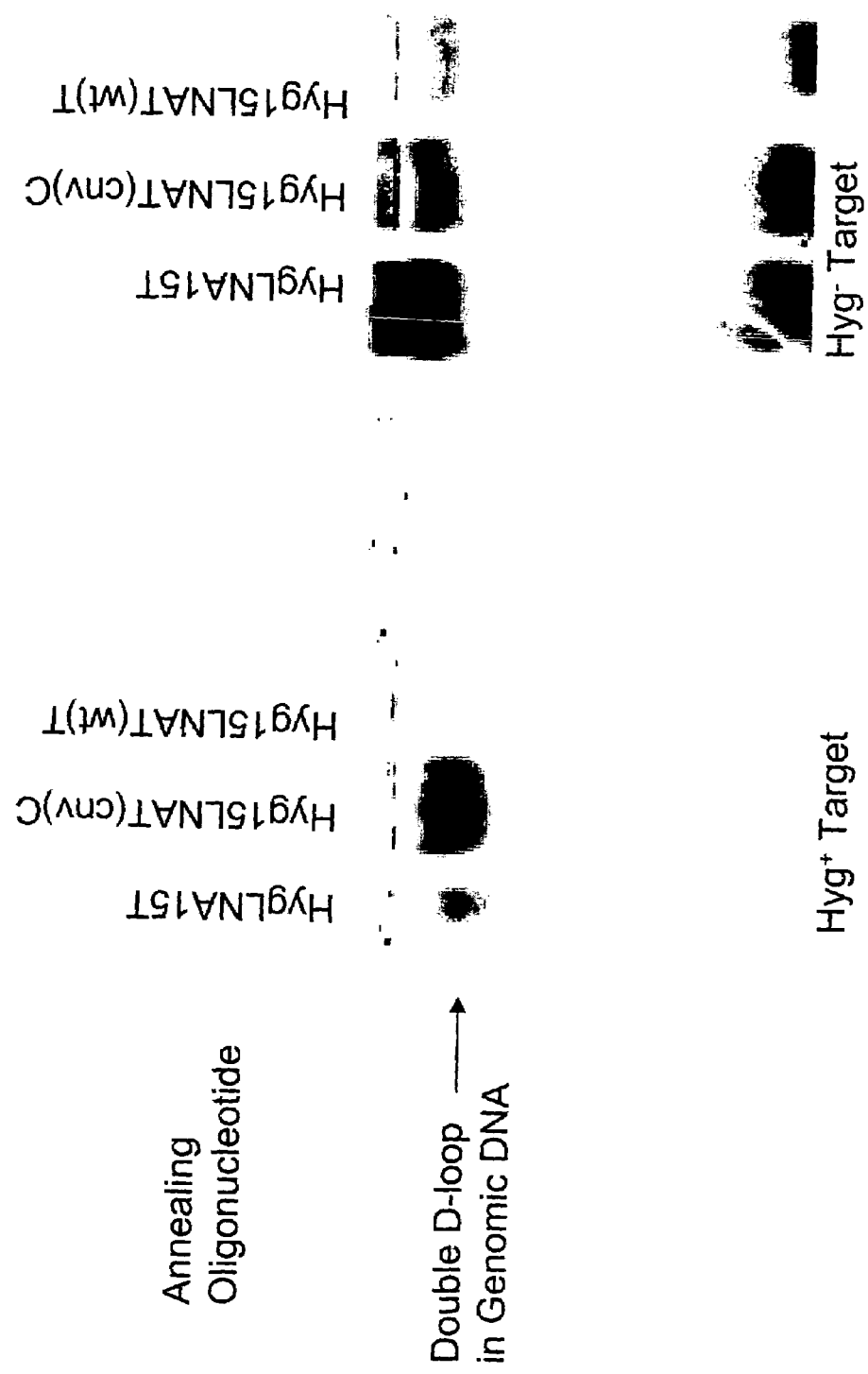
FIG. 17. Double D-loop formation in yeast genomic DNA. The figure shows double D-loop formation in yeast genomic DNA from strains with integrated copies of a Hyg⁻ and a Hyg⁺ target.

We observe efficient double D-loop formation in a genomic DNA target, indicating that target size and complexity do not limit the reaction. See FIG. 17. We also observe a readily detectable effect of the LNA sequence on formation efficiency. The presence of a mismatch on the annealing strand significantly destabilizes the molecule, as in Example 16. Accordingly, it is possible to discern the sequence of the target from a genomic DNA prep with high accuracy.

We also analyze metaphase chromosome spreads obtained from mammalian cells, including human cells. For example, we combine 0.5 to 0.8 ml whole blood with 0.2 ml phytohemaglutinin (PHA; M-form lyophilized from GibcoBRL or Sigma dissolved according to the manufacturer's instructions) and mix gently. The cells are added to a flask with 10 ml of complete cell culture media and we incubate them at 37° C. for 72 hours. We add 0.1 ml Actinomycin-D (5 mg/10 ml water) and incubate for 20 minutes. We then add 0.1 ml of colcemid (10 µg/ml; GibcoBRL) and incubate for 10 more minutes. We centrifuge the cells at 1000 rpm for 8 minutes, aspirate the supernatant and break up the cell pellet using a polyethylene pipet. We lyse the cells by adding prewarmed 37° C. hypotonic solution (75 mM KCl) drop by drop, mixing gently after each addition wth the pipet, until the final volume reaches about 2 ml. We then add a larger amount of hypotonic solution to bring the total volume to 10 ml and incubate at 37° C. for 15 minutes. We then at 10 drops of fixative solution (3 parts absolute methanol: 1 part glacial acetic acid) and mix with the pipet. We then centrifuge the cells at 1000 rpm for 8 minutes, aspirate the supernatant and break up the cell pellet using a polyethylene pipet. We add fixative solution drop by drop, mixing gently after each addition wth the pipet, until the final volume reaches about 2 ml. We then add a larger amount of fixative solution to bring the total volume to 10 ml. We then use these cells directly or store them in a refrigerator overnight.

We make slides with the cells as follows. We pellet the cells 20 minutes after the first addition of fixative solution by centrifuging at 1000 rpm for 8 minutes. We remove the supernatant using an aspirator, break up the cell pellet with the pipet, and resuspend in 10 ml of fixative solution by mixing gently. We repeat the pelleting and resuspending steps two more times. After the final resuspension, we leave 0.5 ml to 3.0 ml of fixative solution above the cell pellet, mix and drop four to six drops of cell suspension onto a clean wet slide. We then allow the slide to either air dry or place it on a hot plate at 55° C.–60° C. to dry.

We test the ability of the double D-loop formed according to the methods of the invention to discriminate single basepair differences in a genomic target sequence. W incubate the slides with two RecA-coated incoming oligonucleotides, each specific for a target sequence corresponding to the two interrogated alleles and each separately labeled, for example with Cy™-3 and Cy™5. We then add two annealing oligonucleotides complementary to the incoming oligonucleotides. We determine the sequence of the target by destabilizing the mismatched double D-loop by denaturing RecA and detecting the label on the oligonucleotide in the resulting double D-loop.

Alternatively, for detection of a target sequence in the genome, the slides are incubated sequentially with incoming and annealing oligonucleotides complementary to a desired genomic target. One of these oligonucleotides is labeled with a detectable moiety which is monitored to detect the formation of a stable double D-loop.

EXAMPLE 18

Assessment of Gene Amplification by Detecting Double D-Loop Formation

We test the ability of double D-loop formation to detect multiple copies of a gene in a genome. We use two strains of yeast containing one or multiple copies of the Hyg(rep) gene. We extract the genomic DNA and form double D-loops using the same conditions as described in Example 17, using HygUDF45G as the incoming oligo, and HygLNA15T as the annealing oligo. We run the reaction on a 1% agarose gel and quantify the amount of double D-loop formed using Molecular Dynamics ImageQuant™ and a Typhoon™ imager.

We observe that the intensity of double D-loop band increases in proportion to copy number of the inserted gene. This indicates that detection of double D-loop formation can be used to quantify amplification of a target duplex nucleic acid molecule, including a target gene such a ERB2 and c-Myc.

EXAMPLE 19

Sequence Specific Cleavage of Nucleic Acid Molecules Using Double D-Loops

We test whether the sequence specificity of double D-loop formation can be used to direct cleavage of a target nucleic acid molecule at a desired location. We form double D-loop targets by sequential hybridization. We combine oligonucleotides in two separate tubes as follows. In one tube we combine 7 µl of a 4 µM solution of ³²P-labeled 70mer oligonucleotide (OligoA; SEQ ID NO: 1); 1.9 µl of a 13 µM solution of a 25mer oligonucleotide (LD25G; 5'-GCTAT-TCGGCTAGGACTGGGCACAA-3', SEQ ID NO: 60); and 0.75 µl 10× hybridization buffer (100 mM Tris-HCl pH 7.5). In a second tube we combine 1.92 µl of a 12.5 µM solution of another 70mer oligonucleotide (OligoB; SEQ ID NO: 2); 1.46 µl of a 16.4 µM solution of another 25mer oligonucleotide (UD25C; 5'-TTGTGCCCAGTCCTAGCCGAAT-AGC-3'; SEQ ID NO: 61); 0.76 µl 10× hybridization buffer; and 3.46 µl water. These oligonucleotides are complementary to each other as follows: OligoA and OligoB are complementary; LD25G and UD25C are complementary; LD25G is complementary to OligoA such that LD25G hybridizes approximately in the center of OligoA; and UD25C is complementary to OligoB such that UD25C hybridizes approximately in the center of OligoB. We heat each of the separate tubes to 95° C. for 2 minutes and then cool to 60° C. for 20 minutes. This allows for OligoA/LD25G and OligoB/UD25C duplexes to form in the separate tubes. We then mix the tubes and incubate for 5 minutes at 37° C. This allows the overhanging ends on OligoA and OligoB to hybridize forming a double D-loop structure. We then cool the samples to 4° C. and separate the samples on a non-denaturing 12% polyacrylamide gel run at 4° C. for 2.5 hours at 8 W.

We detect the location of the double D-loops in the polyacrylamide gel by autoradiography and excise the band corresponding to the double D-loop. We incubate the polyacrylamide gel slice containing the double D-loops at 4° C. overnight in 1 ml of 2 mM Mg(acetate)$_2$ to elute the double D-loops from the gel slice. We transfer 250 µl of the solution containing the double D-loops into four different microfuge tubes and add 750 µl cold ethanol and 1 µg of poly dI-dC as a DNA carrier. We incubate this sample at 4° C. overnight and pellet the precipitate double D-loops by centrifugation at in a microcentrifuge at 4° C. for 30 minutes at 13,500 rpm. We aspirate the supernatant and wash the pellet by adding 200 µl 70% ethanol, centrifuging at 4° C. for 15 minutes at 13,500 rpm and aspirating the supernatant. We dissolve the double D-loops in 100 µl of 1×TBM (90 mM Tris-borate; 1 mM MgCl$_2$). We either use the double D-loops immediately or store at −20° C.

We combine 2 µl of $^{32}$P-labeled double D-loops in a reaction mix with 1 µl reaction buffer (300 mM BisTris-HCl pH 7.0; 500 mM KCl; 25 mM MnCl$_2$; 500 µg/ml BSA and 10 mM DTT), 0.5 µl MRE11 protein purified from *Saccaromyces cerevisiae*, 20 mM ATP and 4.5 µl water. Optionally, we include 0.5 µl RAD50 purified from *Saccaromyces cerevisiae*. If RAD50 is added, we add 4 µl water. We incubate this mixture for 30 minutes at 37° C. to allow MRE11-mediated cleavage of the target. We separate the reaction by either a non-denaturing 12% polyacrylamide gel electrophoresis or by denaturing (7M urea) 20% polyacrylamide gele electrophoresis.

We observe approximately 60% cleavage of the target nucleic acid molecule, i.e. approximately 40% of the $^{32}$P-labeled 70mer oligonucleotide. The cleavage that we observe is highly specific, with about 80% of cleavage occuring at the ends of the double D-loop. The localization of the cleavage site to the junction of the double D-loop at the 5' end of the incoming and annealing oligonucleotides indicates that it is possible to select a specific cleavage site by selecting specific incoming and annealing oligonucleotides. Accordingly, it is possible using this method to site-specifically cleave at any given base in a nucleic acid target with a defined sequence.

EXAMPLE 20

Double D-Loop Formation in Membrane-Bound Nucleic Acid Targets

We test the efficiency of double D-loop formation on a target crosslinked to a membrane. We crosslink via a Stratalink various concentrations of linear Hyg⁻ plasmid onto a Hybond-N+ (Amersham) membrane. We block the membrane by incubating at room temperature for 30 minutes with various concentrations of Denhardt's solution (100×: 2% BSA, 2% Ficoll, 2% PVP (polyvinylpyrrodilone)). We separately form the RecA filament using the same conditions as Example 10, with HygUDF45G with 5× the amount of reactants. We dilute the reaction to a final volume of 1 mL in 1× Synaptic buffer. Subsequently, we add the membrane to the reaction and incubate for 20 minutes at 37° C. We then add the 3.7 µL of 27 µM HYGLNA15T, and incubate 10 minutes at 37° C. We subsequently wash the membrane in various concentrations of SSC (20×: 3M NaCl, 0.3M Na$_3$Citrate) at elevated temperatures (37–65° C.), and visualize on the Molecular dynamics Typhoon™ Imager.

We observe efficient formation of double D-loop in a target crosslinked to a membrane. This results demonstrates that the methods of the invention can be used to form double D-loops in DNA crosslinked to a solid support such as a membrane, glass slide, or 96 well plate, with no serious detrimental effects. We can, thus, form a double-D loop sequence specifically, and visualize its structure without running a gel. Visualization of the formation of a stable double D-loop with a perfectly matched oligonucleotide as compared to the absence of a stable double D-loop structure with a mismatched oligonucleotide allows easy visualization of single nucleotide polymorphisms (SNPs).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for producing a stabilized double D loop at a target sequence within a double-stranded nucleic acid, the method comprising:
   providing a first oligonucleotide and a second oligonucleotide, said first and second oligonucleotides having at least a region of complementarity therebetween;
   wherein said first oligonucleotide is bound by a recombinase and has a region that is substantially complementary in sequence to a first strand of said target, and said second oligonucleotide is free of a recombinase and has a region that is substantially complementary in sequence to a second strand of said target;
   combining said first oligonucleotide with said double-stranded nucleic acid under conditions suitable for production of a double D-loop to form a mixture; and
   adding the second oligonucleotide to the mixture, producing-said stabilized double D loop at said target sequence within said double-stranded nucleic acid.

2. The method or claim 1, wherein said second oligonucleotide comprises at least one modification selected from the group consisting of: locked nucleic acid (LNA) monomer, 2'-OMe monomer, peptide nucleic acid, and phosphorothioate linkage.

3. The method of claim 1, wherein said recombinase is *E. coli* RecA protein.

4. The method of claim 1, further comprising the subsequent step of deproteinizing said double-stranded nucleic acid.

5. A method for detecting the presence of a desired target sequence within a double-stranded nucleic acid, the method comprising:
   providing a first oligonucleotide and a second oligonucleotide; wherein said first oligonucleotide is bound by a recombinase and has a region that is substantially complementary in sequence to a first strand of said target, and said second oligonucleotide is free of a recombinase and is substantially complementary in sequence to a second strand of said desired target, and said first oligonucleotide and second oligonucledtide have at least a region of complementarity therebetween;
   combining said first oligonucleotide with said double-stranded nucleic acid under conditions suitable for production of a double D-loop to form a mixture;
   adding the second oligonucleotide to the mixture; and
   detecting stabilized double D-loops having said oligonucleotides, said stable double D-loops signaling the presence of a desired target sequence.

6. The method of claim 5, wherein said second oligonucleotide comprise at least one modification selected from the group consisting of: locked nucleic acid (LNA) monomer, 2'-OMe monomer, peptide nucleic acid, and phosphorothloate linkage.

7. The method of claim 5, wherein at least one of said oligonucleotides is detectably labeled.

8. The method of claim 5, further comprising the step, after said combining and adding and before detecting, of: deproteinizing said nucleic acid sample.

9. A method for detecting the presence of a desired target sequence in a sample of double-stranded nucleic acids suspected of having sequences that differ at a target therein, the method comprising:
   contacting said sample of double-stranded nucleic acids with a first oligonucleotide form a mixture,
   adding a second oligonucleotide to the mixture, wherein said first oligonucleotide is bound by a recombinase, said second oligonucleotide is free of a recombinase, and said first and second oligonucleotides have at least a region of compiementarity therebetween,
   wherein both of said first and said second oligonucleotides have regions that are perfectly complementary to respective first and second strands of said desired target sequence, but at least one of said oligonucleotides is imperfectly matched in said region to each of said target sequences that differ from said desired sequence;
   deproteinizing said nucleic acids; and
   detecting stable double D-loops, said stable double D-loops signaling the presence of a desired target sequence.

10. The method of claim 9, wherein said second oligonucleotide comprises at least one modification selected from the group consisting of: locked nucleic acid (LNA) monomer, 2'-OMe monomer, peptide nucleic acid, and phosphorothioate linkage.

11. A method for detecting, in a sample of double-stranded nucleic acids suspected of having sequences that differ at a target, the presence of at least two different target sequences, the method comprising:
   forming double D-loops at said target by mixing a first oligonucleotide species with the sample of double-stranded nucleic acids to form a mixture, wherein said mixture includes at least two species of first oligonucleotide, each of said species having a region that is perfectly complementary to a distinct one of said different target sequences, and each of said species is bound by a recombinase;
   adding at least one species of a second oligonucleotide, wherein each of said at least one second oligonucleotide species is free of recombinase; and
   wherein said first oligonucleotides and said second oligonucleotides have at least a region of complementarity therebetween;
   deproteinizing said nucleic acids; and then
   discriminably detecting the species of first oilgonucieotldes present among stable D-loops, and thereafter determining the presence of at least two different target sequences.

12. The method of claim 11, wherein each of said first oligonucleotide species is discriminably labeled.

13. The method of claim 12, wherein each said first oligonucleotide specie is labeled with a different fluorophore, said fluorophores having distinguishable emission spectra.

14. The method of claim 11, wherein said double-stranded nucleic acids are selected from the group consisting of: linear nucleic acids, relaxed closed circular DNA, supercoiled circular DNA, artificial chromosomes, SACs, YACs, nuclear chromosomal DNA, and organelle chromosomal DNA.

15. The method of claim 11, wherein said second oligonucleotide comprises at least one modification selected from the group consisting of: locked nucleic acid (LNA) monomer, 2'-OMe monomer, peptide nucleic acid, and phosphorothioate linkage.

16. The method of claim 11, further comprising the step, after said deproteinizing and before said discriminably detecting, of: separating double D loop-containing nucleic acids from double-stranded nucleic acids lacking double D loops.

17. The method of claim 16, wherein said first oligonucleotide species, or said second oligonucleotide species, or both said first and second oligonucleotide species comprises a capture moiety, and said separating step is performed by specific binding to said capture moiety.

18. A method of purifying, from a mixture of double-stranded nucleic acids having sequences that differ at a target therein, double-stranded nucleic acids having a desired target sequence, the method comprising: forming double D loops at said target by mixing a first oligonucleotide with the mixture of double-stranded nucleic acids, wherein said first oligonucleotide is bound by a recombinase, adding a second oligonucleotide, wherein the second oligonucleotide is free of recombinase, and said first and second oligonucleotides have at least a region of complementarity therebetween, wherein said first oligonucleotide is perfectly complementary to a first strand of said desired target sequence, said second oligonucleotide is perfectly complementary to a second strand of said desired target sequence, and at least one of said oligonucleotides is imperfectly matched at each of said target sequences that differ from said desired target sequence; and then purifying double-stranded nucleic acids having stable D loops.

19. The method of claim 18, wherein said step of forming double D loops comprises: contacting said mixture of double-stranded nucleic acids first with said first, recombinase-bound oligonucleotide and thereafter with said second, recombinase-tree oligonucleotide.

20. The method of claim 18, further comprising the step, after forming double D loops and before purifying, of deproteinizing said double-stranded nucleic acids.

21. The method of claim 18, wherein said second oligonucleotide comprise at least one modification selected from the group consisting of: locked nucleic acid (LNA) monomer, 240 -OMe monomer, peptide nucleic acid, and phosphorothioate linkage.

22. The method of claim 18, wherein said first oligonucleotide, said second oligonucleotide, or both said first and second oligonucleotides comprises a capture moiety, and said purifying step is performed by specific binding to said capture moiety.

23. A method of protecting a restriction site target within double-stranded nucleic acids from cleavage during a restriction digest, comprising:
 forming double D-loops at said target by mixing a first oligonucleotide with the double-stranded nucleic acids to form a mixture, wherein said first oligonucleotide is bound by a recombinase and has at least a region that is substantially complementary in sequence to a first strand of said target;
 adding a second oligonucleotide to the mixture, wherein said second oligonucleotide is free of recombinase and has at least a region that is substantially complementary in sequence to a second strand of said target; and
 wherein said double D-loop is resistant to restriction cleavage at said target;
 digesting said double-stranded nucleic acids with a restriction enzyme that recognizes said target sequence; and
 detecting resistance of said target sequence to restriction cleavage.

24. The method of claim 23, wherein either or both of said oligonucleotide are methylated and said restriction enzyme target site is unmethylated.

25. The method of claim 23, wherein each of said oligonucleotides contains a mismatch to its respective target sequence strand.

26. The method of claim 23, wherein said second oligonucleotide comprises at least one modification selected from the group consisting of: locked nucleic acid (LNA) monomer, 2'-OMe monomer, peptide nucleic acid, and phosphorothioate linkage.

27. The method or claim 23, further comprising the step, after said forming of D loops and before digestion, of: deproteinizing said nucleic acids.

28. A method of cleaving at or near a target sequence within a double-stranded nucleic acid, the method comprising:
 forming a double D-loop at said target by mixing a first oligonucleotide with the double-stranded nucleic acid to form a mixture, wherein said first oligonucleotide has at least a region that is substantially complementary in sequence to a first strand of said target and is bound by a recombinase;
 adding a second oligonucleotide to the mixture, wherein said second oligonucleotide has at least a region that is substantially complementary in sequence to a second strand of said target and is free of recombinase;
 reacting said double-stranded nucleic acid with an enzyme that cleaves the double-stranded nucleic acid; and
 detecting cleavage at or near said target sequence.

29. A method of cleaving at or near a target sequence within a double-stranded nucleic acid, the method comprising:
 forming a double D-loop at said target by making a first oligonucleotide, with the double-stranded nucleic acid to form a mixture, wherein said first oligonucleotide is bound by a recombinase and has at least a region that is substantially complementary in sequence to a first strand of said target;
 adding a second oligonucleotide to the mixture, wherein said second oligonucleotide is free of recombinase and has at least a region that is substantially complementary in sequence to a second strand of said target;
 reacting said double-stranded nucleic acid with an enzyme that cleaves at or near said double D-loop; and
 detecting cleavage at or near said target sequence.

* * * * *

SEQUENCE LISTING

```
<160> NUMBER OF SEQ ID NOS: 62

<210> SEQ ID NO 1
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ctccggccgc ttgggtggag aggctattcg gctacgactg ggcacaacag acaatcggct    60
gctctgatgc                                                          70

<210> SEQ ID NO 2
<211> LENGTH: 70
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gcatcagagc agccgattgt ctgttgtgcc cagtcgtagc cgaatagcct ctccacccaa      60
gcggccggag                                                            70

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aggctattcg gctacgactg ggcacaacag                                      30

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ttgtgcccag tcgtagccga atagc                                           25

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: LNA monomer

<400> SEQUENCE: 5
gcccagtcgt agccg                                                      15

<210> SEQ ID NO 6
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
acaactgtgt tcactagcaa cctcaaacag acaccatggt gcacctgact cctgaggaga      60
agtctgc                                                               67

<210> SEQ ID NO 7
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 7
gcagacttct cctcaggagt caggtgcacc atggtgtctg tttgaggttg ctagtgaaca        60
cagttgt                                                                 67

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gcagacttct cctcaggagt caggtgcacc                                        30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gttgcacctg actcctgagg agaagtctgc                                        30

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gcagacttct cctcaggagt                                                   20

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gcagacttct cctcaggagt caggt                                             25

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gcagacttct cctcaggagt caggtgcacc atggt                                  35

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 13
gcagacttct cctcaggagt caggtgcacc atggtgtctg                              40

<210> SEQ ID NO 14
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gcagacttct cctcaggagt caggtgcacc atggtgtctg tttgag                       46

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
actcctgagg agaagtctgc                                                    20

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
acctgactcc tgaggagaag tctgc                                              25

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
accatggtgc acctgactcc tgaggagaag tctgc                                   35

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cagacaccat ggtgcacctg actcctgagg agaagtctgc                              40

<210> SEQ ID NO 19
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
acctgactcc tgaggagaag tctgccgtta ctgccctgtg gggcaa         46

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ctgttgtgcc cagtcctagc cgaatagcct         30

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aggctattcg gctacgactg ggcacaacag         30

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gctattcggc tacgactggg cacaa         25

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
attcggctac gactgggcac         20

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ctgttgtgcc cagtcctagc cgaatagcct         30

<210> SEQ ID NO 25
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (1)..(25)
<223> OTHER INFORMATION: 2'-OMe modified

<400> SEQUENCE: 25
gcuauucggc uacgacuggg cacaa                                              25

<210> SEQ ID NO 26
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(30)
<223> OTHER INFORMATION: 2'-OMe modified

<400> SEQUENCE: 26
cguuugugcc caguccuagc cgaauagccu                                         30

<210> SEQ ID NO 27
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(25)
<223> OTHER INFORMATION: 2'-OMe modified

<400> SEQUENCE: 27
uugugcccag ucguagccga auagc                                              25

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: phosphorothioate linkages

<400> SEQUENCE: 28
ttgtgcccag tcgtagccga atagc                                              25

<210> SEQ ID NO 29
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: LNA monomer
<220> FEATURE:
<221> NAME/KEY: modified_base
<222> LOCATION: (12)..(15)
<223> OTHER INFORMATION: LNA monomer

<400> SEQUENCE: 29
gcccagtcgt agccg                                                         15
```

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: LNA monomer
<220> FEATURE:
<221> NAME/KEY: modified_base
<222> LOCATION: (23)..(25)
<223> OTHER INFORMATION: LNA monomer

<400> SEQUENCE: 30
ttgtgcccag tcgtagccga atagc                                   25

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: PNA backbone

<400> SEQUENCE: 31
acgggtcagg atcggctt                                           18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: PNA backbone

<400> SEQUENCE: 32
acgggtcagc atcggctt                                           18

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: PNA backbone

<400> SEQUENCE: 33
gtgcccagtc ctagccgaat                                         20

<210> SEQ ID NO 34
<211> LENGTH: 45
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 34
ggtggagagg ctattcggct aggactgggc acaacagaca atcgg          45

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 35 cagggatca agatctgat          19

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 36
gcttcagtga caacgtcgag          20

<210> SEQ ID NO 37
<211> LENGTH: 306
<212> TYPE: DNA
<213> ORGANISM: Artificial Sequence
<220> FEATURE:
<223> OTHER INFORMATION: Description of Artificial Sequence:
    Synthetic Kan
    target nucleotide sequence

<400> SEQUENCE: 37 cagggatca agatctgatc aagagacagg atgaggatcg tttcgcatga ttgaacaaga        60
tggattgcac gcaggttctc cggccgcttg ggtggagagg ctattcggct atgactgggc       120
acaacagaca atcggctgct ctgatgccgc cgtgttccgg ctgtcagcgc aggggcgccc       180
ggttcttttt gtcaagaccg acctgtccgg tgccctgaat gaactgcagg acgaggcagc       240
gcggctatcg tggctggcca cgacgggcgt tccttgcgca gctgtgctcg acgttgtcac       300
tgaagc                                                                 306

<210> SEQ ID NO 38
<211> LENGTH: 15
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<221> NAME/KEY: modified_base
<222> LOCATION: (1)..(15)
<223> OTHER INFORMATION: LNA monomer

<400> SEQUENCE: 38
gcccagtcgt agccg          15

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

```
<220> FEATURE:
<221> NAME/KEY: misc_feature
<222> LOCATION: (1)..(20)
<223> OTHER INFORMATION: PNA backbone

<400> SEQUENCE: 39
gtgcccagtc ctagccgaat                                              20

<210> SEQ ID NO 40
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(15)
<223> OTHER INFORMATION: phosphorothioate linkages

<400> SEQUENCE: 40
gcccagtcgt agccg                                                   15

<210> SEQ ID NO 41
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: 2'-OMe modified

<400> SEQUENCE: 41
gcccagucgu agccg                                                   15

<210> SEQ ID NO 42
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: LNA monomer

<400> SEQUENCE: 42
gcccagtcgt agccg                                                   15

<210> SEQ ID NO 43
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(13)
<223> OTHER INFORMATION: LNA monomer

<400> SEQUENCE: 43
cccagtcgta gcc                                                     13

<210> SEQ ID NO 44
```

```
<211> LENGTH: 478
<212> TYPE: DNA
<213> ORGANISM: Artificial Sequence
<220> FEATURE:
<223> OTHER INFORMATION: Description of Artificial Sequence:
      Synthetic Hyg
      target nucleotide sequence

<400> SEQUENCE: 44
cgctgagata ggtgcctcac tgattaagca ttggtaactg tcagaccaag tttactcata    60
tatactttag attgatttaa aacttcattt ttaatttaaa aggatctagg tgaagatcct   120
ttttgataat ctcatgacca aaatcccttaa cgtgagttt tcgttccact gagcgtcaga   180
ccccgtagaa aagatcaaag gatcttcttg agatcctttt tttctgcgcg taatctgctg   240
cttgcaaaca aaaaaaccac cgctaccagc ggtggtttgt ttgccggatc aagagctacc   300 aactctttt ccgaaggtaa ctggcttcag cagagcgcag ataccaaata ctgtccttct   360
agtgtagccg tagttaggcc accacttcaa gaactctgta gcaccgccta catacctcgc   420
tctgctaatc ctgttaccag tggctgctgc cagtggcgat aagtcgtgtc ttaccggg    478

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 45
tctgcacaat atttcaagc                                                 19

<210> SEQ ID NO 46
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 46
aaatcagcca tgtagtg                                                   17

<210> SEQ ID NO 47
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cgcagctatt tacccgcagg acctatccac gccctcctac atcga                    45

<210> SEQ ID NO 48
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: LNA monomer
<220> FEATURE:
<221> NAME/KEY: modified_base
<222> LOCATION: (3)..(7)
<223> OTHER INFORMATION: LNA monomer
```

-continued

```
<220> FEATURE:
<221> NAME/KEY: modified_base
<222> LOCATION: (10)..(10)
<223> OTHER INFORMATION: LNA monomer

<400> SEQUENCE: 48
ggataggtcc                                                                10

<210> SEQ ID NO 49
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: LNA monomer
<220> FEATURE:
<221> NAME/KEY: modified_base
<222> LOCATION: (3)..(5)
<223> OTHER INFORMATION: LNA monomer
<220> FEATURE:
<221> NAME/KEY: modified_base
<222> LOCATION: (7)..(9)
<223> OTHER INFORMATION: LNA monomer
<220> FEATURE:
<221> NAME/KEY: modified_base
<222> LOCATION: (11)..(12)
<223> OTHER INFORMATION: LNA monomer

<400> SEQUENCE: 49
tggataggtc ct                                                             12

<210> SEQ ID NO 50
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: LNA monomer
<220> FEATURE:
<221> NAME/KEY: modified_base
<222> LOCATION: (6)..(7)
<223> OTHER INFORMATION: LNA monomer
<220> FEATURE:
<221> NAME/KEY: modified_base
<222> LOCATION: (9)..(12)
<223> OTHER INFORMATION: LNA monomer
<220> FEATURE:
<221> NAME/KEY: modified_base
<222> LOCATION: (14)..(15)
<223> OTHER INFORMATION: LNA monomer

<400> SEQUENCE: 50
gtggataggt cctgc                                                          15

<210> SEQ ID NO 51
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: LNA monomer
```

```
<220> FEATURE:
<221> NAME/KEY: modified_base
<222> LOCATION: (4)..(6)
<223> OTHER INFORMATION: LNA monomer
<220> FEATURE:
<221> NAME/KEY: modified_base
<222> LOCATION: (8)..(10)
<223> OTHER INFORMATION: LNA monomer
<220> FEATURE:
<221> NAME/KEY: modified_base
<222> LOCATION: (12)..(15)
<223> OTHER INFORMATION: LNA monomer

<400> SEQUENCE: 51
gtggataggt cctgc                                                        15

<210> SEQ ID NO 52
<211> LENGTH: 45
<212> TYPE: DNA
<213> ORGANISM: Artificial Sequence
<220> FEATURE:
<223> OTHER INFORMATION: Description of Artificial Sequence: Linker
      oligonucleotide

<400> SEQUENCE: 52
ggtggagagg ctattcggct aggactgggc acaacagaca atcgg                       45

<210> SEQ ID NO 53
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gaggctattc ggctaggact gggcacaaca g                                      31

<210> SEQ ID NO 54
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gaggctattc ggctacgact gggcacaaca g                                      31

<210> SEQ ID NO 55
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
atttacccgc aggacctatc cacgccctcc t                                      31

<210> SEQ ID NO 56
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
```

```
atttacccgc aggacgtatc cacgccctcc t                              31
```

<210> SEQ ID NO 57
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: LNA monomer
<220> FEATURE:
<221> NAME/KEY: modified_base
<222> LOCATION: (4)..(6)
<223> OTHER INFORMATION: LNA monomer
<220> FEATURE:
<221> NAME/KEY: modified_base
<222> LOCATION: (8)..(10)
<223> OTHER INFORMATION: LNA monomer
<220> FEATURE:
<221> NAME/KEY: modified_base
<222> LOCATION: (12)..(15)
<223> OTHER INFORMATION: LNA monomer

<400> SEQUENCE: 57

```
gtggataggt cctgc                                                15
```

<210> SEQ ID NO 58
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: LNA monomer
<220> FEATURE:
<221> NAME/KEY: modified_base
<222> LOCATION: (4)..(6)
<223> OTHER INFORMATION: LNA monomer
<220> FEATURE:
<221> NAME/KEY: modified_base
<222> LOCATION: (8)..(10)
<223> OTHER INFORMATION: LNA monomer
<220> FEATURE:
<221> NAME/KEY: modified_base
<222> LOCATION: (12)..(15)
<223> OTHER INFORMATION: LNA monomer

<400> SEQUENCE: 58

```
gtggatacgt cctgc                                                15
```

<210> SEQ ID NO 59
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: LNA monomer
<220> FEATURE:
<221> NAME/KEY: modified_base
<222> LOCATION: (4)..(6)
<223> OTHER INFORMATION: LNA monomer
<220> FEATURE:
<221> NAME/KEY: modified_base

```
<222> LOCATION: (8)..(10)
<223> OTHER INFORMATION: LNA monomer
<220> FEATURE:
<221> NAME/KEY: modified_base
<222> LOCATION: (12)..(15)
<223> OTHER INFORMATION: LNA monomer

<400> SEQUENCE: 59
gtggatatgt cctgc                                                      15

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gctattcggc taggactggg cacaa                                           25

<210> SEQ ID NO 61
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
ttgtgcccag tcctagccga atagc                                           25

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: LNA monomer
<220> FEATURE:
<221> NAME/KEY: modified_base
<222> LOCATION: (5)..(6)
<223> OTHER INFORMATION: LNA monomer
<220> FEATURE:
<221> NAME/KEY: modified_base
<222> LOCATION: (8)..(8)
<223> OTHER INFORMATION: LNA monomer
<220> FEATURE:
<221> NAME/KEY: modified_base
<222> LOCATION: (10)..(15)
<223> OTHER INFORMATION: LNA monomer
<220> FEATURE:
<221> NAME/KEY: modified_base
<222> LOCATION: (18)..(20)
<223> OTHER INFORMATION: LNA monomer

<400> SEQUENCE: 62
gtgcccagtc gtagccgaat                                                 20
```